(12) United States Patent
Heilmann et al.

(10) Patent No.: US 9,920,017 B2
(45) Date of Patent: Mar. 20, 2018

(54) HETEROCYCLIC COMPOUNDS AS PESTICIDES

(71) Applicant: BAYER CROPSCIENCE AKTIENGESELLSCHAFT, Monheim am Rhein (DE)

(72) Inventors: Eike Kevin Heilmann, Duesseldorf (DE); Heinz-Juergen Wroblowsky, Langenfeld (DE); Axel Trautwein, Duesseldorf (DE); Joerg Greul, Leverkusen (DE); Hardwin Dembski, Erkrath (DE); Kerstin Ilg, Köln (DE); Daniela Portz, Vettweiß (DE); Ulrich Goergens, Ratingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/123,637

(22) PCT Filed: Mar. 4, 2015

(86) PCT No.: PCT/EP2015/054550
§ 371 (c)(1),
(2) Date: Sep. 3, 2016

(87) PCT Pub. No.: WO2015/132313
PCT Pub. Date: Sep. 11, 2015

(65) Prior Publication Data
US 2017/0073318 A1    Mar. 16, 2017

(30) Foreign Application Priority Data
Mar. 6, 2014 (EP) .................................. 14157977

(51) Int. Cl.
| C07D 249/14 | (2006.01) |
| C07D 257/06 | (2006.01) |
| C07D 401/04 | (2006.01) |
| A01N 43/653 | (2006.01) |
| A01N 43/713 | (2006.01) |

(52) U.S. Cl.
CPC ......... *C07D 257/06* (2013.01); *A01N 43/653* (2013.01); *A01N 43/713* (2013.01); *C07D 249/14* (2013.01); *C07D 401/04* (2013.01)

(58) Field of Classification Search
None
See application file for complete search history.

(56) References Cited

U.S. PATENT DOCUMENTS

| 9,173,396 B2 | 11/2015 | Bretschneider et al. | |
| 2015/0239847 A1* | 8/2015 | Heilmann | A01N 43/653 |
| | | | 514/255.05 |

FOREIGN PATENT DOCUMENTS

| EP | 0957094 A1 | 11/1999 | | |
| WO | 2012006473 A1 | 1/2012 | | |
| WO | 2012052412 A1 | 4/2012 | | |
| WO | 2012116246 A2 | 8/2012 | | |
| WO | WO 2014/053450 | * 4/2014 | ........... | A01N 43/653 |
| WO | WO 2014/187928 | * 11/2014 | ............. | A01N 43/56 |

OTHER PUBLICATIONS

STN Registry database entry for CAS RN 31709-15-6 (Entered STN database Nov. 16, 1984), Accessed Jul. 12, 2017.*
STN Registry database entry for CAS RN 249893-20-7 (Entered STN database Dec. 3, 1999), Accessed Jul. 12, 2017.*
International Search Report dated May 26, 2015, issued in PCT/EP2015/054550.
European Search Report dated Jul. 7, 2014, issued in counterpart application No. EP 14157977.
Zhang, Hai-Hao et al., "Synthesis and Characterization of 3-amino (nitro)-5-nitro-1, 2, 4-triazole derivatives" XP002726710.
Trinka, Peter et al., "Triazoles. XXXVI. The arylation of 5-amino-3-(methylthio)-1H-1,2,4-triazole with activated aryl chlorides" (Jul. 3, 2014) XP00272671.1.
Reiter, Jozsef et al., "1, 2, 4-Triazole derivatives" (Mar. 7, 2014) XP-002726712.

* cited by examiner

Primary Examiner — Alicia L Otton
(74) Attorney, Agent, or Firm — McBee Moore Woodward & Vanik IP, LLC

(57) ABSTRACT

The present application relates to novel heterocyclic compounds, to the use thereof for controlling animal pests including arthropods, insects and nematodes, and to processes and intermediates for preparation of the novel compounds.

29 Claims, No Drawings

HETEROCYCLIC COMPOUNDS AS PESTICIDES

CROSS REFERENCE TO RELATED APPLICATIONS

This application is a § 371 National Stage Application of PCT/EP2015/054550, filed Mar. 4, 2015, which claims priority to EP 14157977.1, filed 6 Mar. 2014.

BACKGROUND

Field of the Invention

The present application relates to novel heterocyclic compounds, to the use thereof for controlling animal pests including arthropods, insects and nematodes, and to processes and intermediates for preparation of the novel compounds.

Description of Related Art

Derivatives of 1-aryl-3-aroylamino-1,2,4-triazoles are known from WO 2012/006473.

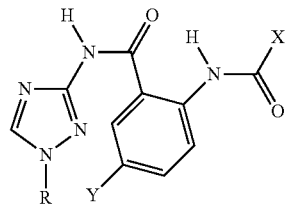

The compounds described therein have activity as phosphatase inhibitors.

Moreover, the following compounds are known in Scifinder as "Commercial Source" (CAS No. of the 2-Cl compound=321434-03-1, that of the 4-Cl compound=303144-57-2), without description of any use:

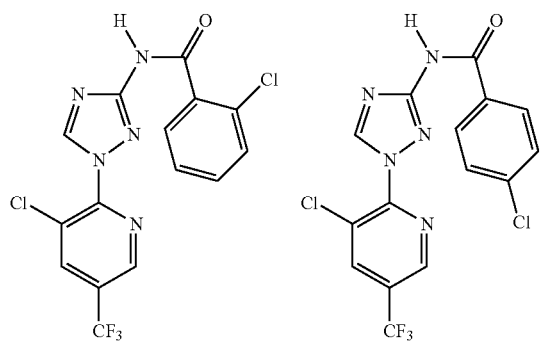 [SMILES: O=C(Nc1ncn(-c2ncc(C(F)(F)F)cc2Cl)n1)c1ccccc1Cl ; O=C(Nc1ncn(-c2ncc(C(F)(F)F)cc2Cl)n1)c1ccc(Cl)cc1]

Crop protection agents, which also include pesticides, have to meet many demands, for example in relation to efficacy, persistence, and spectrum of action and possible use. Questions of toxicity and of combinability with other active ingredients or formulation auxiliaries play a role, as does the question of the expense that the synthesis of an active ingredient entails. In addition, resistances can occur. For all these reasons, the search for novel crop protection compositions cannot be considered to be complete, and there is a constant need for novel compounds having properties which, compared to the known compounds, are improved at least in relation to individual aspects.

SUMMARY

It was an object of the present invention to provide compounds which widen the spectrum of the pesticides in various respects.

This object, and further objects which are not stated explicitly but can be discerned or derived from the connections discussed herein, are achieved by compounds of the formula (I)

in which
A is a radical from the group of

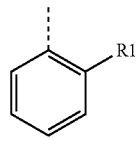
A-1

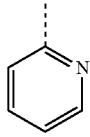
A-2

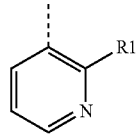
A-3

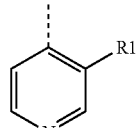
A-4

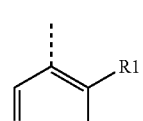
A-5

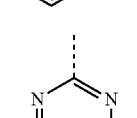
A-6

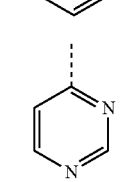
A-7

-continued

A-8
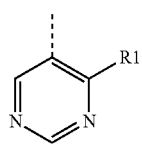

A-9
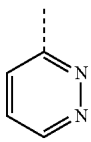

A-10
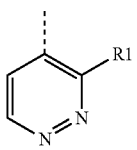

A-11
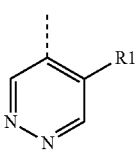

A-12
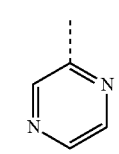

in which the broken line denotes the bond to Q and where A additionally bears m R2 substituents, Q is a radical from the group of Q-1
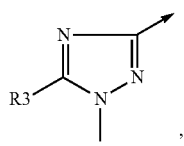
, Q-2
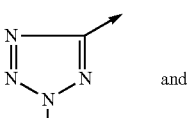
and Q-3
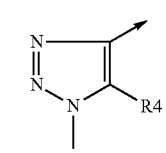

in which the nitrogen is joined to the ring A and the arrow in each case denotes the bond to D, and D is the radical of the formula

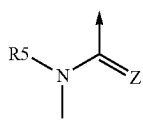

in which the nitrogen is bonded to Q and the arrow denotes the bond to B,

B is a radical from the group of

B-1
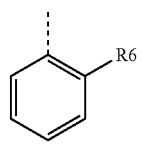

B-2
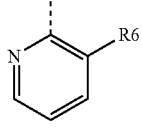

B-3
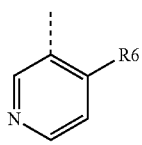

B-4
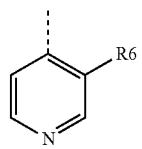

B-5
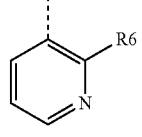

B-6
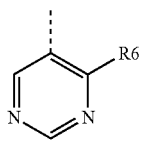

B-7
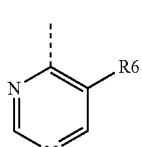

B-8
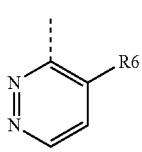

-continued
B-9 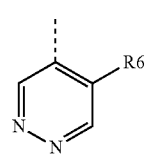
B-10 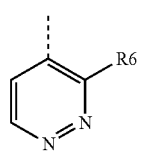
B-11 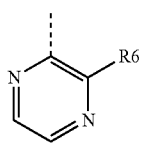
B-12 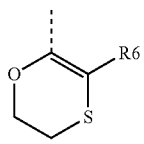
B-13 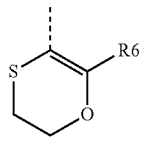
B-14 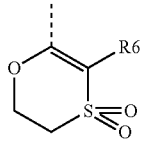
B-15 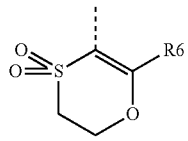
B-16 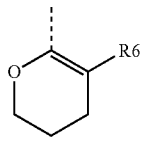
B-17 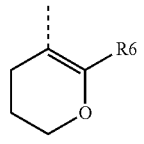
B-18 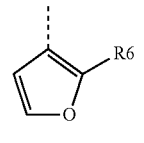
B-19 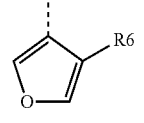
-continued
B-20 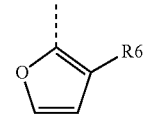
B-21 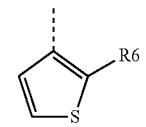
B-22 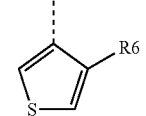
B-23 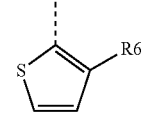
B-24 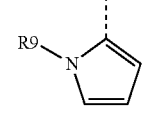
B-25 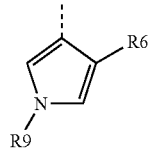
B-26 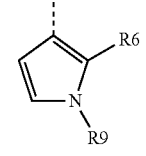
B-27 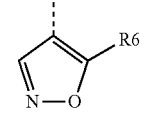
B-28 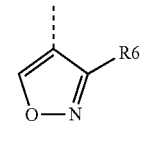
B-29 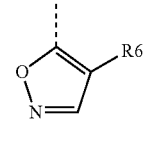
B-30 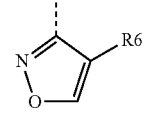

B-31 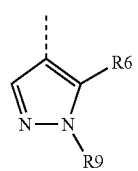
B-32 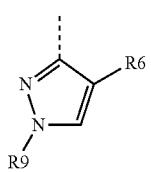
B-33 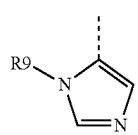
B-34 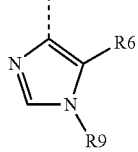
B-35 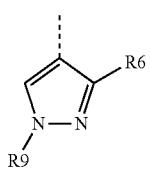
B-36 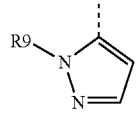
B-37 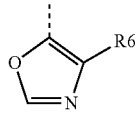
B-38 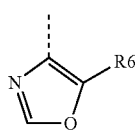
B-39 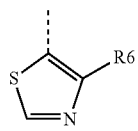
B-40 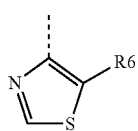
B-41 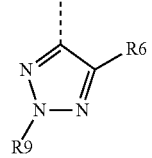
B-42 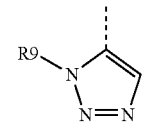
B-43 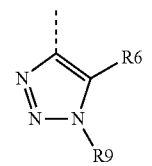
B-44 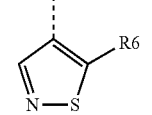
B-45 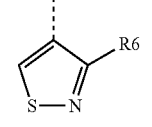
B-46 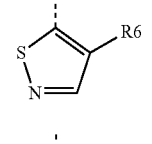
B-47 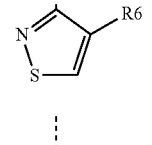
B-48 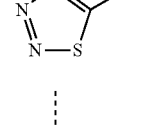
B-49 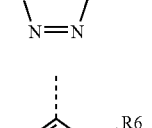
B-50 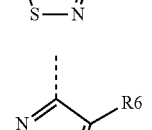
B-51

B-52

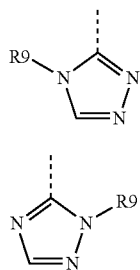

B-53 in which the broken line denotes the bond to D and where B additionally bears n R7 substituents, Z is oxygen or sulphur, R1 is a radical from the group of hydrogen (but only in the case of the combination of A-1 with Q-2), halogen, cyano, nitro, amino, hydroxyl, optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)aminocarbonyl, aminothiocarbonyl, $C_1$-$C_6$-alkylaminosulphonyl, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, aryl, aryloxy, arylthio, heteroaryl, heteroaryloxy and heteroarylthio, R2 is a radical from the group of halogen, cyano, nitro, amino, hydroxyl, optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, aryl, aryloxy, arylthio, heteroaryl, heteroaryloxy and heteroarylthio, R3 is a radical from the group of hydrogen, halogen, cyano, nitro, amino, hydroxyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-haloalkyl, $C_1$-$C_6$-haloalkoxy, $C_1$-$C_6$-haloalkylthio, $C_1$-$C_6$-haloalkylsulphinyl and $C_1$-$C_6$-haloalkylsulphonyl, R4 is a radical from the group of hydrogen, halogen, cyano, nitro, amino, hydroxyl, $C_1$-$C_6$-alkyl, $C_1$-$C_6$-alkoxy, $C_1$-$C_6$-haloalkyl and $C_1$-$C_6$-haloalkoxy, R5 is a radical from the group of hydrogen, $C_1$-$C_6$-alkyl, $C_3$-$C_6$-cycloalkyl, $C_1$-$C_6$-haloalkyl, $C_2$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl, $C_1$-$C_6$-haloalkylsulphonyl and C(=O)—B, R6 is a radical from the group of halogen, cyano, nitro, amino, hydroxyl, in each case optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenyloxy, $C_3$-$C_6$-alkynyloxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, $C_4$-$C_{12}$-bicycloalkyl, aryl, aryloxy, heteroaryl and heteroaryloxy, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, R7 is a radical from the group of halogen, nitro, cyano, amino, hydroxyl, in each case optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, $C_4$-$C_{12}$-bicycloalkyl, aryl, aryloxy, heteroaryl and heteroaryloxy, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, R9 is a radical from the group of hydrogen, $C_1$-$C_6$-alkyl, $C_3$-$C_6$-cycloalkyl, haloalkyl, $C_3$-$C_6$-alkenyl, $C_2$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl, m is a number from the group of 0, 1, 2, 3 and 4, where, when m>1, the R2 radicals may be the same or different, and n is a number from the group of 0, 1, 2 and 3, where, when n>1, the R7 radicals may be the same or different, excluding the compound of the formula

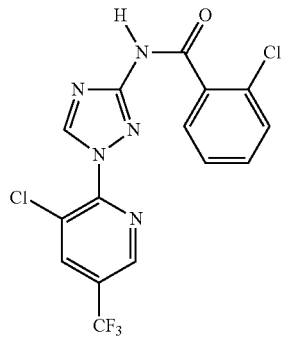 [SMILES: O=C(Nc1ncn(-c2ncc(C(F)(F)F)cc2Cl)n1)c1ccccc1Cl]

It has been found that compounds of the formula (I) have pronounced biological properties and are suitable especially for controlling animal pests, in particular insects, arachnids and nematodes, encountered in agriculture, in forests, in the protection of stored products and materials, in animal health and in the hygiene sector.

DETAILED DESCRIPTION OF A PREFERRED EMBODIMENT

Preferred substituents or ranges for the radicals shown in the compounds of the formula (I) are illustrated below. The combination thereof forms the area of preference (1).

A is a radical from the group of

A-1
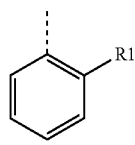

A-2
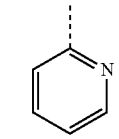

A-3
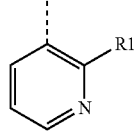

A-4
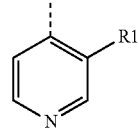

A-5
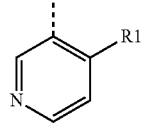

A-6
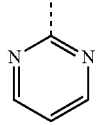

A-7
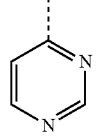

A-8
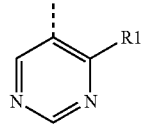

A-9
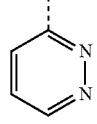

A-10
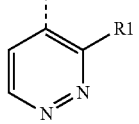

A-11
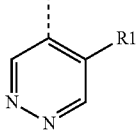

A-12
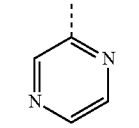

in which the broken line denotes the bond to Q and where A additionally bears m R2 substituents.

Q is a radical from the group of
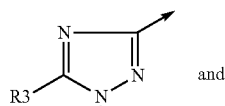
Q-1
and
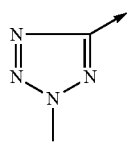
Q-2
in which the nitrogen is joined to the ring A and the arrow in each case denotes the bond to D.
D is the radical of the formula
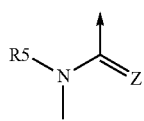
in which the nitrogen is bonded to Q and the arrow denotes the bond to B.
B is a radical from the group of
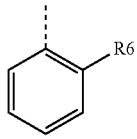
B-1
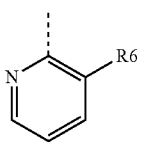
B-2
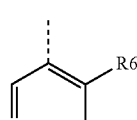
B-3
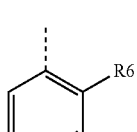
B-4
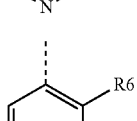
B-5
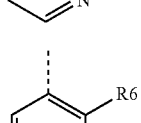
B-6
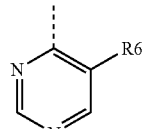
B-7
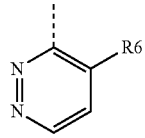
B-8
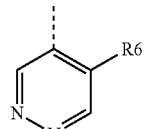
B-9
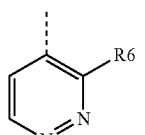
B-10
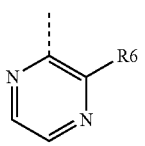
B-11
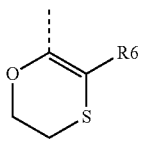
B-12
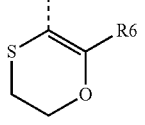
B-13
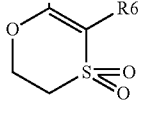
B-14
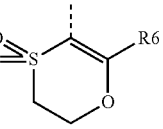
B-15
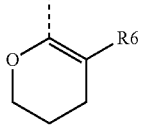
B-16

B-17 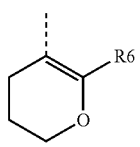
B-18 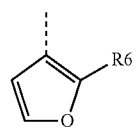
B-19 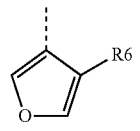
B-20 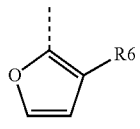
B-21 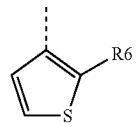
B-22 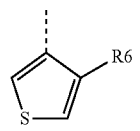
B-23 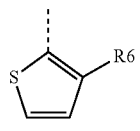
B-24 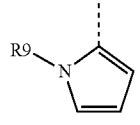
B-25 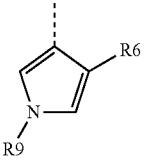
B-26 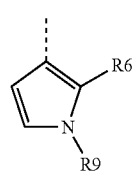
B-27 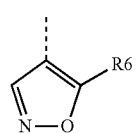
B-28 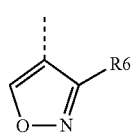
B-29 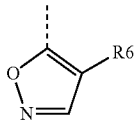
B-30 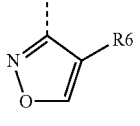
B-31 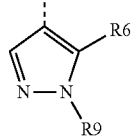
B-32 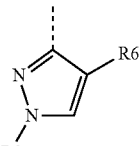
B-33 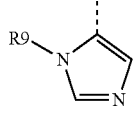
B-34 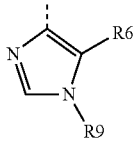
B-35 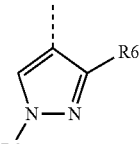
B-36 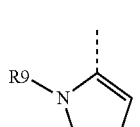
B-37 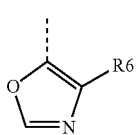

-continued

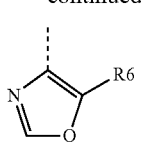
B-38

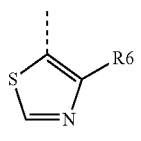
B-39

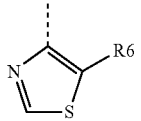
B-40

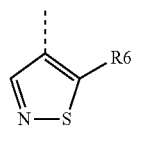
B-44

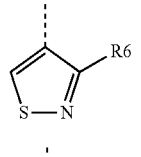
B-45

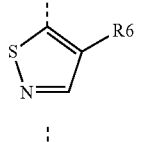
B-46

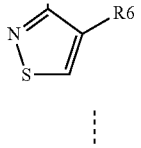
B-47

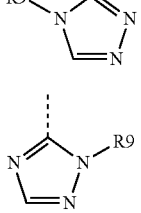
B-52

B-53 in which the broken line denotes the bond to D and where B additionally bears n R7 substituents.

Z is oxygen or sulphur.

R1 is a radical from the group of hydrogen (but only in the case of the combination of A-1 with Q-2), halogen, cyano, nitro, amino, hydroxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, heteroaryl and heteroaryloxy.

R2 is a radical from the group of halogen, cyano, nitro, amino, hydroxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_3$-$C_6$-halocycloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, heteroaryl and heteroaryloxy.

R3 is a radical from the group of hydrogen, halogen, cyano, nitro, amino, hydroxyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-haloalkyl, $C_1$-$C_6$-haloalkoxy, $C_1$-$C_6$-haloalkylthio, $C_1$-$C_6$-haloalkylsulphinyl and $C_1$-$C_6$-haloalkylsulphonyl.

R5 is a radical from the group of hydrogen, $C_1$-$C_6$-alkyl, $C_3$-$C_6$-cycloalkyl, $C_1$-$C_6$-haloalkyl, $C_2$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl, $C_1$-$C_6$-haloalkylsulphonyl and C(=O)—B.

R6 is a radical from the group of halogen, cyano, nitro, amino, hydroxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_3$-$C_6$-alkenylcarbonylamino, $C_3$-$C_6$-alkynylcarbonylamino, $C_3$-$C_6$-cycloalkylcarbonylamino, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, heteroaryl and heteroaryloxy.

R7 is a radical from the group of halogen, cyano, nitro, amino, hydroxyl, $C_1$-$C_6$-alkyl, $C_1$-$C_6$-haloalkyl, cyano- $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_3$-$C_6$-alkenylcarbonylamino, $C_3$-$C_6$-alkynylcarbonylamino, $C_3$-$C_6$-cycloalkylcarbonylamino, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, heteroaryl and heteroaryloxy.

R9 is a radical from the group of hydrogen, $C_1$-$C_6$-alkyl, $C_3$-$C_6$-cycloalkyl, $C_1$-$C_6$-haloalkyl, $C_3$-$C_6$-alkenyl, $C_2$-$C_6$-alkynyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl.

m is a number from the group of 0, 1, 2, 3 and 4, where, when m>1, the R2 radicals may be the same or different.

n is a number from the group of 0, 1, 2 and 3, where, when n>1, the R7 radicals may be the same or different.

Particularly preferred substituents or ranges for the radicals shown in the compounds of the formula (I) are illustrated below. The combination thereof forms the area of preference (2).

A is a radical from the group of

A-1

A-2

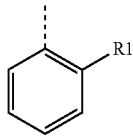

A-3

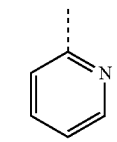

A-4

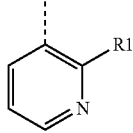

A-5

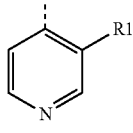

-continued

A-6

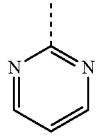

A-7

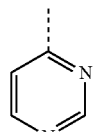

A-8

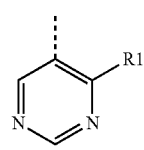

A-9

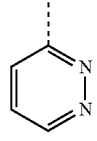

A-10

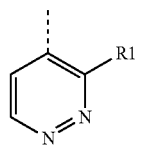

A-11

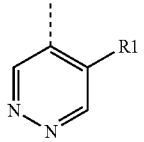

A-12

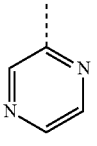

in which the broken line denotes the bond to Q and where A additionally bears m R2 substituents.

Q is a radical from the group of

Q-1

 and

Q-2

in which the nitrogen is joined to the ring A and the arrow in each case denotes the bond to D.

D is the radical of the formula
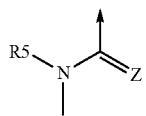
in which the nitrogen is bonded to Q and the arrow denotes the bond to B.
B is a radical from the group of
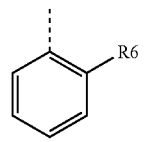
B-1
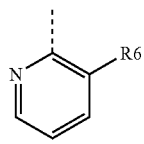
B-2
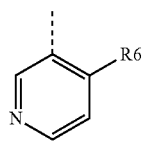
B-3
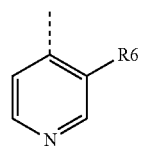
B-4
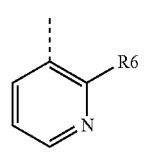
B-5
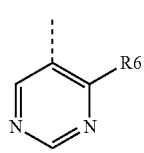
B-6
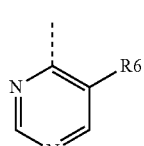
B-7
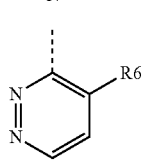
B-8
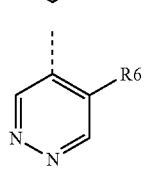
B-9
-continued
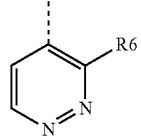
B-10
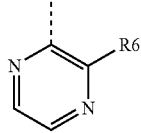
B-11
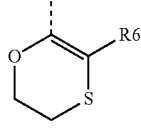
B-12
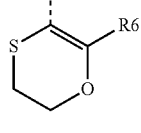
B-13
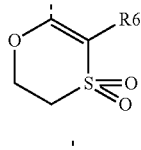
B-14
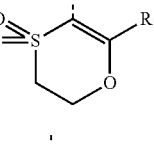
B-15
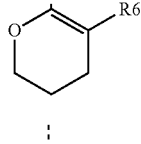
B-16
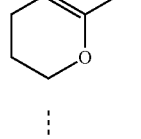
B-17
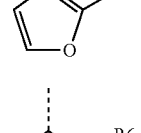
B-18
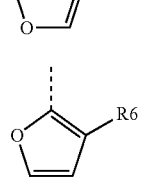
B-19
B-20

-continued

B-21 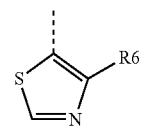

B-22 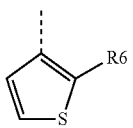

B-23 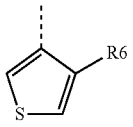

B-31 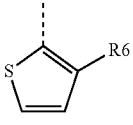

B-32 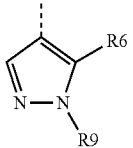

B-33 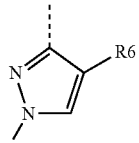

B-34 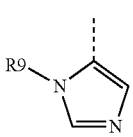

B-35 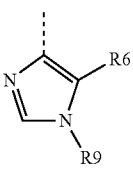

B-36 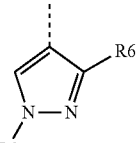

B-37 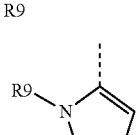

B-38 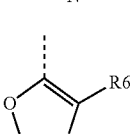

B-39 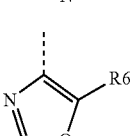

B-40 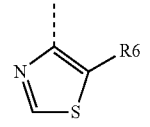

B-52 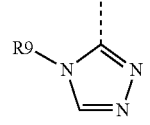

B-53 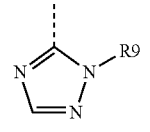

in which the broken line denotes the bond to D and where B additionally bears n R7 substituents.

Z is oxygen or sulphur.

R1 is a radical from the group of hydrogen (but only in the case of the combination of A-1 with Q-2), halogen, cyano, nitro, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, aryloxy, heteroaryl and heteroaryloxy.

R2 is a radical from the group of halogen, cyano, nitro, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkoxyimino-$C_1$-$C_6$-alkyl, aryl, aryloxy, heteroaryl and heteroaryloxy.

R3 is a radical from the group of hydrogen, halogen, cyano, nitro, amino, hydroxyl, $C_1$-$C_6$-alkyl and $C_1$-$C_6$-haloalkyl.

R5 is a radical from the group of hydrogen, $C_1$-$C_6$-alkyl, $C_3$-$C_6$-cycloalkyl, $C_1$-$C_6$-haloalkyl, $C_2$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl, $C_1$-$C_6$-haloalkylsulphonyl and C(=O)—B.

R6 is a radical from the group of halogen, cyano, nitro, hydroxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, aryloxy, heteroaryl and heteroaryloxy.

R7 is a radical from the group of halogen, cyano, nitro, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, aryloxy, heteroaryl and heteroaryloxy.

R9 is a radical from the group of hydrogen, $C_1$-$C_6$-alkyl, $C_3$-$C_6$-cycloalkyl and $C_1$-$C_6$-haloalkyl.

m is a number from the group of 0, 1, 2, 3 and 4, where, when m>1, the R2 radicals may be the same or different.

n is a number from the group of 0, 1 and 2, where, when n>1, the R7 radicals may be the same or different.

Very particularly preferred substituents or ranges of the radicals shown in the compounds of the formula (I) are elucidated below. The combination thereof forms the area of preference (3).

A is a radical from the group of

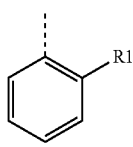
A-1

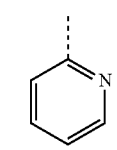
A-2

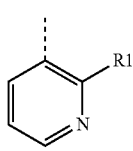
A-3

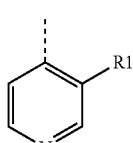
A-4

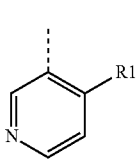
A-5

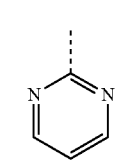
A-6

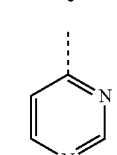
A-7

-continued

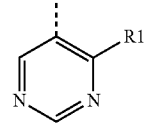
A-8

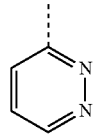
A-9

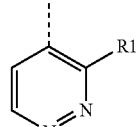
A-10

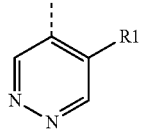
A-11

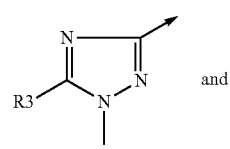
A-12

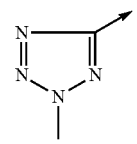

in which the broken line denotes the bond to Q and where A additionally bears m R2 substituents.

Q is a radical from the group of

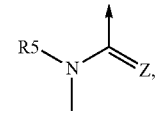
Q-1
and

Q-2 in which the nitrogen is joined to the ring A and the arrow in each case denotes the bond to D.

D is the radical of the formula in which the nitrogen is bonded to Q and the arrow denotes the bond to B.

B is a radical from the group of
B-1
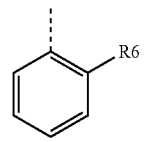
B-2
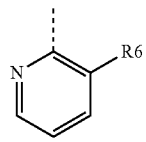
B-3
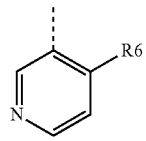
B-4
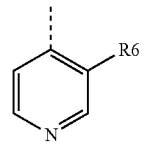
B-5
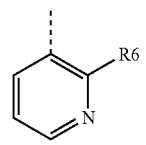
B-6
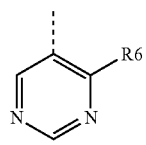
B-7
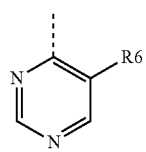
B-8
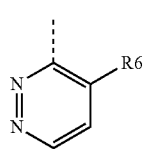
B-9
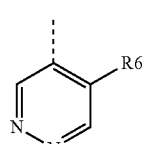
B-10
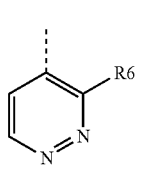
-continued
B-11
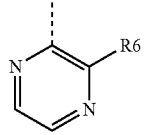
B-13
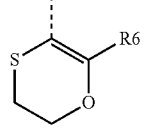
B-18
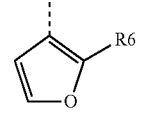
B-19
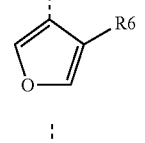
B-20
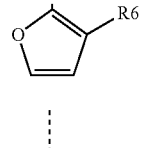
B-21
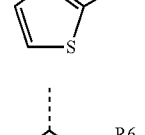
B-22
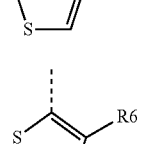
B-23
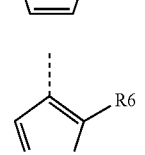
B-31
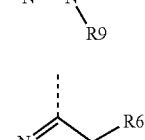
B-32
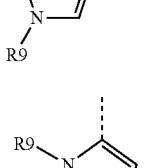
B-33

-continued

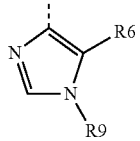
B-34

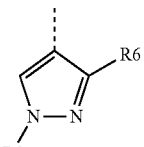
B-35

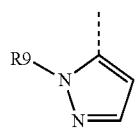
B-36

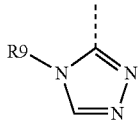
B-52

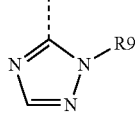
B-53 in which the broken line denotes the bond to D and where B additionally bears n R7 substituents.

Z is oxygen or sulphur.

R1 is a radical from the group of hydrogen (but only in the case of the combination of A-1 with Q-2), halogen, cyano, nitro, $C_1$-$C_4$-alkyl, $C_1$-$C_4$-haloalkyl, $C_1$-$C_4$-alkoxy, $C_1$-$C_4$-haloalkoxy and $C_1$-$C_4$-alkylsulphonyl.

R2 is a radical from the group of halogen, $C_1$-$C_4$-alkyl, $C_1$-$C_4$-haloalkyl, $C_1$-$C_4$-alkoxy, $C_1$-$C_4$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl and $C_1$-$C_6$-haloalkylsulphonyl.

R3 is a radical from the group of hydrogen, halogen, $C_1$-$C_4$-alkyl, $C_1$-$C_4$-haloalkyl.

R5 is a radical from the group of hydrogen, $C_1$-$C_4$-alkyl, $C_3$-$C_4$-alkenyl, $C_3$-$C_4$-alkynyl, $C_3$-$C_6$-cycloalkyl-$C_1$-$C_4$-alkyl, $C_1$-$C_4$-alkylcarbonyl, cyano-$C_1$-$C_4$-alkyl and C(=O)—B.

R6 is a radical from the group of halogen, nitro, hydroxyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphonyl and heteroaryl.

R7 is a radical from the group of halogen, $C_1$-$C_4$-alkyl and $C_1$-$C_4$-haloalkyl.

R9 is $C_1$-$C_4$-alkyl.

m is a number from the group of 0, 1, 2, 3 and 4, where, when m>1, the R2 radicals may be the same or different.

n is a number from the group of 0 and 1.

A further group of preferred compounds of the formula (I) is that of those in which A is a radical from the group of

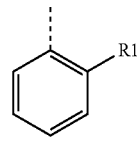
A-1

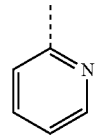
A-2 in which the broken line denotes the bond to Q and where A additionally bears m R2 substituents, Q is a radical from the group of

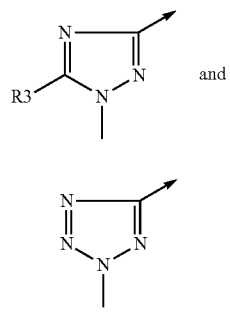
Q-1 and

Q-2 in which the nitrogen is joined to the ring A and the arrow in each case denotes the bond to D, D is the radical of the formula

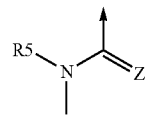

in which the nitrogen is bonded to Q and the arrow denotes the bond to B,

B is a radical from the group of

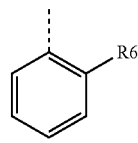
B-1

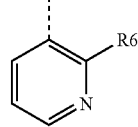
B-5

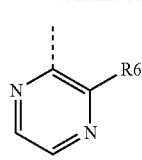

B-11 in which the broken line denotes the bond to D and where B additionally bears n R7 substituents, Z is oxygen, R1 is a radical from the group of halogen, $C_1$-$C_4$-alkyl, $C_1$-$C_4$-haloalkyl, $C_1$-$C_4$-alkoxy and $C_1$-$C_4$-haloalkoxy, R2 is a radical from the group of halogen, $C_1$-$C_4$-alkyl, $C_1$-$C_4$-haloalkyl, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl and $C_1$-$C_6$-haloalkylsulphonyl, R3 is hydrogen, R5 is hydrogen, R6 is a radical from the group of halogen, nitro, $C_1$-$C_4$-alkyl, $C_1$-$C_4$-haloalkyl and $C_1$-$C_4$-haloalkoxy, R7 is halogen, m is a number from the group of 0, 1, 2, 3 and 4, where, when m>1, the R2 radicals may be the same or different, and n is a number from the group of 0 and 1.

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (synonymous with heteroaryl, including as part of a larger unit, for example heteroaryloxy) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl and pyrazinyl.

In the particularly preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, het(ero)aryl (including as part of a larger unit, for example heteroaryloxy) is selected from the group of furyl, thienyl, pyrrolyl, pyrazolyl, imidazolyl, oxadiazolyl, 1,2,3-triazolyl, 1,2,4-triazolyl, oxazolyl, isoxazolyl and thiazolyl.

In the very particularly preferred definitions, unless stated otherwise, halogen is selected from the group of fluorine, chlorine, bromine and iodine, preferably in turn from the group of fluorine, chlorine and bromine, and het(ero)aryl (including as part of a larger unit, for example heteroaryloxy) is 1,2,4-triazolyl.

Halogen-substituted radicals, for example haloalkyl, are mono- or polyhalogenated up to the maximum possible number of substituents. In the case of polyhalogenation, the halogen atoms may be the same or different. Halogen is fluorine, chlorine, bromine and iodine, especially fluorine, chlorine and bromine.

The maximum possible values of m and n are naturally dependent on the number of bonding sites in the A and B radicals.

Saturated or unsaturated hydrocarbon radicals, such as alkyl or alkenyl, may each be straight-chain or branched if possible, including in combination with heteroatoms, as, for example, in alkoxy.

Unless indicated otherwise, optionally substituted radicals may be mono- or polysubstituted, where the substituents in the case of poly substitutions may be the same or different.

The radical definitions or elucidations given in general terms or within areas of preference apply correspondingly to end products, starting materials and intermediates specified above and hereinafter. These radical definitions can be combined with one another as desired, i.e. including combinations between the respective preferred ranges.

Preference is given in accordance with the invention to compounds of the formula (I) in which a combination of the definitions listed above as preferred is present (area of preference (1)).

Particular preference is given in accordance with the invention to compounds of the formula (I) in which a combination of the definitions listed above as particularly preferred is present (area of preference (2)).

Very particular preference is given in accordance with the invention to compounds of the formula (I) in which a combination of the definitions listed above as very particularly preferred is present (area of preference (3)).

In the groups of compounds below, the R1 to R7 and Z radicals are each as defined above.

In a particular group of inventive compounds of the formula (I), Q is Q-1

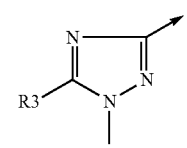

Q-1 which gives, taking account of the definition of D, compounds of the formula (I-1)

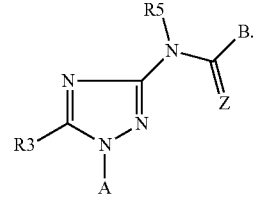

(I-1)

Preference is further given to compounds defined by the area of preference (1) in which Q is Q-1.

Preference is further given to compounds defined by the area of preference (2) in which Q is Q-1.

Preference is further given to compounds defined by the area of preference (3) in which Q is Q-1.

In a further particular group of inventive compounds of the formula (I), Q is Q-2

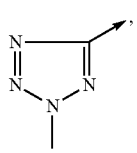
Q-2 which gives, taking account of the definition of D, compounds of the formula (I-2)

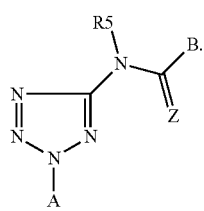
(I-2)

Preference is further given to compounds defined by the area of preference (1) in which Q is Q-2.

Preference is further given to compounds defined by the area of preference (2) in which Q is Q-2.

Preference is further given to compounds defined by the area of preference (3) in which Q is Q-2.

In a further particular group of inventive compounds of the formula (I), A is A-1

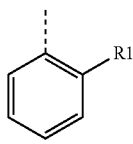

where this radical bears m R2 substituents.

Preference is further given to compounds defined by the area of preference (1) in which A is A-1.

Preference is further given to compounds defined by the area of preference (2) in which A is A-1.

Preference is further given to compounds defined by the area of preference (3) in which A is A-1.

In a further particular group of inventive compounds of the formula (I), A is A-2

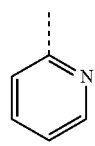

where this radical bears m R2 substituents.

Preference is further given to compounds defined by the area of preference (1) in which A is A-2.

Preference is further given to compounds defined by the area of preference (2) in which A is A-2.

Preference is further given to compounds defined by the area of preference (3) in which A is A-2.

In a further particular group of inventive compounds of the formula (I), A is A-6

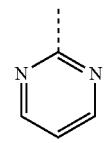

where this radical bears m R2 substituents.

Preference is further given to compounds defined by the area of preference (1) in which A is A-6.

Preference is further given to compounds defined by the area of preference (2) in which A is A-6.

Preference is further given to compounds defined by the area of preference (3) in which A is A-6.

In the particular groups (G-1) to (G-8) of compounds of the formula (I) which follow, each of which constitutes a preferred embodiment, the A and B radicals may respectively bear further R2 and R7 substituents as detailed above.

A particular group G-1 of compounds of the formula (I) is of compounds of the formula (A-1)-(Q-1)-D-(B-1)

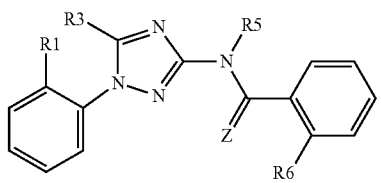
G-1

Within the group G-1, preference is given in turn to those compounds in which R3 and R5 are each hydrogen and Z is oxygen.

A further particular group G-2 of compounds of the formula (I) is of compounds of the formula (A-2)-(Q-1)-D-(B-1)

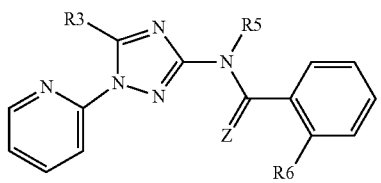
G-2

Within the group G-2, preference is given in turn to those compounds in which R3 and R5 are each hydrogen and Z is oxygen.

A further particular group G-3 of compounds of the formula (I) is of compounds of the formula (A-1)-(Q-1)-D-(B-5)

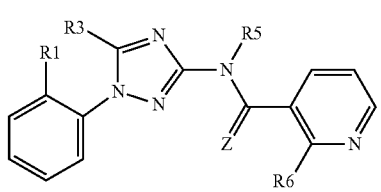
G-3

Within the group G-3, preference is given in turn to those compounds in which R3 and R5 are each hydrogen and Z is oxygen.

A further particular group G-4 of compounds of the formula (I) is of compounds of the formula (A-1)-(Q-1)-D-(B-11).

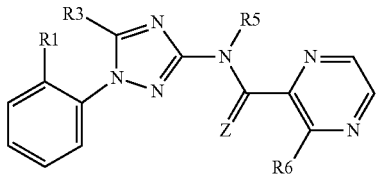
G-4

Within the group G-4, preference is given in turn to those compounds in which R3 and R5 are each hydrogen and Z is oxygen.

A further particular group G-5 of compounds of the formula (I) is of compounds of the formula (A-1)-(Q-2)-D-(B-1).

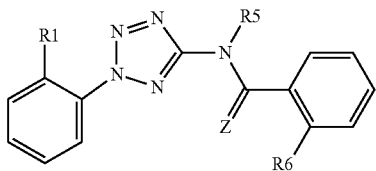
G-5

Within the group G-5, preference is given in turn to those compounds in which R5 is hydrogen and Z is oxygen.

A further particular group G-6 of compounds of the formula (I) is of compounds of the formula (A-2)-(Q-2)-D-(B-1).

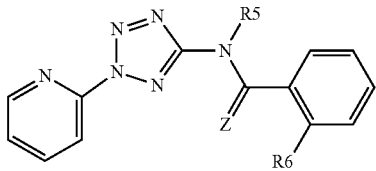
G-6

Within the group G-6, preference is given in turn to those compounds in which R5 is hydrogen and Z is oxygen.

A further particular group G-7 of compounds of the formula (I) is of compounds of the formula (A-1)-(Q-2)-D-(B-5).

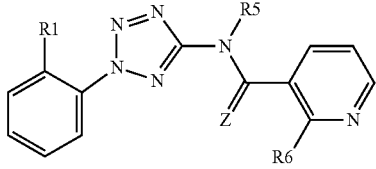
G-7

Within the group G-7, preference is given in turn to those compounds in which R5 is hydrogen and Z is oxygen.

A further particular group G-8 of compounds of the formula (I) is of compounds of the formula (A-1)-(Q-2)-D-(B-11).

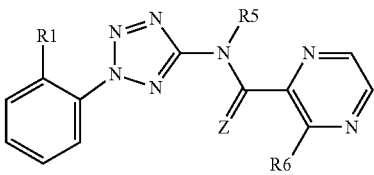
G-8

Within the group G-8, preference is given in turn to those compounds in which R5 is hydrogen and Z is oxygen.

It has additionally been found that the compounds of the formula (I) can be obtained by the processes described below.

Accordingly, the invention also relates to processes for preparing compounds of the formula (I) in which Z is O, by reacting amines of the formulae (II-1), (III-2) and (II-3)

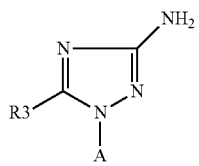
(II-1)

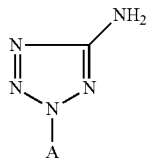
(II-2)

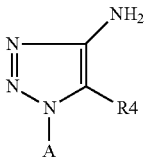
(III-2)

with compounds of the formula (III)

(III)

in which
M is halogen, alkoxy, alkylsulphanyl, acyloxy, sulphonyloxy, N-heterocyclyl (e.g. imidazolyl) or hydroxyl,
B is as defined above and
Z is O.

It is possible here for compounds of the formula (III) to have been activated already or to be activated in situ. For example, it is possible to use compounds of the formula (III) as acid halides (e.g. M=chlorine). In that case, the reaction is advantageously conducted in the presence of a base, for example triethylamine or sodium hydroxide. Alternatively, it is also possible to use carboxylic acids (M=OH) in the presence of coupling reagents, for example dicyclohexylcarbodiimide, and additives such as 1-hydroxy-1H-benzotriazole (W. König, R. Geiger, Chem. Ber. 1970, 103, 788). It is additionally possible to use coupling reagents such as 1-ethyl-3-(3-dimethylaminopropyl)carbodiimide, 1,1'-carbonyl-1H-imidazole, O-(benzotriazol-1-yl)-N,N,N',N'-tetramethyluronium hexafluorophosphate and similar compounds. Suitable coupling reagents for performance of the preparation process are in principle all compounds that enable the formation of an amide bond (cf., for example, E. Valeur, M. Bradley, *Chem. Soc. Rev.* 2009, 38, 606; S.-Y. Han, Y.-A. Kim, *Tetrahedron* 2004, 60, 2447). In addition, it is also possible to use symmetric or mixed anhydrides for preparation of compounds of the formula (I) (G. W. Anderson, J. E. Zimmerman, F. M. Calahan, *J. Am. Chem. Soc.* 1967, 89, 5012). It is possible here to use various chloroformic esters, for example iso-butyl chloroformate and sec-butyl chloroformate. It is likewise possible to use, for example, isovaleryl chloride and pivaloyl chloride.

Amines of the formula (II-1)

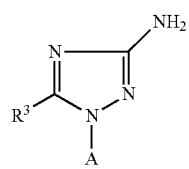

are commercially available or known from the literature, or they can be synthesized by processes known from the literature. See, for example, WO 2012/006473, U.S. Pat. No. 6,083,965 (2000), Anales de Quimica 70, 986 (1974), J. Het. Chem. 8, 137-139 (1971), US 2010/120874, Gazz. Chimica Italiana 29, 105 (1899), J. Chem. Soc. Perkin Trans 1, 81-85 (1974), Arch. Pharm. 322, 583-587 (1989), Synthesis 45, 1093 (2013).

Novel compounds, which also form part of the subject-matter of the invention, are compounds of the formula (IIa-1-a)

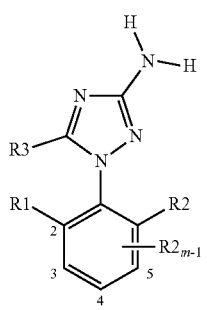

in which R1 and R2 are each as defined above and m is a number from the group of 1, 2 and 3.

Compounds of the formula (I-1) can also be prepared by rearrangement of N-(5-aryl-1,2,4-oxadiazol-3-yl)-N'-aryl-formamidines as follows:

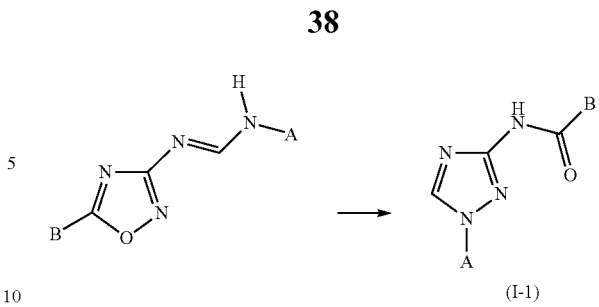

See, for example, J. Chem. Soc. Perkin Trans. 2 1339-1343 (1993), Tetrahedron 50, 7315-7326 (1994), J. Het. Chem. 8, 137-139 (1971), K. H. Baumann US 2010/120874.

The compounds of the formula (I-1) are also obtained by reaction of alkyl [5-aryl-1,2,4-oxadiazol-3-yl]imidoformates with appropriately substituted anilines (cf. J. Het. Chem. 8, 137-139 (1971)):

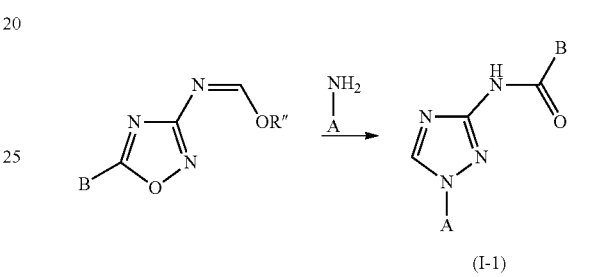

The compounds of the formula (I-1) are also obtained by rearrangement of N-(4-aryl-1,2,5-oxadiazol-3-yl)-N'-aryl-formamidines (cf. J. Chem. Soc. Perkin Trans 1, 589-591 (1977)):

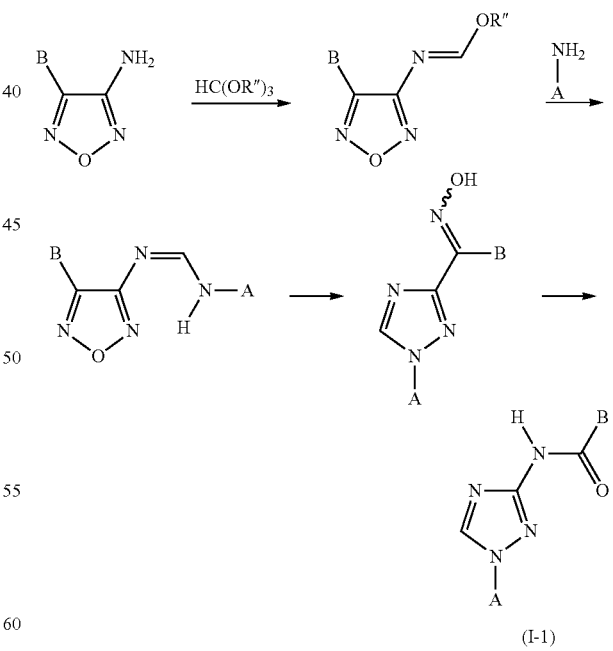

The aminooxadiazoles used as reactants in this synthesis sequence are commercially available or can be prepared by methods known from the literature. See, for example, WO 2009/0011850, Heterocycles 57, 811 (2002), WO 2011/132017, J. Med. Chem. 23, 690-692 (1980), Heterocycles 34, 2313-2322 (1992), Tetrahedron 57, 5865-5871 (2001), J. Chem. Soc. Perkin Trans 1, 1313 (1988), Z. Chem. 14, 94 (1974).

The synthesis of inventive compounds (for better clarity, possible R2, R3 and R7 radicals are not shown) is shown by way of example in Synthesis Scheme 1 with regard to the preparation of the compounds of the formula (Ia-1) (see also the preparation examples).

Synthesis Scheme 1:

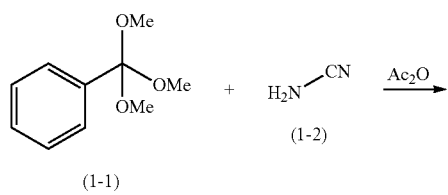

(1-1) + (1-2) → Ac₂O

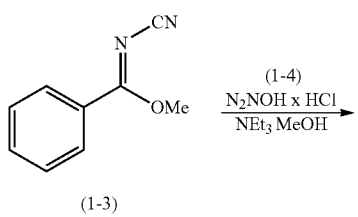

(1-3) → N₂NOH x HCl / NEt₃ MeOH (1-4)

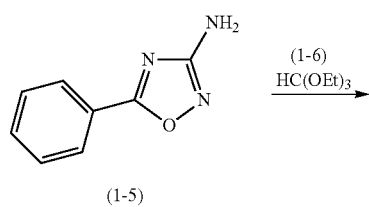

(1-5) → HC(OEt)₃ (1-6)

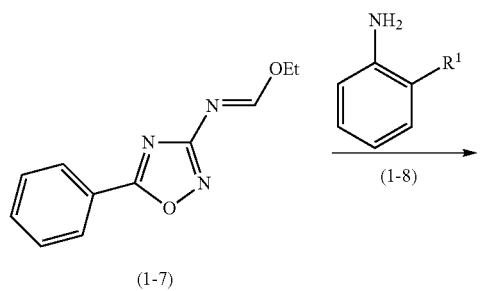

(1-7) + (1-8)

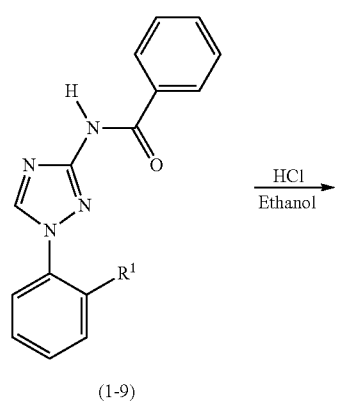

(1-9) → HCl / Ethanol

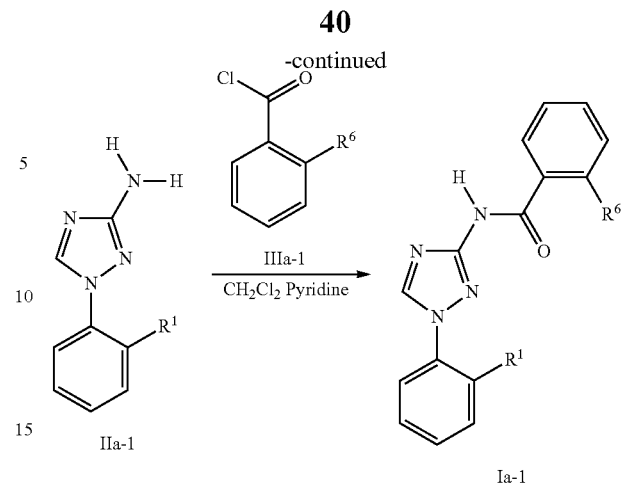

IIa-1 → IIIa-1 / CH₂Cl₂ Pyridine → Ia-1

The 3-benzamido-1-aryl-1,2,4-triazoles (1-9) synthesized in this way are novel and also form part of the subject-matter of the invention.

Proceeding from substituted 3-amino-5-aryl-1,2,4-oxadiazoles of the formula (2-6), which can be prepared with the aid of methods known from the literature (cf. Heterocycles, 57, 811-823), it is possible to prepare the compounds of the formula (Ia-1) by reaction of appropriately substituted alkyl [5-aryl-1,2,4-oxadiazol-3-yl-]imidoformates of the formula (2-8) with anilines of the formula (2-9) according to Synthesis Scheme 2.

Synthesis Scheme 2:

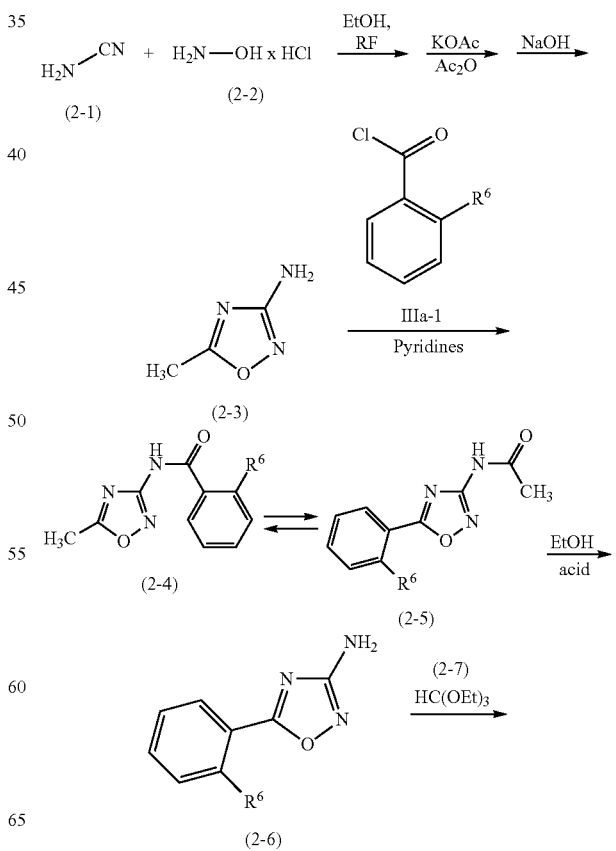

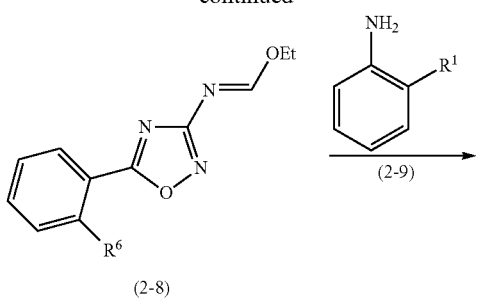

(2-8)

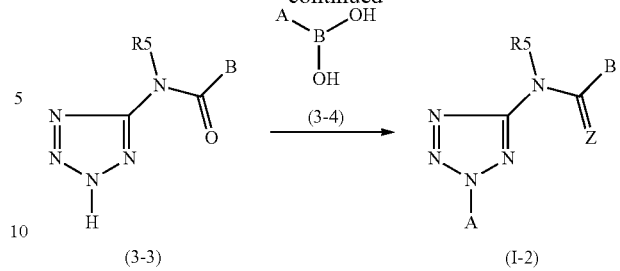

(3-3)     (I-2)

Aminotetrazoles of the formula (3-1) can be reacted with a carbonyl chloride of the formula (3-2) to give an amide having the structure (3-3). The reaction of 2H-tetrazoles of the formula (3-3) with boronic acids of the formula (3-4) in the presence of copper(II) compounds (e.g. copper(II) acetate and pyridine; cf. *Tetrahedron* 1998, 39, 2941) gives compounds of the formula (I-2).

Some amines of the formula (II-2)

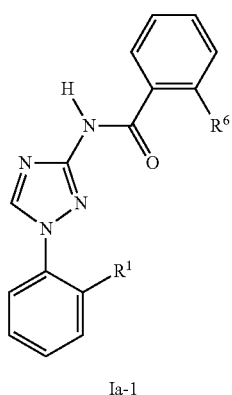

Ia-1

Compounds of the formula (I) in which Z is O (oxygen atom) can be reacted with a thionating reagent, for example diphosphorus pentasulphide or Lawesson's reagent (cf. C. P. Dell in *Comprehensive Organic Functional Group Transformations*, vol. 5, eds.: A. L. Katritzky, O. Meth-Cohn, C. W. Rees, Pergamon, Oxford, 1995, p. 565; Synthesis 2003, 13, 1929), to give compounds of the formula (I) in which Z is S (sulphur atom).

Compounds of the formula (I-2)

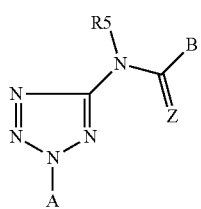

(I-2)

can also be obtained via Synthesis Scheme 3:

Synthesis Scheme 3:

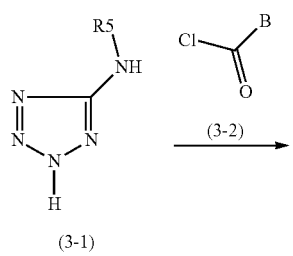

(3-1)

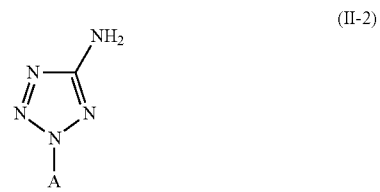

are commercially available. One example is 2-phenyl-2H-tetrazol-5-amine.

Novel amines of the formula (II-2) can be obtained according to Synthesis Scheme 4:

Synthesis Scheme 4:

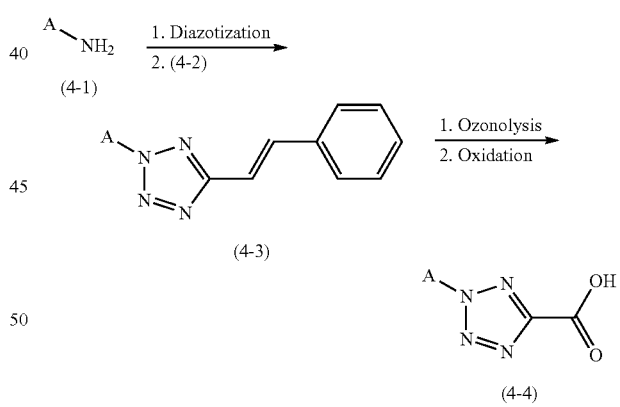

Aromatic anilines of the formula (4-1) can be diazotized in a first step, for example with sodium nitrite in hydrochloric acid, and then cyclized with a tosyl hydrazone, for example (4-2) of the formula

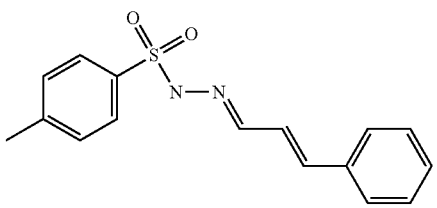

(4-2)

in the presence of pyridine to give the tetrazole of the formula (4-3) (cf. J. Med. Chem. 2000, 43, 953). After ozonolysis and subsequent oxidation (for example with sodium chromate(VI), cf. Comprehensive Organic Transformations: A Guide to Functional Group Preparations; Larock, R. C., Ed.; Wiley-VCH: New York, 1999), the compound of the formula (4-3) gives the carboxylic acid of the formula (4-4), which can be converted by Curtius degradation to the 5-aminotetrazole of the formula (II-2) (cf. Org. React. 1946, 337).

The processes according to the invention for preparation of the novel compounds of the formula (I) are preferably performed using a diluent. Useful diluents for performance of the processes according to the invention are, as well as water, all inert solvents. Examples include: halohydrocarbons (for example chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (for example methanol, ethanol, isopropanol, butanol), ethers (for example ethyl propyl ether, methyl tert-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, 1,4-dioxane, dichlorodiethyl ether and polyethers of ethylene oxide and/or propylene oxide), amines (for example trimethyl-, triethyl-, tripropyl-, tributylamine, N-methylmorpholine, pyridine and tetramethylenediamine), nitrohydrocarbons (for example nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (for example dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (for example pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, benzene, toluene, xylene, esters (for example methyl, ethyl, butyl and isobutyl acetate, dimethyl, dibutyl and ethylene carbonate); amides (for example hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (for example acetone, acetophenone, methyl ethyl ketone, methyl butyl ketone).

It is of course also possible to perform the process according to the invention in mixtures of the solvents and diluents mentioned.

When performing the process according to the invention, the reaction temperatures can be varied within a relatively wide range. In general, temperatures between −30° C. and +150° C., preferably between −10° C. and +100° C., are employed.

The process according to the invention is generally performed under atmospheric pressure. However, it is also possible to perform the process according to the invention under elevated or reduced pressure—generally at absolute pressures between 0.1 bar and 15 bar.

To perform the process according to the invention, the starting materials are generally used in approximately equimolar amounts. However, it is also possible to use one of the components in a relatively large excess. The reaction is generally carried out in a suitable diluent in the presence of a reaction auxiliary, optionally also under a protective gas atmosphere (for example under nitrogen, argon or helium) and the reaction mixture is generally stirred at the temperature required for several hours. The workup is performed by customary methods (cf. the preparation examples).

The basic reaction auxiliaries used to perform the processes according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, 2-picoline, 3-picoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethyldiamine).

Acidic reaction auxiliaries used to perform the processes according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. The invention thus encompasses pure stereoisomers and any desired mixtures of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always comprises the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are effective against normally sensitive and resistant species and against all or some stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici*;

from the class of the Chilopoda, for example *Geophilus* spp., *Scutigera* spp.;

from the order or the class of the Collembola, for example *Onychiurus armatus; Sminthurus viridis*;

from the class of the Diplopoda, for example *Blaniulus guttulatus*;

from the class of the Insecta, for example from the order of the Blattodea, for example *Blatta orientalis, Blattella asahinai, Blattella germanica, Leucophaea maderae, Panchlora* spp., *Parcoblatta* spp., *Periplaneta* spp., for example *Periplaneta americana, Periplaneta australasiae, Supella longipalpa*;

from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus*

*truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides*;

from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex*;

from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni (=Parthenolecanium corni), Lepidosaphes* spp., for example *Lepidosaphes ulmi, Lipaphis erysimi, Lycorma delicatura, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Nephotettix* spp., for example *Nephotettix cincticeps, Nephotettix nigropictus, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campyloma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Linepithema humile, Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci;* from the order of the Zygentoma (=*Thy sanura*), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, for example from the class of the Bivalvia, for example *Dreissena* spp.;

and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp, *Ancylostoma* spp, *Angiostrongylus* spp., *Anisakis* spp., *Anoplocephala* spp., *Ascaris* spp., *Ascaridia* spp., *Baylisascaris* spp., *Brugia* spp., *Bunosto-*

*mum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, especially *Aglenchus* spp., for example *Aglenchus agricola*, *Anguina* spp., for example *Anguina tritici*, *Aphelenchoides* spp., for example *Aphelenchoides arachidis*, *Aphelenchoides fragariae*, *Belonolaimus* spp., for example *Belonolaimus gracilis*, *Belonolaimus longicaudatus*, *Belonolaimus nortoni*, *Bursaphelenchus* spp., for example *Bursaphelenchus cocophilus*, *Bursaphelenchus eremus*, *Bursaphelenchus xylophilus*, *Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paraphelenchus* spp., *Paratrichodorus* spp., for example *Paratrichodorus minor*, *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

In addition, it is possible to control, from the sub-kingdom of the Protozoa, the order of the Coccidia, for example *Eimeria* spp.

Nematodes

In the present context, the term "nematodes" comprises all species of the phylum Nematoda and here in particular species that act as parasites on plants or fungi (for example species of the order Aphelenchida, *Meloidogyne*, Tylenchida and others) or else on humans and animals (for example species of the orders Trichinellida, Tylenchida, Rhabditida and Spirurida) or cause damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue.

Here, the efficacy of the compounds is determined by comparing mortalities, gall formation, cyst formation, nematode density per volume of soil, nematode density per root, number of nematode eggs per soil volume, mobility of the nematodes between a plant or plant part treated with the compound of the formula (I) or the treated soil and an untreated plant or plant part or the untreated soil (100%). Preferably, the reduction achieved is 25-50% in comparison to an untreated plant, plant part or the untreated soil, more preferably 51-79% and most preferably the complete kill or the complete prevention of development and growth of the nematodes by a reduction of 80 to 100%. The control of nematodes as described herein also comprises the control of proliferation of the nematodes (development of cysts and/or eggs). Compounds of the formula (I) can likewise be used to maintain the health of the plants or animals, and they can be used for the control of nematodes in a curative, preventative or systemic manner.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; nonmigratory parasites such as *Heterodera* spp., *Globodera* spp. and *Meloidogyne* spp., and also stem and leaf endoparasites such as *Ditylenchus* spp., *Aphelenchoides* spp. and *Hirschmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita*, *Heterodera glycines* (soya bean cyst nematode), *Globodera pallida* and *Globodera rostochiensis* (yellow potato cyst nematode), these species being controlled effectively by the compounds described in the present text. However, the use of the compounds described in the present text is by no means restricted to these genera or species, but also extends in the same manner to other nematodes.

The plant nematodes include, for example, *Aglenchus agricola*, *Anguina tritici*, *Aphelenchoides arachidis*, *Aphelenchoides fragaria*, and the stem and leaf endoparasites *Aphelenchoides* spp., *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus* and *Bursaphelenchus* spp., Cacopaurus *pestis*, *Criconemella curvata*, *Criconemella onoensis*, *Cricone-*

*mella ornata, Criconemella rusium, Criconemella xenoplax* (=*Mesocriconema xenoplax*) and *Criconemella* spp.,

*Criconemoides ferniae, Criconemoides onoense, Criconemoides ornatum* and *Criconemoides* spp., *Ditylenchus destructor, Ditylenchus dipsaci, Ditylenchus myceliophagus* and also the stem and leaf endoparasites *Ditylenchus* spp., *Dolichodorus heterocephalus, Globodera pallida* (=*Heterodera pallida*), *Globodera rostochiensis* (yellow potato cyst nematode), *Globodera solanacearum, Globodera tabacum, Globodera virginia* and the non-migratory cyst-forming parasites *Globodera* spp., *Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp., *Hemicriconemoides, Hemicycliophora arenaria, Hemicycliophora nudata, Hemicycliophora parvana, Heterodera avenae, Heterodera cruciferae, Heterodera glycines* (soya bean cyst nematode), *Heterodera oryzae, Heterodera schachtii, Heterodera zeae* and the non-migratory cyst-forming parasites *Heterodera* spp., *Hirschmaniella gracilis, Hirschmaniella oryzae, Hirschmaniella spinicaudata* and the stem and leaf endoparasites *Hirschmaniella* spp., *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and the ectoparasites *Longidorus* spp., *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne fallax, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne minor, Meloidogyne naasi, Meloidogyne paranaensis, Meloidogyne thamesi* and the non-migratory parasites *Meloidogyne* spp., *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp., *Paratylenchus hamatus, Paratylenchus minutus, Paratylenchus projectus* and *Paratylenchus* spp., *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and the migratory endoparasites *Pratylenchus* spp., *Pseudohalenchus minutus, Psilenchus magnidens, Psilenchus tumidus, Punctodera chalcoensis, Quinisulcius acutus, Radopholus citrophilus, Radopholus similis*, the migratory endoparasites *Radopholus* spp., *Rotylenchulus borealis, Rotylenchulus parvus, Rotylenchulus reniformis* and *Rotylenchulus* spp., *Rotylenchus laurentinus, Rotylenchus macrodoratus, Rotylenchus robustus, Rotylenchus uniformis* and *Rotylenchus* spp., *Scutellonema brachyurum, Scutellonema bradys, Scutellonema clathricaudatum* and the migratory endoparasites *Scutellonema* spp., *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp., *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp., *Tylenchulus semipenetrans* and the semiparasites *Tylenchulus* spp., *Xiphinema americanum, Xiphinema brevicolle, Xiphinema dimorphicaudatum, Xiphinema index* and the ectoparasites *Xiphinema* spp.

Nematodes for the control of which a compound of the formula (I) may be used include nematodes of the genus *Meloidogyne* such as the Southern root-knot nematode (*Meloidogyne incognita*), the Javanese root-knot nematode (*Meloidogyne javanica*), the Northern root-knot nematode (*Meloidogyne hapla*) and the peanut root-knot nematode (*Meloidogyne arenaria*); nematodes of the genus *Ditylenchus* such as the potato rot nematode (*Ditylenchus destructor*) and stem and bulb eelworm (*Ditylenchus dipsaci*); nematodes of the genus *Pratylenchus* such as the cob root-lesion nematode (*Pratylenchus penetrans*), the chrysanthemum root-lesion nematode (*Pratylenchus fallax*), the coffee root nematode (*Pratylenchus coffeae*), the tea root nematode (*Pratylenchus loosi*) and the walnut root-lesion nematode (*Pratylenchus vulnus*); nematodes of the genus *Globodera* such as the yellow potato cyst nematode (*Globodera rostochiensis*) and the white potato cyst nematode (*Globodera pallida*); nematodes of the genus *Heterodera* such as the soya bean cyst nematode (*Heterodera glycines*) and beet cyst eelworm (*Heterodera schachtii*); nematodes of the genus *Aphelenchoides* such as the rice white-tip nematode (*Aphelenchoides besseyi*), the chrysanthemum nematode (*Aphelenchoides ritzemabosi*) and the strawberry nematode (*Aphelenchoides fragariae*); nematodes of the genus *Aphelenchus* such as the fungivorous nematode (*Aphelenchus avenae*); nematodes of the genus *Radopholus*, such as the burrowing nematode (*Radopholus similis*); nematodes of the genus *Tylenchulus* such as the citrus root nematode (*Tylenchulus semipenetrans*); nematodes of the genus *Rotylenchulus* such as the reniform nematode (*Rotylenchulus reniformis*); tree-dwelling nematodes such as the pine wood nematode (*Bursaphelenchus xylophilus*) and the red ring nematode (*Bursaphelenchus cocophilus*) and the like.

Plants for the protection of which a compound of the formula (I) can be used include plants such as cereals (for example rice, barley, wheat, rye, oats, maize and the like), beans (soya bean, aduki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plants for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, watermelon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) are particularly suitable for controlling coffee nematodes, in particular *Pratylenchus brachyurus, Pratylenchus coffeae, Meloidogyne exigua, Meloidogyne incognita, Meloidogyne coffeicola, Helicoty-* lenchus spp. and also *Meloidogyne paranaensis, Rotylenchus* spp., *Xiphinema* spp., *Tylenchorhynchus* spp. and *Scutellonema* spp.

The compounds of the formula (I) are particularly suitable for controlling potato nematodes, in particular *Pratylenchus brachyurus, Pratylenchus pratensis, Pratylenchus scribneri, Pratylenchus penetrans, Pratylenchus coffeae, Ditylenchus dipsaci* and of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae* and *Meloinema* spp.

The compounds of the formula (I) are particularly suitable for controlling tomato nematodes, in particular *Meloidogyne arenaria, Meloidogyne hapla, Meloidogyne javanica, Meloidogyne incognita, Pratylenchus penetrans* and also *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus* and *Rotylenchulus reniformis*.

The compounds of the formula (I) are particularly suitable for controlling cucumber plant nematodes, in particular *Meloidogyne arenaria, Meloidogyne hapla, Meloidogyne javanica, Meloidogyne incognita, Rotylenchulus reniformis* and *Pratylenchus thornei*.

The compounds of the formula (I) are particularly suitable for controlling cotton nematodes, in particular *Belonolaimus longicaudatus, Meloidogyne incognita, Hoplolaimus columbus, Hoplolaimus galeatus* and *Rotylenchulus reniformis*.

The compounds of the formula (I) are particularly suitable for controlling maize nematodes, in particular *Belonolaimus longicaudatus, Paratrichodorus minor* and also *Pratylenchus brachyurus, Pratylenchus delattrei, Pratylenchus hexincisus, Pratylenchus penetrans, Pratylenchus zeae, (Belonolaimus gracilis), Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum* and *Subanguina radiciola*.

The compounds of the formula (I) are particularly suitable for controlling soya bean nematodes, in particular *Pratylenchus brachyurus, Pratylenchus pratensis, Pratylenchus penetrans, Pratylenchus scribneri, Belonolaimus longicaudatus, Heterodera glycines, Hoplolaimus columbus* and also *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus* and *Rotylenchulus reniformis*.

The compounds of the formula (I) are particularly suitable for controlling tobacco nematodes, in particular *Meloidogyne incognita, Meloidogyne javanica* and also *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus spp., Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp. and *Tetylenchus nicotianae*.

The compounds of the formula (I) are particularly suitable for controlling citrus nematodes, in particular *Pratylenchus coffeae* and also *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., *Hemicriconemoides, Radopholus similis* and *Radopholus citrophilus, Hemicycliophora arenaria, Hemicycliophora nudata* and *Tylenchulus semipenetrans*.

The compounds of the formula (I) are particularly suitable for controlling banana nematodes, in particular *Pratylenchus coffeae, Radopholus similis* and also *Pratylenchus giibbicaudatus, Pratylenchus loosi, Meloidogyne* spp., *Helicotylenchus multicinctus, Helicotylenchus dihystera* and *Rotylenchulus* spp.

The compounds of the formula (I) are particularly suitable for controlling pineapple nematodes, in particular *Pratylenchus zeae, Pratylenchus pratensis, Pratylenchus brachyurus, Pratylenchus goodeyi., Meloidogyne* spp., *Rotylenchulus reniformis* and also *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense* and *Criconemoides ornatum*.

The compounds of the formula (I) are particularly suitable for controlling grapevine nematodes, in particular *Pratylenchus vulnus, Meloidogyne arenaria, Meloidogyne incognita, Meloidogyne javanica, Xiphinema americanum, Xiphinema index* and also *Pratylenchus pratensis, Pratylenchus scribneri, Pratylenchus neglectus, Pratylenchus brachyurus, Pratylenchus thornei* and *Tylenchulus semipenetrans*.

The compounds of the formula (I) are particularly suitable for controlling nematodes in tree crops—pome fruit, in particular *Pratylenchus penetrans* and also *Pratylenchus vulnus*, *Longidorus elongatus*, *Meloidogyne incognita* and *Meloidogyne hapla*.

The compounds of the formula (I) are particularly suitable for controlling nematodes in tree crops—stone fruit, in particular *Pratylenchus penetrans*, *Pratylenchus vulnus*, *Meloidogyne arenaria*, *Meloidogyne hapla*, *Meloidogyne javanica*, *Meloidogyne incognita*, *Criconemella xenoplax* and also *Pratylenchus brachyurus*, *Pratylenchus coffeae*, *Pratylenchus scribneri*, *Pratylenchus zeae*, *Belonolaimus longicaudatus*, *Helicotylenchus dihystera*, *Xiphinema americanum*, *Criconemella curvata*, *Tylenchorhynchus claytoni*, *Paratylenchus hamatus*, *Paratylenchus projectus*, *Scutellonema brachyurum* and *Hoplolaimus galeatus*.

The compounds of the formula (I) are particularly suitable for controlling nematodes in tree crops, sugar cane and rice, in particular *Trichodorus* spp., *Criconemella* spp. and also *Pratylenchus* spp., *Paratrichodorus* spp., *Meloidogyne* spp., *Helicotylenchus* spp., *Tylenchorhynchus* spp., *Aphelenchoides* spp., *Heterodera* spp, *Xiphinema* spp. and *Cacopaurus pestis*.

In the present context, the term "nematodes" also refers to nematodes damaging humans or animals.

Specific nematode species harmful to humans or to animals are:

Trichinellida, for example: *Trichuris* spp., *Capillaria* spp., *Paracapillaria* spp., *Eucoleus* spp., *Trichomosoides* spp., *Trichinella* spp.

From the order of the Tylenchida, for example: *Micronema* spp., *Strongyloides* spp.

From the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Many known nematicides also act against other parasitic helminths and are therefore used for controlling worms—not necessarily belonging to the group Nematoda—which are parasites in humans and animals. The present invention also relates to the use of the compounds of the formula (I) as anthelmintic medicaments. The pathogenic endoparasitic helminths include Platyhelminthes (e.g. Monogenea, cestodes and trematodes), Acanthocephala and Pentastoma. The following helminths may be mentioned as being preferred:

Monogenea: for example: *Gyrodactylus* spp., *Dactylogyrus* spp., *Polystoma* spp.

Cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.

From the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.

From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal keeping, the administration of the compounds of the formula (I) is carried out in a known manner, directly or enterally, parenterally, dermally or nasally in the form of suitable use forms. Administration may be prophylactic or therapeutic.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). If appropriate, they can also be used as intermediates or precursors for the synthesis of other active ingredients.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active ingredients.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which improves the biological activity of the formulation without having biological activity itself. Examples of adjuvants are agents which promote retention, the spreading characteristics, adhesion to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be such substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents essentially include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

In principle, it is possible to use any suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and natural rock flours such as kaolins, aluminas, talc, chalk, quartz, attapulgite, montmorillonite or diatomaceous earth, and synthetic rock flour such as finely divided silica, aluminium oxide and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, corn cobs and tobacco stalks.

It is also possible to use liquefied gaseous extenders or solvents. Especially suitable are those extenders or carriers which are gaseous at standard temperature and under standard pressure, for example aerosol propellants such as halohydrocarbons, or else butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

In addition, stabilizers, such as low-temperature stabilizers, preservatives, antioxidants, light stabilizers or other agents which improve chemical and/or physical stability, may be present. In addition, foam formers or defoamers may be present.

In addition, the formulations and use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further possible auxiliaries are mineral and vegetable oils.

Optionally, yet further auxiliaries may be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and hence increase the mobility of active ingredients in the cuticle. The method described in the literature (Baur et al., 1997, Pesticide Science 51, 131-152) can be used for determining this property. Examples include alcohol alkoxylates, for example coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment of the invention, the compounds of the formula (I) are in the form of formulations or the use forms prepared from these formulations in a mixture with further compounds, preferably those as described below.

If one of the compounds mentioned below can occur in various tautomeric forms, these forms are also included even if not explicitly mentioned in each case.

Insecticides/acaricides/nematicides

The active ingredients specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues e.g. hydroprene, kinoprene and methoprene or fenoxycarb or pyriproxyfen.

(8) Active ingredients with unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide, further active ingredients, for example afidopyropen, azadirachtin, benclothiaz, benzoximate, bifenazate, bromopropylate, chinomethionat, cryolite, dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; and also preparations based on *Bacillus firmus* (I-1582, BioNeem, Votivo), and also the following compounds: 3-bromo-N-{2-bromo-4-chloro-6-[(1-cyclopropylethyl)carbamoyl] phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino] ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl] carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl) sulphonyl]-6-(trifluoromethyl)imidazo[1,2-a]pyridine-2-carboxamide (known from WO2010/129500), 4-[5-(3,5-dichlorophenyl-5-(trifluoromethyl)-4,5-dihydro-1,2-oxazol-3-yl]-2-methyl-N-(1-oxidothietan-3-yl)benzamide (known from WO2009/080250), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N-nitro-2-pentylidenehydrazine-carboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl) pyrimidine (known from CN101337940), N-[2-(tert-butylcarbamoyl)-4-chloro-6-methylphenyl]-1-(3- chloropyridin-2-yl)-3-(fluoromethoxy)-1H-pyrazole-5-carboxamide (known from WO2008/134969).

Fungicides

The active ingredients specified herein by their common name are known and described, for example, in the "Pesticide Manual" or on the Internet (for example: http://www.alanwood.net/pesticides).

(1) Ergosterol biosynthesis inhibitors, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors), for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-epimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid (3) Respiration inhibitors (respiratory chain inhibitors) that act on complex III of the respiratory chain, for example (3.1) ametoctradin, (3.2) amisulbrom, (3.3) azoxystrobin, (3.4) cyazofamid, (3.5) coumethoxystrobin, (3.6) coumoxystrobin, (3.7) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl]phenyl}ethanamide, (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide (4) inhibitors of mitosis and cell division, for example (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity such as, for example, (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copperoxine, (5.28) propamidine, (5.29) propineb, (5.30) sulphur and sulphur preparations such as, for example calcium polysulphide, (5.31) thiram, (5.32) tolylfluanid, (5.33) zineb, (5.34) ziram and (5.35) anilazine.

(6) Resistance inducers, for example (6.1) acibenzolar-S-methyl, (6.2) isotianil, (6.3) probenazole, (6.4) tiadinil and (6.5) laminarin.

(7) Amino acid and protein biosynthesis inhibitors, for example (7.1), (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors, for example (8.1) fentin acetate, (8.2) fentin chloride, (8.3) fentin hydroxide and (8.4) silthiofam.

(9) Cell wall synthesis inhibitors, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Lipid and membrane synthesis inhibitors, for example (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Nucleic acid synthesis inhibitors, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors, for example (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers, for example (14.1) binapacryl, (14.2) dinocap, (14.3) ferimzone, (14.4) fluazinam and (14.5) meptyldinocap.

(15) Further compounds, for example (15.1) benthiazole, (15.2) bethoxazine, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N—{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl- 3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulphate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulphanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3 S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenyl)oxiran-2-yl]methyl}-1H-1,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5 S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5 S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl- 1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine. All the mixing components mentioned in classes (1) to (15), as the case may be, may form salts with suitable bases or acids if they are capable of doing so on the basis of their functional groups.

Biological Pesticides as Mixing Components

The compounds of the formula (I) can be combined with biological pesticides.

Biological pesticides include especially bacteria, fungi, yeasts, plant extracts and those products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, in particular *B. cereus* strain CNCM 1-1562 or *Bacillus firmus*, strain 1-1582 (Accession number CNCM 1-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), or *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. kurstaki strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39. (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, Dryopteris filix-mas, *Equisetum arvense*, Fortune Aza, Fungastop, Heads Up (*Chenopodium quinoa* saponin extract), pyrethrum/pyrethrins, *Quassia amara, Quercus*, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and parts of plants can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapevines). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Parts of plants shall be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested material and vegetative and generative propagation material, for example cuttings, tubers, rhizomes, slips and seeds.

The inventive treatment of the plants and parts of plants with the compounds of the formula (I) is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal ingredients, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, in which case treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed gives rise to a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of pesticides.

The present invention therefore in particular also relates to a method for the protection of seed and germinating plants, from attack by pests, by treating the seed with one of the compounds of the formula (I). The inventive method for protecting seed and germinating plants against attack by pests further comprises a method in which the seed is treated simultaneously in one operation or sequentially with a compound of the formula (I) and a mixing component. It also further comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occurs when one of the compounds of the formula (I) acts systemically is that the treatment of the seed protects not just the seed itself but also the plants resulting therefrom after emergence against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

In addition, compounds of the formula (I) can be used in combination with signalling technology compositions, which results in better colonization by symbionts, for example *rhizobia*, mycorrhizae and/or endophytic bacteria or fungi, and/or leads to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beets (for example sugarbeets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, for example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which, for example, has been pre-swollen in water up to a particular stage (pigeon breast stage), which leads to better germination and to more homogeneous emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing compounds of the formula (I) with customary additives such as, for example, customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are customary for the formulation of active agrochemical ingredients. Preference is given to using alkyl naphthalenesulphonates, such as diisopropyl or diisobutyl naphthalenesulphonates.

Suitable dispersants and/or emulsifiers which may be present in the seed-dressing formulations usable in accordance with the invention are all nonionic, anionic and cationic dispersants customary for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances customary for formulation of active agrochemical ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term endoparasites includes especially helminths and protozoa, such as coccidia. Ectoparasites are typically and preferably arthropods, especially insects and acarids.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal keeping is enabled and better animal well-being is achievable.

In relation to the animal health field, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; and also nuisance and hygiene pests from the order of the Blattarida.

Arthropods further include:

from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombicula* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa include:

Mastigophora (*Flagellata*), for example Trypanosomatidae, for example, *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example, *Giardia lamblia*, *G. canis;*

Sarcomastigophora (Rhizopoda) such as Entamoebidae, for example, *Entamoeba histolytica*, Hartmanellidae, for example, *Acanthamoeba* sp., *Harmanella* sp.;

Apicomplexa (Sporozoa) such as Eimeridae, for example, *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, *E. spec.*, *E. stiedai*, *E. suis*, *E. tenella*, *E. truncata*, *E. truttae*, *E. zuernii*, *Globidium* spec., *Isospora belli*, *I. canis*, *I. felis*, *I. ohioensis*, *I. rivolta*, *I.* spec., *I. suis*, *Cystisospora* spec., *Cryptosporidium* spec., in particular *C. parvum*; such as Toxoplasmadidae, for example, *Toxoplasma gondii*, *Hammondia heydornii*, *Neospora caninum*, *Besnoitia besnoitii*; such as Sarcocystidae, for example, *Sarcocystis bovicanis*, *S. bovihominis*, *S. ovicanis*, *S. ovifelis*, *S. neurona*, *S. spec.*, *S. suihominis*, such as Leucozoidae, for example, *Leucozytozoon simondi*, such as Plasmodiidae, for example, *Plasmodium berghei*, *P. falciparum*, *P. malariae*, *P. ovale*, *P. vivax*, *P. spec.*, such as Piroplasmea, for example, *Babesia argentina*, *B. bovis*, *B. canis*, *B. spec.*, *Theileria parva*, *Theileria* spec., such as Adeleina, for example, *Hepatozoon canis*, *H. spec.*

Pathogenic endoparasites, which are helminths, include Platyhelmintha (e.g. Monogenea, cestodes and trematodes), roundworms, Acanthocephala, and Pentastoma. These include:

Monogenea: for example: *Gyrodactylus* spp., *Dactylogyrus* spp., *Polystoma* spp.

Cestodes: from the order of the Pseudophyllidea, for example: *Diphyllobothrium* spp., *Spirometra* spp., *Schistocephalus* spp., *Ligula* spp., *Bothridium* spp., *Diphlogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

roundworms: Trichinellida, for example: *Trichuris* spp., *Capillaria* spp., *Paracapillaria* spp., *Eucoleus* spp., *Trichomosoides* spp., *Trichinella* spp.;

from the order of the Tylenchida, for example: *Micronema* spp., *Strongyloides* spp.

from the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp *Nematodirus* spp., *Hyostrongylus* spp., *Obeliscoides* spp., *Amidostomum* spp., *Ollulanus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;

from the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal keeping, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as medicament.

A further aspect refers to the use of a compound of the formula (I) as an antiendoparasitic agent, in particular as a helminthicidal agent or antiprotozoic agent. Compounds of the formula (I) are suitable for use as an antiendoparasitic agent, especially as a helminthicidal agent or antiprotozoic agent, for example in animal husbandry, in animal breeding, in buildings for livestock and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in buildings for livestock or in the hygiene sector.

Anthelmintic Mixing Components

The following anthelmintic mixing components may be mentioned by way of example:

anthelmintically active ingredients including trematicidally and cestocidally active ingredients:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclopholan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example, viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes

*Anopheles*: malaria, filariosis;

*Culex*: Japanese encephalitis, filariasis, other viral diseases, transmission of worms;

*Aedes*: yellow fever, dengue fever, filariasis, other viral diseases;

Simuliidae: transmission of worms, in particular *Onchocerca volvulus*;

2) Lice: skin infections, epidemic typhus;

3) Fleas: plague, endemic typhus;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borellioses such as *Borrelia duttoni*, tick-borne encephalitis, Q fever (*Coxiella burnetii*), babesioses (*Babesia canis canis*).

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dims* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

The preparation and use examples which follow illustrate the invention without limiting it.

PREPARATION EXAMPLES

Synthesis of ethyl [5-phenyl-1,2,4-oxadiazol-3-yl] imidoformate (1-7), cf. WO 2009/011850

Stage 1: Methyl N-cyanobenzenecarboximidoate

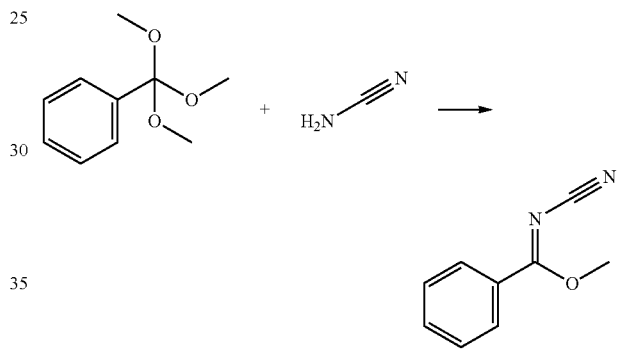

(Trimethoxymethyl)benzene (75 g) and cyanamide (17.304 g) were taken up in 78 ml of acetic anhydride and then stirred at 135° C. for 45 minutes. The mixture was then concentrated under reduced pressure, the residue was stirred with cyclohexane, and the solids were filtered off with suction and dried. This left 65.30 g of the title compound. HPLC-MS: log P (neutral)=1.83; mass (m/z): 161.1 (M+H)$^+$; $^1$H NMR (DMSO-D$_6$) 4.045 (s, 3H), 7.601-7.644 (m, 2H), 7.712-7.755 (m, 1H), 7.966-7.995 (m, 2H).

Stage 2: 5-Phenyl-1,2,4-oxadiazol-3-amine

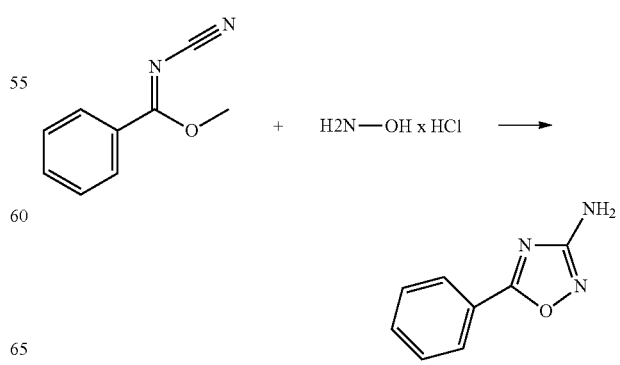

Methyl N-cyanobenzenecarboximidoate (30.50 g) was initially charged in 157 ml of methanol and, after addition of hydroxylammonium chloride (13.23 g), stirred at room temperature for 2 hours. Triethylamine (19.17 g) was then added at 0° C., at first forming a clear solution, and a solid precipitated out after 30 minutes. The mixture was stirred at room temperature overnight, and the solids were filtered off with suction, washed with water and dried. This left 10.60 g of the title compound.

HPLC-MS: log P (neutral)=1.28; mass (m/z): 162.1 (M+H)$^+$; $^1$H NMR (DMSO-D$_6$) 6.418 (s, 2H), 7.514-8.02 (m, 5H).

Stage 3: Ethyl [5-phenyl-1,2,4-oxadiazol-3-yl]imidoformate

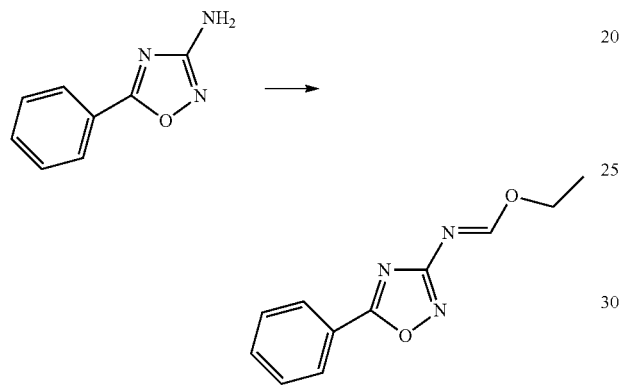

5-Phenyl-1,2,4-oxadiazol-3-amine (10.60 g) was stirred with 30 ml of triethyl orthoformate under reflux overnight. The mixture was subsequently left to cool, 100 ml of petroleum ether were added, the mixture was stirred at room temperature for 30 minutes and then the precipitated solids were filtered off with suction. This left 9.70 g of the title compound.

HPLC-MS: log P (neutral)=2.87; mass (m/z): 218.1 (M+H)$^+$; $^1$H NMR (DMSO-D$_6$) 1.343 (t, 3H), 4.389 (q, 2H), 7.621-7.743 (m, 3H), 8.085-8.106 (m, 2H), 8.705 (s, 1H).

Example 1

2-Trifluoromethyl-N-[1-(2-bromo-6-fluorophenyl)-1H-1,2,4-triazol-3-yl]benzamide (Table 1, Example I-1-30)

Stage 1: N-[1-(2-Bromo-6-fluorophenyl)-1H-1,2,4-triazol-3-yl]benzamide

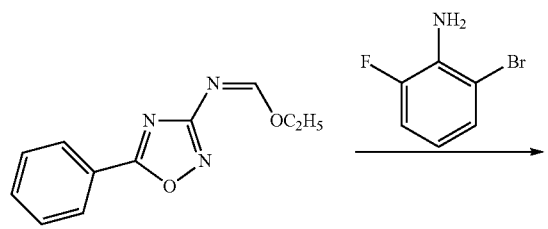

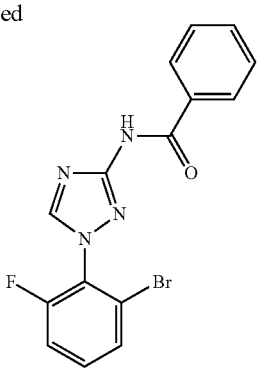

Ethyl [5-phenyl-1,2,4-oxadiazol-3-yl]imidoformate (2.00 g) and 2-bromo-6-fluoroaniline were heated to 150° C. for 4 h, the reaction mixture was cooled down to room temperature, the residue was stirred with 20 ml of ethanol for 45 minutes and the remaining solids were filtered off with suction. This left 2.0 g of the desired title compound.

HPLC-MS: log P (neutral)=1.79; mass (m/z): 361 (M+H)$^+$; $^1$H NMR (DMSO-D$_6$) 7.587 (m, 2H), 7.638 (m, 3H), 7.768 (m, 1H), 8.002 (m, 2H), 8.891 (s, 1H), 11.053 (s, 1H).

Stage 2: 1-(2-Bromo-6-fluorophenyl)-1H-1,2,4-triazol-3-amine

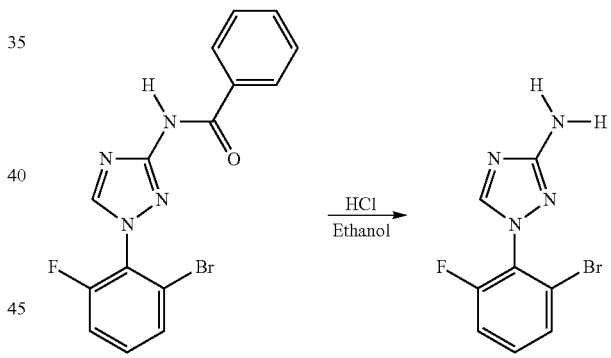

N-[1-(2-Bromo-6-fluorophenyl)-1H-1,2,4-triazol-3-yl]benzamide (2.1 g) was initially charged in 25 ml of ethanol, 6 ml of concentrated hydrochloric acid were added and then the mixture was stirred under reflux for 8 hours. Subsequently, the reaction mixture was concentrated under reduced pressure, and the residue was taken up in water and alkalized by addition of sodium hydroxide solution (pH 9). The aqueous phase was extracted with dichloromethane, and the combined extracts were dried and concentrated. The remaining crude product was purified by chromatography on silica gel by means of cyclohexane/ethyl acetate as eluent. Concentration of the extracts left 0.65 g of the title compound.

HPLC-MS: log P (neutral)=0.92; mass (m/z): 257 (M+H)$^+$; $^1$H NMR (DMSO-D$_6$) 5.604 (s, 2H), 7.797-7.876 (m, 3H); 8.346 (s, 1H).

Stage 3: 2-Trifluoromethyl-N-[1-(2-bromo-6-fluorophenyl)-1H-1,2,4-triazol-3-yl]benzamide

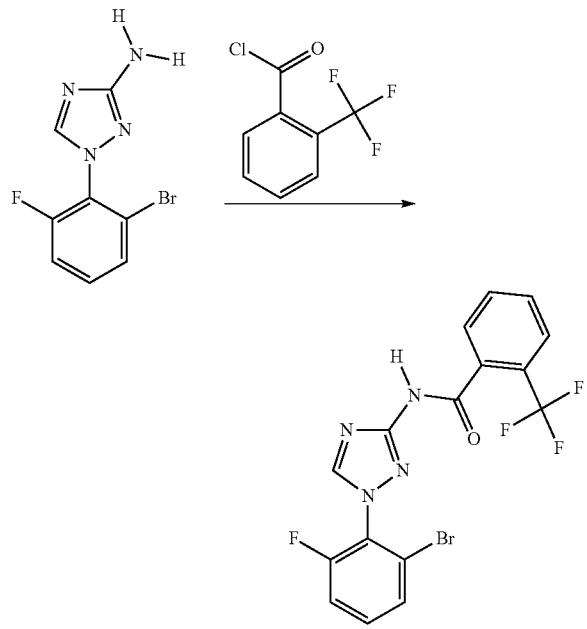

1-(2-Bromo-6-fluorophenyl)-1H-1,2,4-triazol-3-amine (0.12 g) was added to a solution of pyridine (0.11 g) in dichloromethane (10 ml), and a solution of 2-trifluoromethylbenzoyl chloride (0.107 g) in dichloromethane was added dropwise at 0° C. After the addition had ended, the mixture was left to stir at 0° C. for 4 hours and then at room temperature overnight. Subsequently, the reaction solution was diluted with further dichloromethane and washed twice with dilute hydrochloric acid and once with water. The organic phase was removed, dried and concentrated. The remaining residue was purified by chromatography on silica gel with cyclohexane/ethyl acetate as eluent. This gave 0.163 g of the title compound. HPLC-MS: log P (neutral) =2.15; mass (m/z): 429 (M+H)$^+$; $^1$H NMR (DMSO-D$_6$) 7.608-7.837 (m, 7H), 8.863 (s, 1H), 11.344 (s, 1H).

Example 2

2-Trifluoromethyl-N-[1-(2,6-difluorophenyl)-1H-1,2,4-triazol-3-yl]benzamide (Table 1, Example I-1-11)

Stage 1: N-[1-(2,6-Difluorophenyl)-1H-1,2,4-triazol-3-yl]benzamide

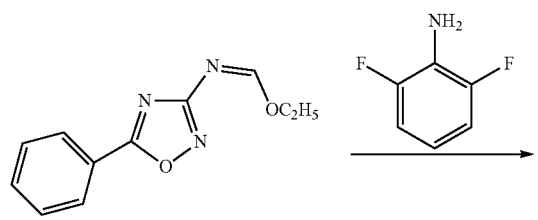

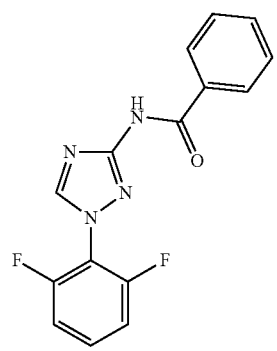

Ethyl [5-phenyl-1,2,4-oxadiazol-3-yl]imidoformate (5.00 g) and 2,6-difluoroaniline (2.97 g) were heated at 150° C. for 4 hours, the reaction mixture was cooled and then 30 ml of ethanol were added. The mixture was stirred at room temperature for 45 minutes and the remaining solids were filtered off with suction and dried. This left 6.0 g of the desired product. HPLC-MS: log P (neutral)=1.59; mass (m/z): 301 (M+H)$^+$; $^1$H NMR (DMSO-D$_6$) 7.496 (m, 4H), 7.594 (m, 1H), 7.701 (m, 1H), 7.987 (m, 2H), 8.939 (s, 1H), 11.049 (s, 1H).

Stage 2: 1-(2,6-Difluorophenyl)-1H-1,2,4-triazol-3-amine

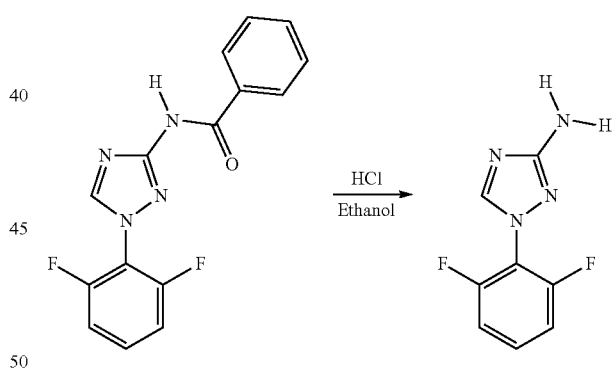

N-[1-(2,6-Difluorophenyl)-1H-1,2,4-triazol-3-yl]benzamide (1.2 g) was initially charged in 15 ml of ethanol, 3 ml of concentrated hydrochloric acid were added and then the mixture was stirred under reflux for 8 hours. Subsequently, the reaction mixture was concentrated under reduced pressure, and the residue was taken up in water and alkalized by addition of sodium hydroxide solution (pH 9). The mixture was stirred at room temperature for 30 minutes, and the solids were filtered off with suction, stirred with diethyl ether and dried. This left 0.7 g of the title compound. HPLC-MS: log P (neutral)=0.61; mass (m/z): 197.1 (M+H)$^+$; $^1$H NMR (DMSO-D$_6$) 5.664 (s, 2H), 7.365 (m, 2H), 7.664 (m, 1H), 8.401 (s, 1H).

3rd stage: 2-Trifluoromethyl-N-[1-(2,6-difluorophenyl)-1H-1,2,4-triazol-3-yl]benzamide

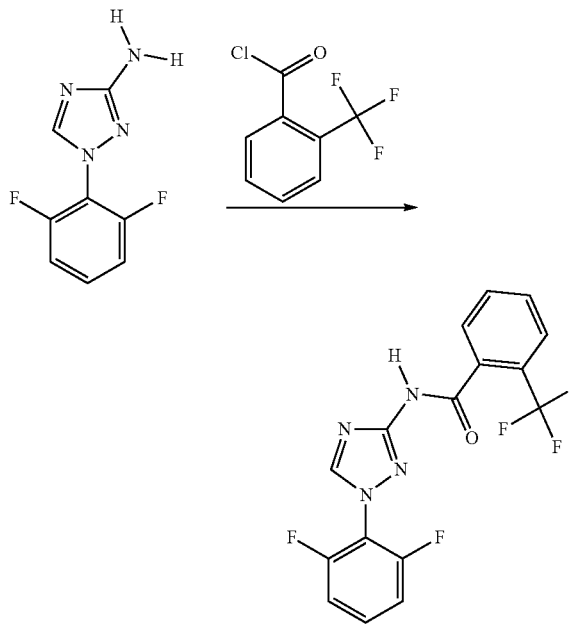

1-(2,6-Difluorophenyl)-1H-1,2,4-triazol-3-amine (1.00 g) was added to a solution of pyridine (2.67 g) in dichloromethane (60 ml), and a solution of 2-trifluoromethylbenzoyl chloride (2.585 g) in dichloromethane (15 ml) was added dropwise at 0° C.-5° C. within 20 minutes. After the addition had ended, the mixture was left to stir at 0° C.-5° C. for 3 hours. Subsequently, the reaction solution was diluted with further dichloromethane (60 ml) and washed twice with dilute hydrochloric acid (50 ml) and once with water. The organic phase was removed, dried and concentrated. The remaining residue was purified by chromatography on silica gel with cyclohexane/ethyl acetate as eluent. This gave 3.00 g of the title compound. HPLC-MS: log P=1.97; mass (m/z): 369.1 (M+H)$^+$; $^1$H NMR (DMSO-D$_6$) 7.458 (m, 2H), 7.714-7.843 (m, 5H), 8.906 (s, 1H), 11.360 (s, 1H).

Example 3

2-Ethyl-N-[1-(2-bromo-6-fluorophenyl)-1H-1,2,4-triazol-3-yl]benzamide (Table 1, Example I-1-15)

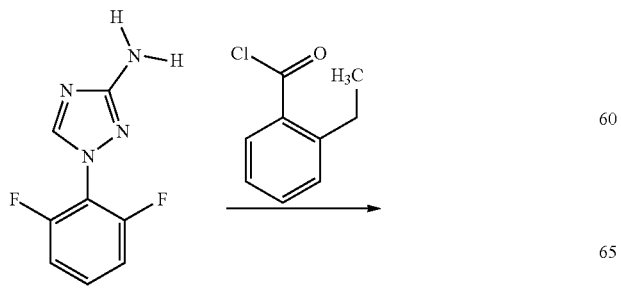

-continued

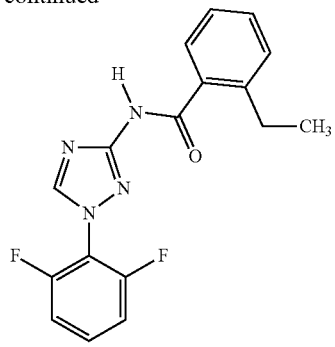

1-(2,6-Difluorophenyl)-1H-1,2,4-triazol-3-amine (0.12 g) was added to a solution of pyridine (0.145 g) in dichloromethane (6 ml), and a solution of 2-ethylbenzoyl chloride (0.113 g) in dichloromethane (15 ml) was added dropwise at 0° C.-5° C. within 20 minutes. After the addition had ended, the mixture was left to stir at 0° C.-5° C. for 3 hours and then at room temperature overnight. Subsequently, the reaction solution was diluted with further dichloromethane and washed twice with dilute hydrochloric acid and once with water. The organic phase was removed, dried and concentrated. The remaining residue was purified by chromatography on silica gel with cyclohexane/ethyl acetate as eluent. This gave 0.102 g of the title compound. HPLC-MS: log P (neutral)=2.05; mass 329.1 (m/z): (M+H)$^+$; $^1$H NMR (DMSO-D$_6$) 1.177 (tr, 3H), 2.747 (q, 2H), 7.264-7.337 (m, 2H), 7.398-7.479 (m, 4H), 7.676-7.751 (m, 1H), 8.887 (s, 1H), 11.002 (s, 1H).

Example 4

N-{1-[2-Fluoro-6-(trifluoromethyl)phenyl]-1H-1,2,4-triazol-3-yl}-2-iodobenzamide (Table 1, Example I-1-28)

Stage 1: N-{1-[2-Fluoro-6-(trifluoromethyl)phenyl]-1H-1,2,4-triazol-3-yl}benzamide

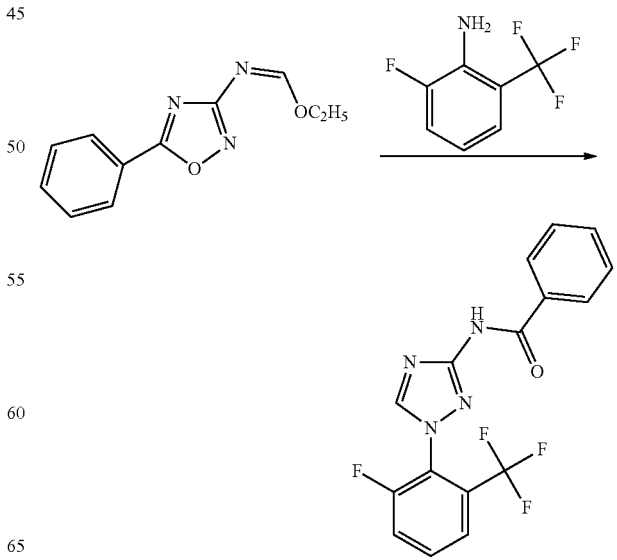

Ethyl [5-phenyl-1,2,4-oxadiazol-3-yl]imidoformate (2.50 g) and 2-fluoro-6-trifluoromethylaniline (2.061 g) were stirred at 150° C. overnight, the reaction mixture was cooled and then 20 ml of ethanol were added. The mixture was stirred at room temperature for a further 45 minutes and the remaining solids were filtered off with suction and dried. The crude product was purified by chromatography on silica gel with cyclohexane/ethyl acetate as eluent. Concentration of the extracts left 1.1 g of the title compound. HPLC-MS: log P (neutral)=1.95; mass (m/z): 351 (M+H)$^+$; $^1$H NMR (DMSO-D$_6$) 7.501 (m, 2H), 7.601 (m, 1H), 7.883-7.984 (m, 5H), 8.893 (s, 1H), 11.038 (s, 1H).

Stage 2: 1-[2-Fluoro-6-(trifluoromethyl)phenyl]-1H-1,2,4-triazol-3-amine

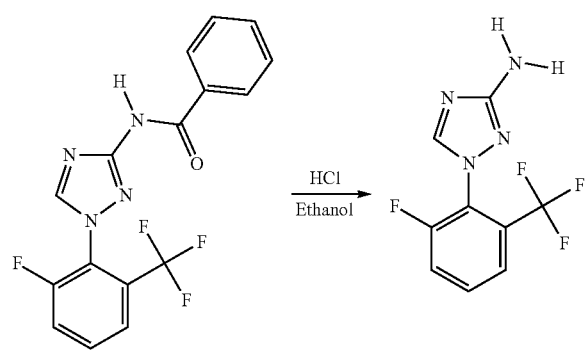 [SMILES: O=C(Nc1ncn(-c2c(F)cccc2C(F)(F)F)n1)c1ccccc1 ; Cl ; Nc1ncn(-c2c(F)cccc2C(F)(F)F)n1]

N-{1-[2-Fluoro-6-(trifluoromethyl)phenyl]-1H-1,2,4-triazol-3-yl}benzamide (1.2 g) was initially charged in 20 ml of ethanol, 5 ml of concentrated hydrochloric acid were added and then the mixture was stirred under reflux for 8 hours. Subsequently, the reaction mixture was concentrated under reduced pressure, and the residue was taken up in water and alkalized by addition of sodium hydroxide solution (pH 9). The mixture was stirred at room temperature for a further 30 minutes and the solids were filtered off with suction and dried. This left 0.57 g of the title compound. HPLC-MS: log P (neutral)=1.09; purity=99.3%; mass (m/z): 247.1 (M+H)$^+$; $^1$H NMR (DMSO-D$_6$) 5.638 (s, 2H), 7.797-7.876 (m, 3H), 8.346 (s, 1H).

Stage 3: N-{1-[2-Fluoro-6-(trifluoromethyl)phenyl]-1H-1,2,4-triazol-3-yl}-2-iodobenzamide

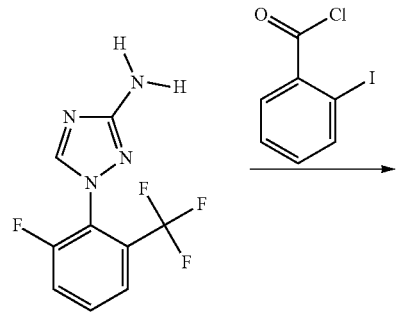

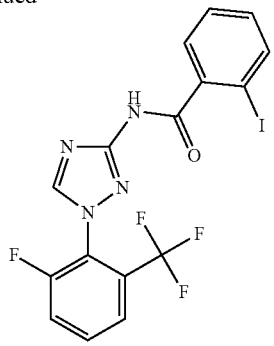

Pyridine (0.116 g) was initially charged in dichloromethane (10 ml), 1-[2-fluoro-6-(trifluoromethyl)phenyl]-1H-1,2,4-triazol-3-amine (0.120 g) was added and then 2-iodobenzoyl chloride (0.143 g) was added at 0° C. Subsequently, the mixture was stirred first at 0° C. for 3 hours and then at room temperature overnight. After the reaction mixture had been diluted with dichloromethane, the organic phase was washed with dilute hydrochloric acid and the organic phase was removed, dried and concentrated under reduced pressure. The crude product was purified by chromatography on silica gel with cyclohexane/ethyl acetate as eluent. Concentration of the extracts left 0.12 g of the title compound. HPLC-MS: log P (neutral)=2.21; mass (m/z): 477 (M+H)$^+$; $^1$H NMR (DMSO-D$_6$) 7.199-7.218 (m, 1H), 7.472 (m, 2H), 7.892-7.953 (m, 4H), 8.843 (s, 1H), 11.172 (s, 1H).

Example 5

N-[1-(3,5-Difluoropyridin-2-yl)-1H-1,2,4-triazol-3-yl]-2-(trifluoromethyl)benzamide Stage 1: N-[1-(3,5-Difluoropyridin-2-yl)-1H-1,2,4-triazol-3-yl]benzamide

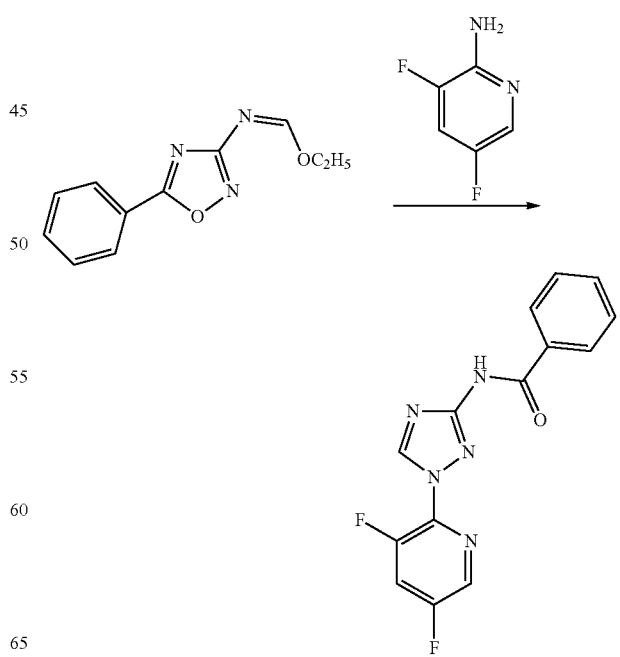

Ethyl [5-phenyl-1,2,4-oxadiazol-3-yl]imidoformate (2.50 g) and 3,5-difluoropyridin-2-amine (1.497 g) were heated at 150° C. for 4 hours, the reaction mixture was cooled and then 10 ml of ethanol were added. The mixture was stirred at room temperature for 45 minutes and the remaining solids were filtered off with suction and dried. This left 2.50 g of the desired product. HPLC-MS: log P (neutral)=1.36; mass (m/z): 302.1 (M+H)$^+$; $^1$H NMR (DMSO-D$_6$) 7.514-7.577 (m, 2H), 7.596-7.636 (m, 1H), 7.997 (m, 2H), 8.359-8.412 (m, 1H), 8.587 (d, 1H), 9.103 (s, 1H) 11.062 (s, 1H).

Stage 2: 1-(3,5-Difluoropyridin-2-yl)-1H-1,2,4-triazol-3-amine

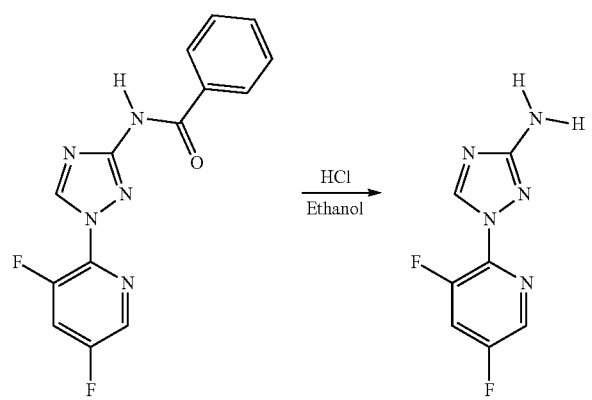 [SMILES: O=C(Nc1ncn(-c2ncc(F)cc2F)n1)c1ccccc1 ; Cl ; Nc1ncn(-c2ncc(F)cc2F)n1]

N-[1-(3,5-Difluoropyridin-2-yl)-1H-1,2,4-triazol-3-yl] benzamide (2.4 g) was initially charged in 25 ml of ethanol, 4 ml of concentrated hydrochloric acid were added and then the mixture was stirred under reflux for 8 hours. Subsequently, the reaction mixture was concentrated under reduced pressure, and the residue was taken up in water and alkalized by addition of sodium hydroxide solution (pH 8). The mixture was stirred at room temperature for 30 minutes and the solids were filtered off with suction and dried. This left 0.130 g of the title compound. HPLC-MS: log P=0.30; mass (m/z): 198 (M+H)$^+$; $^1$H NMR (DMSO-D$_6$) 5.808 (s, 2H), 8.219-8.273 (m, 1H), 8.455 (d, 1H), 8.663 (s, 1H).

Stage 3: N-[1-(3,5-Difluoropyridin-2-yl)-1H-1,2,4-triazol-3-yl]-2-(trifluoromethyl)benzamide

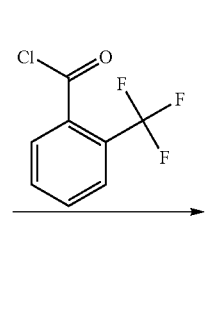

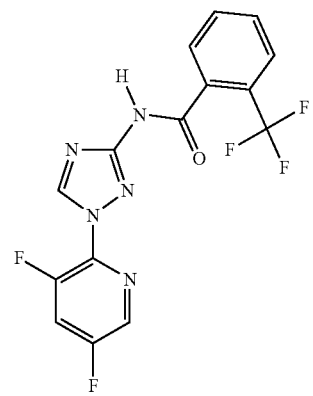

To 1-(3,5-difluoropyridin-2-yl)-1H-1,2,4-triazol-3-amine (0.10 g) in pyridine (2.934 g) was added, at 0° C., 2-trifluoromethylbenzoyl chloride (0.116 g). After the addition had ended, the mixture was left to stir at room temperature overnight, the reaction mixture was stirred with dilute hydrochloric acid, and the remaining solids were filtered off and washed with water. Drying left 0.150 g of the desired title compound. HPLC-MS: log P=1.76; mass (m/z): 370 (M+H)$^+$; $^1$H NMR (DMSO-D$_6$) 7.706-7.847 (m, 4H), 8.377 (m, 1H), 8.575 (s, 1H), 9.058 (s, 1H), 11.369 (s, 1H).

The following compounds of the formula (IIa-1) in which R3 is hydrogen were obtained analogously to the examples given:

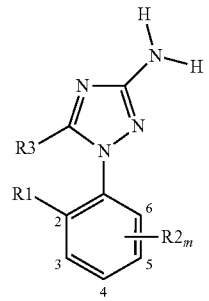

| R1 | R2$_m$ | logP (neutral) | $^1$H NMR (DMSO-D$_6$) |
|---|---|---|---|
| F | — | 0.86 | 8.5 (s, 1H), 7.709 (m, 1H), 7.483 (m, 1H), 7.385 (m, 2H), 5.749 (s, 2H) |
| Cl | — | 0.96 | 5.624 (s, 2H), 7.680 (m, 1H), 7.497 (m, 2H), 7.592 (m, 2H), 8.438 (s, 2H) |
| CF$_3$ | — | 1.16 | 8.279 (s, 1H), 7.937 (m, 1H), 7.858 (m, 1H), 7.737 (m, 1H), 7.641 (m, 2H), 5.578 (s, 2H) |
| OCF$_3$ | — | 1.44 | 8.437 (s, 1H), 7.740 (m, 1H), 7.493-7.588 (m, 4H), 5.707 (s, 2H) |
| Br | — | 1.03 | 8.387 (s, 1H), 7.828 (m, 1H), 7.530 (m, 1H), 7.383 (m, 1H), 5.587 (s, 2H) |
| I | — | 1.13 | 8.314 (s, 1H), 8.002 (m, 1H), 7.544 (m, 1H), 7.447 (m, 1H), 7.259 (m, 1H), 5.539 (s, 2H) |
| Cl | 6-F | 0.86 | 8.365 (s, 1H), 7.475-7.602 (m, 3H), 5.623 (s, 2H) |
| Br | 6-Br | 1.2 | 8.291 (s, 1H), 7.865 (m, 1H), 7.433 (m, 1H), 5.564 (s, 2H) |
| F | 6-I | 1.07 | 8.309 (s, 1H9, 7.839 (m, 1H), 7.512 (m, 1H), 7.381 (m, 1H), 5.580 (s, 2H) |
| F | 6-CH$_3$ | 1.03 | 8.271 (s, 1H), 7.408 (m, 1H), 7.287 (m, 1H), 7.175 (m, 1H), 5.510 (s, 2H), 2.237 (s, 3H) |
| Cl | 6-CH$_3$ | 1.12 | 8.228 (s, 1H), 7.509 (m, 1H); 7.419 (m, 1H), 7.419 (m, 1H), 5.517 (s, 2H); 2.498 (s, 3H) |
| Cl | 6-C$_2$H$_5$ | 1.12 | 8.249 (s, 1H), 7.523 (m, 2H), 7.401 (m, 1H), 5.512 (s, 2H), 2.397 (q, 2H), 1.036 (t, 3H) |
| Cl | 6% Cl: | 0.94 | 8.327 (s, 1H), 7.690 (m, 2H), 7.548-7.585 (m, 1H), 5.593 (s, 2H) |
| CH$_3$ | 6-OCH$_3$ | 0.98 | 8.039 (s, 1H), 7.348 (m, 1H), 7.029 (m, 1H), 6.948 (m, 1H); 5.364 (s, 2H), 3.718 (s, 3H), 2.043 (s, 3H) |
| Cl | 3-Cl | 1.41 | 8,483 (broad, 1H), 7,756 (s, 1H), 7,588 (t, 2H), 2.837, 492 (m, 2H), 5,681 (s, 3H). |
| Cl | 4-Cl | 1.48 | 8.461 (s, 1H), 7.885 (m, 1H), 7.587 (m, 2H), 5.677 (s, 2H) |
| Cl | 5% Cl: | 1.44 | 8.515 (s, 1H), 7.713 (m, 2H), 7.526 (m, 1H), 5.717 (s, 2H) |
| F | 3,6-F$_2$-phenyl | 0.84 | 8.455 (s, 1H), 7.710 (m, 1H), 7.454 (m, 1H), 5.761 (s, 2H) |
| F | 4,6-F$_2$ | 0.82 | 8.379 (s, 1H), 7.521 (m, 2H), 5.675 (s, 2H) |
| F | 3,4,5,6-F$_4$ | 1.31 | 8.484 (s, 1H), 5.868 (s, 2H) |
| Br | 6-Br-4-F | 1.35 | 8.276 (s, 1H), 7.939 (m, 2H), 5.575 (s, 2H) |

The following N-[1-aryl-1H-1,2,4-triazol-3-yl]benzamides (cf. formula (1-9) in Synthesis Scheme 1) were obtained analogously to the examples given:

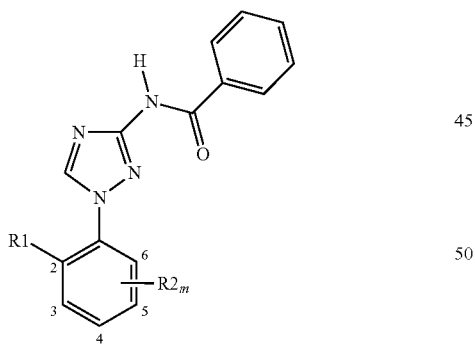

| R1 | R2$_m$ | logP (neutral) | $^1$H NMR (DMSO-D$_6$) |
|---|---|---|---|
| F | — | 1.69 | 11.030 (s, 1H), 8.962 (s, 1H), 8.015 (m, 2H), 7.842 (m, 1H), 7.588 (m, 5H), 7.449 (m, 1H) |
| Cl | — | 1.75 | 10.999 (s, 1H), 8.906 (s, 1H), 8.006 (m, 2H), 7.776 (m, 1H), 7.719 (m, 1H), 7.694 (m, 3H), 7.523 (m, 2H) |
| CF$_3$ | — | 1.91 | 10.985 (s, 1H), 8.819 (s, 1H), 7.756-7,991 (m, 6H), 7.610 (m, 1H), 7.520 (m, 2H) |
| OCF$_3$ | — | 2.15 | 11.018 (s, 1H), 8.920 (s, 1H), 8.011 (m, 2H), 7.828 (m, 1H), 7.697 (m, 4H) 7.5088 (m, 2H) |

| R1 | R2$_m$ | logP (neutral) | $^1$H NMR (DMSO-D$_6$) |
|---|---|---|---|
| Br | — | 1.80 | 11.001 (s, 1H), 8.876 (s, 1H), 7.987 (m, 2H), 7.899 (m, 1H), 7.504-7.679 (m, 6H) |
| I | — | 1.87 | 10.994 (s, 1H), 8.824 (s, 1H), 7.988-8.098 (m, 3H), 7.585-7.604 (m, 4H), 7.364 (m, 1H) |
| Cl | 6-F | 1.75 | 11.050 (s, 1H), 8.907 (s, 1H), 8.002 (m, 2H), 7.572-7.710 (m, 4H), 7.504 (m, 2H) |
| F | 6-CH$_3$ | 1.89 | 10.924 (s, 1H), 8.778 (s, 1H), 8.001 (m, 2H), 7.605 (m, 1H), 7.503 (m, 3H), 7.380 (m, 1H), 7.269 (m, 1H), 2.247 (s, 3H) |
| F | 6-I | 1.79 | 11.047 (s, 1H), 8.857 (s, 1H), 7.989 (m, 3H), 7.424-7.604 (m, 5H) |
| Cl | 6-CH$_3$ | 1.92 | 10.990 (s, 1H), 8.781 (s, 1H) 8.004 (m, 2H), 7.579 (m, 2H), 7.501 (m, 4H), 2.111 (s, 3H) |
| Cl | 6-C$_2$H$_5$ | 2.2 | 10.977 (s, 1H), 8.812 (s, 1H), 8.004 (m, 2H), 7.489-7.592 (m, 6H), 2.383 (q, 2H), 1.061 (t, 3H) |
| Cl | 6-Cl | 1.8 | 11.062 (s, 1H), 8.875 (s, 1H), 7.985 (m, 2H), 7.780 (m, 7H), 7.500-7.701 (m, 4H) |
| Br | 6-Br | 2.00 | 11.075 (s, 1H), 8.845 (s, 1H), 8.203 (m, 1H), 7.823-8.036 (m, 3H), 7.499-7.695 (m, 4H) |
| CH$_3$ | 6-OCH$_3$ | 1.76 | 10.861 (s, 1H), 8.584 (s, 1H), 7.997 (m, 2H), 7.616 (m, 1H), 7.516 (m, 1H), 7.498 (m, 1H), 7.111 (m, 1H), 7.004 (m, 1H), 3.758 (s, 3H), 2.060 (s, 3H) |
| Cl | 3-Cl | 2.11 | 11.043 (s, 1H), 8.939 (s, 1H), 7.985 (m, 2H), 7.505-7.627 (m, 6H) |
| Cl | 4-Cl | 2.18 | 11.031 (s, 1H), 8.912 (s, 1H), 8.002 (m, 3H), 7.750 (m, 2H), 7.551 (m, 3H) |
| Cl | 5-Cl | 2.17 | 11.059 (s, 1H), 8.942 (s, 1H), 8.005 (m, 2H), 7.987 (m, 1H), 7.794 (m, 1H), 7.703 (m, 1H), 7.628 8m, 1H), 7.507 (m, 2H) |
| F | 3,6-F$_2$ | 1.73 | 11.102 (s, 1H), 8.971 (s, 1H), 7.898 (m, 3H), 7.805 (m, 1H), 7.560 (m, 1H), 7.510 (m, 3H) |
| F | 4,6-F$_2$ | 1.71 | 11.056 (s, 1H), 8.911 (s, 1H), 7.981 (m, 2H), 7.611 (m, 3H), 7.506 (m, 2H) |
| Br | 6-Br-4-F | 2.14 | 11.088 (s, 1H), 8.827 (s, 1H), 8.205 (m, 1H), 8.001 (m, 3H), 7.733 (m, 1H), 7.582 (m, 3H) |
| F | 3,4,5,6-F$_4$ | 2.11 | 11.163 (s, 1H), 8.991 (s, 1H), 7.986 (m, 2H), 7.528-7.652 (m, 3H) |

Proceeding from suitably substituted 3-amino-5-aryl-1,2,4-oxadiazoles, which are preparable with the aid of methods known from the literature (Heterocycles, 57, 811-823), it is possible to prepare the desired compounds of the formula (I-1) directly by reaction of appropriately substituted alkyl [5-aryl-1,2,4-oxadiazol-3-yl-]imidoformates (2-8) with suitable anilines.

Example 6

2-Chloro-N-[1-(2,6-difluorophenyl)-1H-1,2,4-triazol-3-yl]benzamide

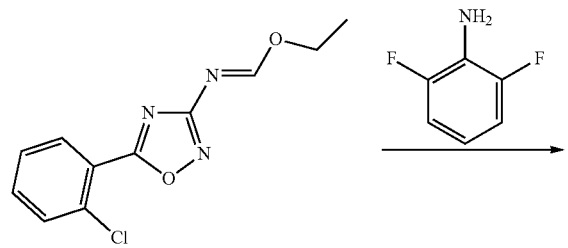

-continued

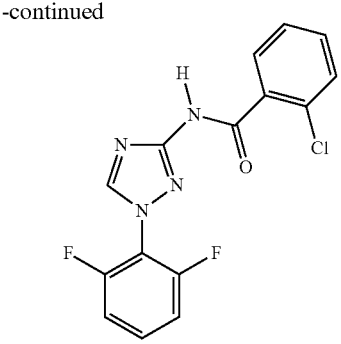

Ethyl [5-(2-chlorophenyl)-1,2,4-oxadiazol-3-yl]imidoformate (0.1 g) and 2,6-difluoroaniline (0.05 g) were stirred in a microwave apparatus at 170° C. and 250 watts for 30 minutes. The remaining residue was purified by chromatography on silica gel by means of cyclohexane/ethyl acetate as eluent. Concentration of the extracts left 0.017 g of the title compound. HPLC-MS: log P (neutral)=1.73; mass (m/z): 257 (M+H)$^+$; $^1$H NMR (DMSO-D$_6$) 7.416-7.750 (m, 7H); 8.891 (s, 1H); 11.272 (s, 1H).

Example 7

N-[2-(2-Methoxyphenyl)-2H-tetrazol-5-yl]-2-(trifluoromethyl)benzamide (Table 2, Example I-2-1)

Stage 1:
N-(2H-Tetrazol-5-yl)-2-(trifluoromethyl)benzamide

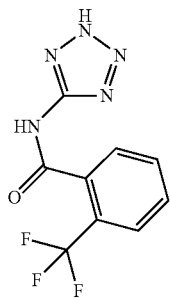 [SMILES: O=C(Nc1nn[nH]n1)c1ccccc1C(F)(F)F]

2H-Tetrazol-5-amine hydrate (200 mg) was initially charged in N,N-dimethylformamide (1 ml), triethylamine (294 mg) was added at 0° C. and the mixture was stirred at 0° C. for 1 hour. Subsequently, 2-(trifluoromethyl)benzoyl chloride (607 mg) was added dropwise at 0° C., and the mixture was stirred at 0° C. for a further 2 hours and warmed to room temperature. A colourless solid precipitated out, and was filtered off and dried. This gave 73 mg of the title compound. The mother liquor was purified by column chromatography with water/1% formic acid/acetonitrile as eluent (gradient=30 min from 95% water/1% formic acid to 100% acetonitrile). This gave a further 110 mg of the title compound. HPLC-MS: log P=1.17; mass (m/z): 258.1 (M+H)$^+$; $^1$H NMR (DMSO-D$_6$) 7.71-7.93 (m, 4H), 12.6 (s, 1H), 16.2 (s, 1H).

Stage 2: N-[2-(2-Methoxyphenyl)-2H-tetrazol-5-yl]-2-(trifluoromethyl)benzamide

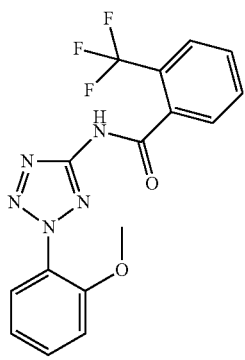 [SMILES: COc1ccccc1-n1nnc(NC(=O)c2ccccc2C(F)(F)F)n1]

(2-Methoxyphenyl)boronic acid (144 mg) was initially charged in N,N-dimethylformamide (1.5 ml), then N-(2H-tetrazol-5-yl)-2-(trifluoromethyl)benzamide (122 mg), copper(II) acetate (129 mg), pyridine (75 mg) and 3 Å molecular sieve (28 mg) were added successively, and then the mixture was stirred at room temperature for 48 h. The reaction mixture was filtered with suction through kieselguhr and concentrated to dryness under reduced pressure. The residue was taken up in ethyl acetate and washed with 1 N hydrochloric acid, and the organic phase was dried over sodium sulphate and concentrated to dryness under reduced pressure. The residue was chromatographed by preparative HPLC using the mobile phase water/acetonitrile (gradient=40 min from 10% acetonitrile in water to 100% acetonitrile). This gave 2.3 mg of the title compound. HPLC-MS: log P=2.19; mass (m/z): 364.1 (M+H)$^+$; $^1$H NMR (CD$_3$CN) 3.85 (s, 3H) 7.14-7.16 (m, 1H), 7.21-7.23 (m, 1H), 7.49-7.51 (m, 2H), 7.58-7.61 (m, 1H), 7.67-7.70 (m, 2H), 7.77-7.78 (m, 1H), 9.20 (s, 1H).

Example 8

N-[2-(4-Fluoro-2-methoxyphenyl)-2H-tetrazol-5-yl]-2-(trifluoromethyl)benzamide (Table 2, Example I-2-2)

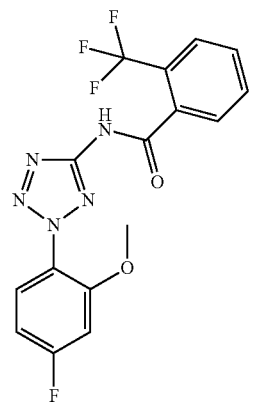 [SMILES: COc1cc(F)ccc1-n1nnc(NC(=O)c2ccccc2C(F)(F)F)n1]

(4-Fluoro-2-methoxyphenyl)boronic acid (74 mg) was initially charged in N,N-dimethylformamide (1.5 ml), then N-(2H-tetrazol-5-yl)-2-(trifluoromethyl)benzamide (61 mg), copper(II) acetate (59 mg), pyridine (35 mg) and 3 Å molecular sieve (28 mg) were added, and then the mixture was stirred at room temperature for 48 h. The reaction mixture was adsorbed on silica gel and first purified by column chromatography with water/1% formic acid/acetonitrile as eluent (gradient=15 min from 95% water to 100% acetonitrile) and then chromatographed again using preparative HPLC with water/1% formic acid/acetonitrile as eluent (gradient=40 min from 10% acetonitrile in water/1% formic acid to 100% acetonitrile). This gave 1.5 mg of the title compound. HPLC-MS: log P=2.35; mass (m/z): 382.2 (M+H)$^+$; $^1$H NMR (CD$_3$CN) 3.82 (s, 3H) 6.89-6.92 (m, 1H), 7.01-7.03 (m, 1H), 7.52-7.54 (m, 2H), 7.67-7.72 (m, 2H), 7.78-7.79 (m, 1H), 9.23 (s, 1H).

Example 9

N-(2-Phenyl-2H-tetrazol-5-yl)-2-(trifluoromethyl)benzamide (Table 2, Example I-2-3)

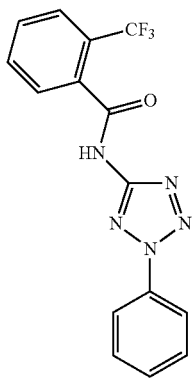 [SMILES: O=C(Nc1nnn(-c2ccccc2)n1)c1ccccc1C(F)(F)F]

2-Phenyl-2H-tetrazol-5-amine (150 mg) was initially charged in dichloromethane (4 ml), triethylamine (141 mg) and 2-(trifluoromethyl)benzoyl chloride (427 mg) were added at 0-5° C. and then the mixture was stirred at room temperature overnight. 5 ml of dichloromethane were added to the reaction mixture, which was then washed with water, and the organic phase was dried over sodium sulphate and concentrated to dryness under reduced pressure. The residue was purified by column chromatography with water/acetonitrile as eluent (gradient=30 min from 95% water to 100% acetonitrile). This gave 59.7 mg of the title compound. HPLC-MS: log P=2.57; mass (m/z): 334.0 (M+H)$^+$; $^1$H NMR (DMSO-$D_6$) 7.59-7.95 (m, 7H), 8.05-8.15 (m, 2H), 12.0 (s, 1H).

The compounds of the formulae (I-1) and (I-2) described in Tables 1 and 2 are likewise preferred compounds which were obtained according to or analogously to the examples described above.

TABLE 1

(I-1)

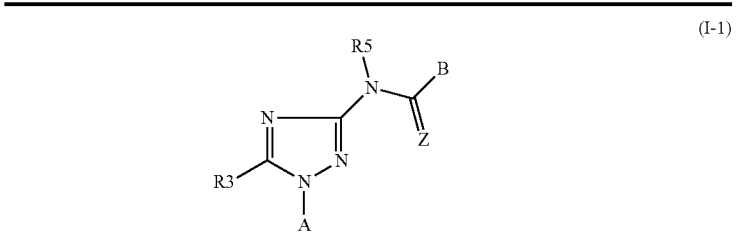

| Compound No. | A | B | R3 | R5 | Z |
|---|---|---|---|---|---|
| I-1-1 | 2-fluorophenyl | 2-chlorophenyl | H | H | O |
| I-1-2 | 2-fluorophenyl | 2-(trifluoromethyl)phenyl | H | H | O |
| I-1-3 | 2-chlorophenyl | 2-(trifluoromethyl)phenyl | H | H | O |
| I-1-4 | 2-chlorophenyl | 2-bromophenyl | H | H | O |
| I-1-5 | 2-chlorophenyl | 2-chlorophenyl | H | H | O |
| I-1-6 | 2-chlorophenyl | 2,6-difluorophenyl | H | H | O |
| I-1-7 | 2-(trifluoromethyl)phenyl | 2-chlorophenyl | H | H | O |
| I-1-8 | 2-(trifluoromethyl)phenyl | 2-(trifluoromethyl)phenyl | H | H | O |
| I-1-9 | 2-(trifluoromethoxy)phenyl | 2-chlorophenyl | H | H | O |
| I-1-10 | 2-(trifluoromethoxy)phenyl | 2-(trifluoromethyl)phenyl | H | H | O |
| I-1-11 | 2,6-difluorophenyl | 2-(trifluoromethyl)phenyl | H | H | O |
| I-1-12 | 2,6-difluorophenyl | 2-bromophenyl | H | H | O |
| I-1-13 | 2,6-difluorophenyl | 2-chlorophenyl | H | H | O |
| I-1-14 | 2,6-difluorophenyl | 2-methylphenyl | H | H | O |
| I-1-15 | 2,6-difluorophenyl | 2-ethylphenyl | H | H | O |
| I-1-16 | 2,6-difluorophenyl | 2-methoxyphenyl | H | H | O |
| I-1-17 | 2,6-difluorophenyl | 2-(trifluoromethoxy)phenyl | H | H | O |
| I-1-18 | 2,6-difluorophenyl | 2-(difluoromethyl)phenyl | H | H | O |
| I-1-19 | 2,6-difluorophenyl | 5-fluoro-2-(trifluoromethyl)phenyl | H | H | O |
| I-1-20 | 2,6-difluorophenyl | 2-fluoro-6-(trifluoromethyl)phenyl | H | H | O |
| I-1-21 | 2,6-difluorophenyl | 2-iodophenyl | H | H | O |
| I-1-22 | 2,6-difluorophenyl | 2-nitrophenyl | H | H | O |
| I-1-23 | 2,6-difluorophenyl | 2-chloropyridin-3-yl | H | H | O |
| I-1-24 | 2,6-difluorophenyl | 3-(trifluoromethyl)pyrazin-2-yl | H | H | O |
| I-1-26 | 2-fluoro-6-(trifluoromethyl)phenyl | 2-(trifluoromethyl)phenyl | H | H | O |
| I-1-27 | 2-fluoro-6-(trifluoromethyl)phenyl | 2-chlorophenyl | H | H | O |
| I-1-28 | 2-fluoro-6-(trifluoromethyl)phenyl | 2-iodophenyl | H | H | O |
| I-1-29 | 2-fluoro-6-(trifluoromethyl)phenyl | 2-ethylphenyl | H | H | O |
| I-1-30 | 2-bromo-6-fluorophenyl | 2-(trifluoromethyl)phenyl | H | H | O |
| I-1-31 | 2-bromo-6-fluorophenyl | 2-chlorophenyl | H | H | O |
| I-1-32 | 2-bromo-6-fluorophenyl | 2-iodophenyl | H | H | O |
| I-1-33 | 2-chloro-6-fluorophenyl | 2-(trifluoromethyl)phenyl | H | H | O |
| I-1-34 | 2-chloro-6-fluorophenyl | 2-(trifluoromethoxy)phenyl | H | H | O |

TABLE 1-continued

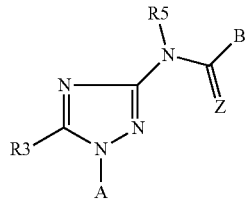

(I-1)

| Compound No. | A | B | R3 | R5 | Z |
|---|---|---|---|---|---|
| I-1-35 | 2-chloro-6-fluorophenyl | 2-iodophenyl | H | H | O |
| I-1-36 | 2-chloro-6-fluorophenyl | 2-chlorophenyl | H | H | O |
| I-1-37 | 2-fluoro-6-methylphenyl | 2-(trifluoromethyl)phenyl | H | H | O |
| I-1-38 | 2-fluoro-6-methylphenyl | 2-chlorophenyl | H | H | O |
| I-1-39 | 2-fluoro-6-methylphenyl | 2-iodophenyl | H | H | O |
| I-1-40 | 2-chloro-6-methylphenyl | 2-(trifluoromethyl)phenyl | H | H | O |
| I-1-41 | 2-chloro-6-methylphenyl | 2-chlorophenyl | H | H | O |
| I-1-42 | 2-chloro-6-ethylphenyl | 2-(trifluoromethyl)phenyl | H | H | O |
| I-1-43 | 2-chloro-6-ethylphenyl | 2-chlorophenyl | H | H | O |
| I-1-44 | 2,6-dichlorophenyl | 2-(trifluoromethyl)phenyl | H | H | O |
| I-1-45 | 2,6-dichlorophenyl | 2-bromophenyl | H | H | O |
| I-1-46 | 2,6-dichlorophenyl | 2-chlorophenyl | H | H | O |
| I-1-47 | 2,6-dimethylphenyl | 2-chlorophenyl | H | H | O |
| I-1-48 | 2,6-dimethylphenyl | 2-(trifluoromethyl)phenyl | H | H | O |
| I-149 | 2-methoxy-6-methylphenyl | 2-(trifluoromethyl)phenyl | H | H | O |
| I-1-50 | 2-methoxy-6-methylphenyl | 2-chlorophenyl | H | H | O |
| I-1-51 | 2,3-dichlorophenyl | 2-(trifluoromethyl)phenyl | H | H | O |
| I-1-52 | 2,3-dichlorophenyl | 2-chlorophenyl | H | H | O |
| I-1-53 | 2,4-dichlorophenyl | 2-(trifluoromethyl)phenyl | H | H | O |
| I-1-54 | 2,5-dichlorophenyl | 2-(trifluoromethyl)phenyl | H | H | O |
| I-1-55 | 2,5-dichlorophenyl | 2-chlorophenyl | H | H | O |
| I-1-57 | 2,3,6-trifluorophenyl | 2-(trifluoromethyl)phenyl | H | H | O |
| I-1-58 | 2,3,6-trifluorophenyl | 2-chlorophenyl | H | H | O |
| I-1-59 | 2,3,6-trifluorophenyl | 2-iodophenyl | H | H | O |
| I-1-60 | 2,3,6-trifluorophenyl | 2-ethylphenyl | H | H | O |
| I-1-61 | 2,4,6-trifluorophenyl | 2-(trifluoromethyl)phenyl | H | H | O |
| I-1-62 | 2,4,6-trifluorophenyl | 2-chlorophenyl | H | H | O |
| I-1-63 | 2,4,6-trifluorophenyl | 2-iodophenyl | H | H | O |
| I-1-64 | 2,4,6-trifluorophenyl | 2-ethylphenyl | H | H | O |
| I-1-65 | pentafluorophenyl | 2-(trifluoromethyl)phenyl | H | H | O |
| I-1-66 | pentafluorophenyl | 2-chlorophenyl | H | H | O |
| I-1-67 | pentafluorophenyl | 2-iodophenyl | H | H | O |
| I-1-68 | pentafluorophenyl | 2-ethylphenyl | H | H | O |
| I-1-70 | 2-bromophenyl | 2-(trifluoromethyl)phenyl | H | H | O |
| I-1-71 | 2-bromophenyl | 2-chlorophenyl | H | H | O |
| I-1-72 | 2-bromophenyl | 2-iodophenyl | H | H | O |
| I-1-73 | 2-bromophenyl | 2-ethylphenyl | H | H | O |
| I-1-75 | 2-iodophenyl | 2-(trifluoromethyl)phenyl | H | H | O |
| I-1-76 | 2-iodophenyl | 2-chlorophenyl | H | H | O |
| I-1-77 | 2-iodophenyl | 2-iodophenyl | H | H | O |
| I-1-78 | 2-iodophenyl | 2-ethylphenyl | H | H | O |
| I-1-80 | 2,6-dibromophenyl | 2-(trifluoromethyl)phenyl | H | H | O |
| I-1-81 | 2,6-dibromophenyl | 2-ethylphenyl | H | H | O |
| I-1-83 | 2-fluoro-6-iodophenyl | 2-(trifluoromethyl)phenyl | H | H | O |
| I-1-84 | 2-fluoro-6-iodophenyl | 2-chlorophenyl | H | H | O |
| I-1-85 | 2-fluoro-6-iodophenyl | 2-iodophenyl | H | H | O |
| I-1-87 | 2,6-dibromo-4-fluorophenyl | 2-(trifluoromethyl)phenyl | H | H | O |
| I-1-88 | 2,6-dibromo-4-fluorophenyl | 2-chlorophenyl | H | H | O |
| I-1-89 | 3,5-difluoropyridin-2-y1 | 2-(trifluoromethyl)phenyl | H | H | O |
| I-1-90 | 2,4-dimethyl-5-(2,2,2-trifluoroethylsulphinyl)phenyl | 2-(trifluoromethyl)phenyl | H | H | O |
| I-1-91 | 2,6-difluorophenyl | 3-(trifluoromethyl)-2-pyridyl | H | H | O |
| I-1-92 | 2,3,5,6-tetrafluorophenyl | 2-chlorophenyl | H | H | O |
| I-1-93 | 2,3,5,6-tetrafluorophenyl | 2-(trifluoromethyl)phenyl | H | H | O |
| I-1-94 | 2,6-difluorophenyl | 2-iodo-3-thienyl | H | H | O |
| I-1-95 | 2-(trifluoromethyl)phenyl | 2-ethylphenyl | H | H | O |
| I-1-96 | 2,4-dimethyl-5-(2,2,2-trifluoroethylsulphonyl)phenyl | 2-(trifluoromethyl)phenyl | H | H | O |
| I-1-97 | 2,3,5-trifluorophenyl | 2-iodophenyl | H | H | O |
| I-1-98 | 2,4-dimethyl-5-(2,2,2-trifluoroethylsulphanyl)phenyl | 2-(trifluoromethyl)phenyl | H | H | O |

TABLE 2

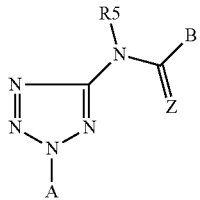

(I-2)

| Compound No. | A | B | R5 | Z |
|---|---|---|---|---|
| I-2-1 | 2-methoxyphenyl | 2-(trifluoromethyl)phenyl | H | O |
| I-2-2 | 2-methoxy-4-fluorophenyl | 2-(trifluoromethyl)phenyl | H | O |
| I-2-3 | phenyl | 2-(trifluoromethyl)phenyl | H | O |

HPLC-MS[1)] and $^1$H NMR data[2)]

| Compound No. | log P neutral | $^1$H NMR data |
|---|---|---|
| I-1-1 | 1.88 | 1H NMR (400.0 MHz, d6-DMSO): δ = 13.376 (0.4); 11.249 (9.8); 8.902 (4.2); 8.316 (0.6); 7.797 (1.5); 7.574 (4.1); 7.557 (11.7); 7.536 (16.0); 7.526 (8.6); 7.503 (6.1); 7.483 (3.0); 7.457 (4.6); 7.440 (7.7); 7.421 (6.0); 4.038 (0.5); 4.020 (0.7); 3.322 (67.1); 2.675 (1.6); 2.670 (2.2); 2.666 (1.6); 2.524 (6.6); 2.510 (129.2); 2.506 (257.8); 2.501 (336.7); 2.497 (243.3); 2.493 (117.8); 2.333 (1.6); 2.328 (2.2); 2.324 (1.6); 1.989 (2.0); 1.398 (1.6); 1.192 (0.5); 1.175 (1.1); 1.157 (0.5); 0.146 (0.6); 0.008 (5.3); 0.000 (148.8); −0.009 (5.3); −0.150 (0.6) |
| I-1-2 | 2.06 | 1H NMR (400.0 MHz, δ-DMSO): δ = 13.578 (5.8); 11.334 (8.4); 8.915 (4.8); 7.849 (11.3); 7.830 (16.0); 7.802 (9.4); 7.783 (7.6); 7.768 (9.4); 7.746 (7.6); 7.725 (10.0); 7.707 (11.0); 7.615 (0.8); 7.555 (8.3); 7.536 (10.6); 7.422 (5.0); 5.758 (9.4); 3.330 (11.7); 2.999 (0.8); 2.714 (0.8); 2.676 (1.1); 2.671 (1.4); 2.667 (1.0); 2.507 (171.8); 2.502 (215.8); 2.498 (158.1); 2.334 (1.1); 2.329 (1.4); 2.325 (1.0); 1.234 (0.4); 0.008 (2.5); 0.000 (43.7); −0.008 (2.1) |
| I-1-3 | 2.10 | 1H NMR (400.0 MHz, d6-DMSO): δ = 11.300 (7.0); 8.874 (6.1); 8.838 (1.2); 8.317 (0.4); 7.911 (0.5); 7.893 (0.6); 7.841 (7.4); 7.823 (9.7); 7.759 (12.1); 7.748 (11.3); 7.704 (16.0); 7.581 (13.1); 7.457 (0.5); 7.452 (0.5); 7.439 (0.5); 7.393 (0.4); 7.364 (0.3); 6.264 (0.5); 4.038 (0.4); 4.020 (0.4); 3.326 (89.6); 3.090 (0.5); 3.072 (0.5); 2.679 (0.5); 2.675 (1.0); 2.671 (1.3); 2.666 (0.9); 2.661 (0.4); 2.524 (4.0); 2.519 (6.3); 2.510 (72.2); 2.506 (144.2); 2.501 (190.8); 2.497 (138.3); 2.492 (66.0); 2.506 (0.6); 2.337 (0.4); 2.333 (0.9); 2.328 (1.3); 2.324 (0.9); 2.319 (0.4); 2.224 (0.3); 2.050 (2.1); 1.989 (1.9); 1.192 (0.8); 1.188 (1.4); 1.174 (1.5); 1.170 (2.8); 1.157 (0.8); 1.152 (1.4); 0.008 (2.0); 0.000 (57.8); −0.009 (1.8) |
| I-1-4 | 1.97 | 1H NMR (400.0 MHz, d6-DMSO): δ = 13.388 (3.7); 11.202 (4.9); 8.857 (3.3); 8.437 (1.2); 8.316 (0.6); 7.759 (4.1); 7.746 (10.8); 7.741 (11.9); 7.726 (14.1); 7.723 (16.0); 7.707 (13.8); 7.703 (14.4); 7.684 (5.9); 7.661 (1.6); 7.656 (1.4); 7.626 (2.0); 7.622 (2.2); 7.606 (3.5); 7.602 (4.1); 7.596 (5.9); 7.591 (7.1); 7.580 (8.9); 7.572 (7.0); 7.547 (3.4); 7.529 (3.3); 7.490 (5.7); 7.486 (6.1); 7.472 (13.2); 7.468 (12.3); 7.453 (15.6); 7.449 (11.2); 7.447 (10.8); 7.433 (9.1); 7.428 (9.5); 7.415 (4.9); 7.410 (5.3); 7.388 (2.0); 7.377 (1.5) 7.373 (1.3); 7.359 (1.4); 7.357 (1.4); 7.353 (1.6); 7.348 (0.6); 7.345 (0.5); 7.338 (1.3); 7.334 (1.2); 7.330 (0.5); 7.243 (1.1); 7.240 (1.1); 7.224 (1.3); 7.220 (1.4); 7.205 (0.8); 7.201 (0.7); 6.971 (1.5); 6.968 (1.5); 6.951 (1.4); 6.947 (1.3); 5.756 (0.9); 5.624 (0.8); 3.859 (0.4); 3.506 (0.5); 3.323 (49.0); 2.753 (0.3); 2.680 (0.8); 2.675 (1.7); 2.671 (2.3); 2.666 (1.6); 2.662 (0.8); 2.524 (7.8); 2.511 (130.0); 2.506 (256.8); 2.502 (336.5); 2.497 (242.5); 2.493 (115.9); 2.337 (0.8); 2.333 (1.7); 2.328 (2.3); 2.324 (1.7); 1.234 (1.2); 1.223 (0.4); 0.146 (0.8); 0.008 (7.4); 0.000 (191.7); −0.009 (6.2); −0.150 (0.8) |
| I-1-5 | 1.91 | 1H NMR (400.0 MHz, d6-DMSO): δ = 11.214 (7.8); 8.857 (5.4); 8.317 (0.4); 7.759 (5.9); 7.741 (7.2); 7.691 (3.2); 7.610 (3.8); 7.597 (9.3); 7.591 (11.0); 7.580 (16.0); 7.572 (12.8); 7.551 (9.4); 7.531 (9.7); 7.512 (5.3); 7.494 (7.1); 7.475 (4.0); 7.449 (5.6); 7.432 (6.6); 7.414 (2.8); 3.326 (140.3); 2.680 (0.4); 2.675 (0.9); 2.670 (1.2); 2.666 (0.9); 2.661 (0.4); 2.524 (3.7); 2.519 (5.8); 2.510 (68.9); 2.506 (137.5); 2.501 (180.8); 2.497 (130.3); 2.492 (61.2); 2.337 (0.4); 2.333 (0.9); 2.328 (1.2); 2.324 (0.8); 2.319 (0.4); 1.989 (1.2); 1.397 (0.5); 1.192 (0.3); 1.174 (0.7); 1.157 (0.3); 0.008 (1.6); 0.000 (48.0); −0.009 (1.4) |
| I-1-6 | 1.90 | 1H NMR (400.0 MHz, d6-DMSO): δ = 11.550 (0.8); 8.893 (1.1); 7.771 (0.4); 7.753 (0.6); 7.735 (0.5); 7.714 (0.6); 7.623 (0.7); 7.605 (1.2); 7.589 (1.3); 7.584 (1.5); 7.579 (1.1); 7.568 (0.8); 7.563 (0.8); 7.546 (0.4); 7.253 (0.6); 7.244 (0.4); 7.232 (1.2); 7.224 (1.5); 7.212 (0.7); 7.204 (1.8); 7.183 (0.8); 3.334 (0.9); 3.098 (0.8); 3.082 (2.3); 3.064 (2.3); 3.049 (0.8); 2.525 (0.6); 2.511 (13.4); 2.507 (26.5); 2.503 (34.4); 2.498 (24.7); 2.494 (11.8); 1.207 (7.9); 1.189 (16.0); 1.171 (7.5); 0.008 (0.8); 0.000 (22.1); −0.009 (0.7) |
| I-1-7 | 2.06 | 1H NMR (400.0 MHz, d6-DMSO): δ = 11.193(13.0); 8.766(10.3); 8.317(0.6); 8.014 (12.7); 7.995(15.4); 7.936(5.8); 7.917(14.0); 7.898(10.4); 7.848(11.7); 7.829(16.0); 7.810(7.0); 7.763(6.1); 7.546(10.9); 7.525(14.9); 7.507(9.5); 7.489(11.8); 7.470(6.7); 7.442(8.8); 7.425 (10.5); 7.408(4.8); 4.038(1.0); 4.020(1.0); 4.002(0.3); 3.374(0.4); 3.329(376.9); 2.675(1.2); 2.671(1.7); 2.666(1.3); 2.510(101.4); 2.506(196.6); 2.502(255.0); 2.497(185.4); 2.333(1.3); 2.328 (1.7); 2.324(1.2); 1.989(4.1); 1.192(1.1); 1.175(2.1); 1.157(1.0); 0.146(1.6); 0.008(14.7); 0.000(330.8); −0.008(13.9); −0.030(0.4); −0.150(1.6) |
| I-1-8 | 2.24 | 1H NMR (400.0 MHz, d6-DMSO): δ = 13.583(0.4); 11.271(6.8); 8.781(6.7); 8.317(1.2); 8.014(6.5); 7.996(7.7); 7.918(7.9); 7.900(6.5); 7.828(16.0); 7.770(11.4); 7.699(12.4); 4.056 (0.9); 4.038(2.7); 4.020(2.7); 4.002(0.9); 3.326(281.6); 2.680(0.9); 2.675(1.8); 2.671(2.5); 2.666 (1.8); 2.524(7.5); 2.511(143.8); 2.506(285.0); 2.502(372.8); 2.497(268.6); 2.493(128.5); 2.333 (1.8); 2.328(2.5); 2.324(1.8); 2.320(0.8); 1.989(11.8); 1.236(0.9); 1.193(3.2); 1.175(6.3); 1.157(3.1); 0.146(2.5); 0.008(23.0); 0.000(543.3); −0.009(20.1); −0.150(2.4) |
| I-1-9 | 2.32 | 1H NMR (400.0 MHz, d6-DMSO): δ = 11.237(11.8); 8.924(0.3); 8.869(6.7); 8.436(0.8); 8.317(0.4); 7.815(3.1); 7.765(2.5); 7.746(2.4); 7.734(1.0); 7.698(3.9); 7.679(16.0); 7.661(12.7); |

| Compound No. | log P neutral | ¹H NMR data |
|---|---|---|
| | | 7.657(11.7); 7.643(10.6); 7.628(7.8); 7.610(3.7); 7.554(7.8); 7.531(11.3); 7.520(9.1); 7.497 (8.7); 7.478(4.7); 7.451(6.4); 7.434(8.8); 7.415(4.9); 7.399(1.4); 7.394(1.2); 5.705(0.7); 4.056 (0.3); 4.038(1.0); 4.020(1.0); 4.003(0.3); 3.328(53.3); 2.676(0.9); 2.671(1.2); 2.667(0.9); 2.507 (143.1); 2.502(181.9); 2.498(133.6); 2.333(0.9); 2.329(1.2); 2.325(0.9); 2.180(0.4); 1.989 (4.4); 1.236(5.8); 1.193(1.2); 1.175(2.3); 1.157(1.2); 0.854(0.6); 0.146(1.2); 0.008(12.0); 0.000 (243.9); −0.008(11.6); −0.150(1.2) |
| I-1-10 | 2.51 | 1H NMR (400.0 MHz, d6-DMSO): δ = 13.582(0.5); 11.314(6.1); 8.881(4.7); 8.436(4.3); 8.317(0.8); 7.840(10.6); 7.823(12.1); 7.789(6.1); 7.774(6.4); 7.758(7.4); 7.738(6.7); 7.734(7.6); 7.714(12.2); 7.700(12.3); 7.678(16.0); 7.660(12.5); 7.643(9.8); 7.612(4.0); 7.608(3.9); 7.592 (2.2); 7.588(2.4); 7.572(1.3); 7.568(1.4); 7.554(2.3); 7.549(1.4); 7.535(1.9); 7.531(2.3); 7.526 (2.0); 7.512(1.6); 7.507(1.5); 7.493(0.8); 7.488(0.7); 7.455(0.4); 7.435(0.4); 5.705(3.3); 4.056 (0.4); 4.038(1.2); 4.020(1.2); 4.003(0.4); 3.328(217.3); 2.999(1.0); 2.714(1.0); 2.676(1.5); 2.671(2.1); 2.667(1.5); 2.511(120.0); 2.507(233.7); 2.502(303.8); 2.498(219.9); 2.493(106.7); 2.333(1.5); 2.329(2.0); 2.325(1.4); 1.989(5.2); 1.236(1.8); 1.193(1.4); 1.175(2.7); 1.157(1.3); 0.146(2.0); 0.008(19.6); 0.000(423.5); −0.008(16.5); −0.150(2.0) |
| I-1-11 | 1.97 | See Synthesis Example 2 |
| I-1-12 | 1.80 | 1H NMR (400.0 MHz, d6-DMSO): δ = 13.375(0.8); 11.262(4.1); 8.937(0.5); 8.891(2.6); 8.403(0.3); 8.004(0.4); 7.986(0.4); 7.983(0.5); 7.978(1.2); 7.975(1.4); 7.958(2.1); 7.954(1.6); 7.940(0.7); 7.937(0.6); 7.750(4.7); 7.745(4.9); 7.731(6.4); 7.727(8.7); 7.710(8.6); 7.706(8.5); 7.697(3.4); 7.691(3.9); 7.677(2.1); 7.658(1.1); 7.643(0.6); 7.640(0.8); 7.637(0.5); 7.626(0.5); 7.611(0.6); 7.608(0.5); 7.592(0.6); 7.582(0.5); 7.548(3.0); 7.545(2.8); 7.529(3.2); 7.510(1.5); 7.502(1.7); 7.492(3.7); 7.489(4.2); 7.474(10.2); 7.470(8.1); 7.456(16.0); 7.452(9.8); 7.436(8.2); 7.431(8.5); 7.417(3.1); 7.412(3.9); 7.391(1.4); 7.364(0.6); 5.758(2.4); 5.667(0.4); 4.346(0.8); 4.328(2.4); 4.310(2.4); 4.292(0.8); 3.329(5.6); 2.676(0.4); 2.672(0.5); 2.667(0.4); 2.525(1.9); 2.511(28.9); 2.507(55.7); 2.503(72.0); 2.498(52.6); 2.494(25.8); 2.334(0.3); 2.329(0.5); 2.086 (9.8); 1.342(2.5); 1.324(5.0); 1.307(2.4); 1.235(0.6); 0.008(2.0); 0.000(43.6); −0.009(1.6) |
| I-1-13 | 1.73 | See Synthesis Example 6 |
| I-1-14 | 1.72 | 1H NMR (400.0 MHz, d6-DMSO): δ = 10.974(3.4); 8.889(4.5); 7.750(0.4); 7.734(0.9); 7.729(0.8); 7.713(1.7); 7.696(1.0); 7.691(1.1); 7.675(0.5); 7.490(2.0); 7.478(3.6); 7.457(4.8); 7.436(2.3); 7.407(0.8); 7.387(2.1); 7.370(1.7); 7.300(3.5); 7.280(3.3); 7.259(1.0); 3.329(14.8); 2.506(28.2); 2.502(34.1); 2.395(16.0); 0.000(10.6) |
| I-1-15 | 2.05 | See Synthesis Example 3 |
| I-1-16 | 1.91 | 1H NMR (400.0 MHz, d6-DMSO): δ = 10.599(9.4); 8.884(7.5); 7.749(1.0); 7.733(2.1); 7.728(2.1); 7.712(4.3); 7.695(3.0); 7.690(4.6); 7.674(3.0); 7.667(3.2); 7.546(2.0); 7.542(2.0); 7.524(4.1); 7.507(2.6); 7.503(2.5); 7.477(6.5); 7.455(11.2); 7.435(5.3); 7.193(4.2); 7.172(3.8); 7.088(3.4); 7.069(6.2); 7.050(3.0); 3.905(16.0); 3.808(0.8); 3.325(60.7); 2.671(0.6); 2.506 (68.4); 2.502(88.1); 2.498(67.4); 2.329(0.6); 1.989(0.9); 1.175(0.5); 0.008(1.9); 0.000(39.6) |
| I-1-17 | 2.14 | 1H NMR (400.0 MHz, d6-DMSO): δ = 13.413(0.3); 11.259(9.9); 8.895(6.5); 7.934(0.9); 7.929(0.9); 7.914(1.0); 7.910(1.0); 7.750(1.5); 7.733(3.6); 7.728(4.3); 7.712(9.7); 7.696(7.8); 7.691(6.8); 7.675(2.6); 7.667(3.0); 7.647(6.0); 7.628(4.2); 7.539(1.3); 7.526(5.1); 7.507(7.8); 7.487(8.5); 7.476(11.3); 7.455(16.0); 7.434(7.1); 3.330(93.5); 2.676(0.5); 2.672(0.7); 2.667 (0.5); 2.525(1.8); 2.511(39.1); 2.507(76.7); 2.503(99.5); 2.498(72.4); 2.494(35.4); 2.334(0.5); 2.330(0.7); 2.325(0.5); 1.989(1.2); 1.193(0.3); 1.175(0.6); 0.008(1.8); 0.000(48.0); −0.008 (1.9) |
| I-1-18 | 1.92 | 1H NMR (400.0 MHz, d6-DMSO): δ = 13.538(0.5); 11.365(9.6); 8.922(14.4); 8.316(0.9); 7.993(1.6); 7.974(1.8); 7.795(3.3); 7.778(4.6); 7.768(7.1); 7.765(7.2); 7.747(8.1); 7.740(5.2); 7.735(4.6); 7.724(2.6); 7.718(9.0); 7.713(5.4); 7.697(9.5); 7.681(10.7); 7.677(8.5); 7.663(4.9); 7.614(2.3); 7.483(9.7); 7.475(2.1); 7.462(16.0); 7.441(7.7); 7.315(8.7); 7.176(4.3); 4.038(0.4); 4.020(0.4); 3.325(156.8); 2.675(1.5); 2.671(2.0); 2.666(1.5); 2.524 (5.5); 2.511(111.9); 2.506(228.6); 2.502(303.6); 2.497(220.4); 2.493(106.3); 2.333(1.4); 2.328 (2.0); 2.324(1.4); 1.989(1.8); 1.277(0.6); 1.235(0.7); 1.193(0.5); 1.175(1.0); 1.157(0.5); 0.146 (1.8); 0.022(0.7); 0.008(14.8); 0.000(407.7); −0.009(14.6); −0.021(0.7); −0.150(1.7) |
| I-1-19 | 2.09 | 1H NMR (400.0 MHz, d6-DMSO): δ = 11.480(11.4); 8.918(11.1); 7.922(7.8); 7.717(12.7); 7.700(11.4); 7.558(7.9); 7.482(10.1); 7.461(16.0); 7.440(9.3); 4.056(1.0); 4.038(2.9); 4.020 (2.9); 4.003(1.0); 3.331(49.8); 2.992(1.1); 2.738(1.1); 2.672(1.1); 2.503(162.3); 2.330(1.1); 1.989 (11.8); 1.236(2.5); 1.193(3.3); 1.175(6.2); 1.157(3.1); 0.000(30.9) |
| I-1-20 | 2.04 | 1H NMR (400.0 MHz, d6-DMSO): δ = 11.644(10.9); 11.579(2.0); 8.926(16.0); 8.666(2.9); 8.317(0.8); 7.790(1.0); 7.769(2.9); 7.761(2.9); 7.750(6.3); 7.745(6.0); 7.738(10.7); 7.729(3.6); 7.723(7.9); 7.714(14.2); 7.702(6.0); 7.691(5.2); 7.666(1.1); 7.650(1.3); 7.629(1.4); 7.607(2.6); 7.586(1.5); 7.561(1.3); 7.540(0.6); 7.488(8.3); 7.467(14.1); 7.446(6.7); 7.376(1.6); 7.355 (2.7); 7.334(1.3); 4.056(0.6); 4.038(1.9); 4.020(1.9); 4.002(0.6); 3.891(0.5); 3.857(0.4); 3.329 (235.0); 2.676(1.4); 2.671(1.9); 2.667(1.4); 2.524(5.9); 2.511(120.1); 2.507(233.7); 2.502(299.7); 2.498(217.0); 2.494(107.6); 2.333(1.4); 2.329(1.9); 2.325(1.4); 1.989(8.1); 1.243(2.4); 1.236(1.3); 1.193(2.2); 1.175(4.5); 1.157(2.2); 0.146(0.6); 0.008(5.5); 0.000(136.1); −0.008 (6.8); −0.150(0.6) |
| I-1-21 | 1.89 | 1H NMR (400.0 MHz, d6-DMSO): δ = 13.285(0.7); 11.196(5.8); 11.040(0.4); 8.935(0.6); 8.887(3.6); 8.001(0.7); 7.991(4.5); 7.972(4.7); 7.956(0.6); 7.927(3.8); 7.908(4.0); 7.751(0.8); 7.735(1.9); 7.730(1.9); 7.714(6.6); 7.696(5.8); 7.693(5.9); 7.677(1.1); 7.611(0.4); 7.544(0.6); 7.524(1.0); 7.494(5.5); 7.478(16.0); 7.457(12.0); 7.436(4.4); 7.250(2.5); 7.231(5.6); 7.216(4.2); 7.212(3.8); 7.197(1.4); 5.757(3.7); 3.325(18.8); 2.675(0.8); 2.671(1.1); 2.666(0.8); 2.506 (124.6); 2.502(156.0); 2.497(114.6); 2.333(0.8); 2.328(1.0); 2.324(0.7); 1.324(0.4); 1.235(0.3); 0.000(62.9); −0.008(2.9) |
| I-1-22 | 1.54 | 1H NMR (400.0 MHz, d6-DMSO): δ = 11.516(7.5); 8.915(6.3); 8.401(0.4) 8.317(0.7); 8.163(14.3); 8.142(16.0); 7.981(1.3); 7.961(1.4); 7.938(0.5); 7.858(8.6); 7.842(8.3); 7.809(3.0); 7.772(11.7); 7.765(11.8); 7.752(12.1); 7.613(0.8); 7.592(0.8); 7.544(0.8); 7.459(12.5); 7.365(1.0); 5.757(7.1); 5.667(0.4); 3.329(209.4); |

| Compound No. | log P neutral | $^1$H NMR data |
|---|---|---|
| | | 3.018(0.4); 2.800(0.4); 2.671(2.2); 2.506(269.5); 2.502(333.5); 2.498(251.1); 2.329(2.2); 2.057(1.4); 1.234(0.5); 0.000(27.8) |
| I-1-23 | 1.24 | 1H NMR (400.0 MHz, d6-DMSO): δ = 11.481(3.3); 8.919(1.5); 8.517(2.0); 8.076(1.3); 7.732(1.0); 7.716(1.5); 7.697(1.2); 7.540(1.8); 7.501(0.5); 7.479(2.2); 7.458(3.6); 7.436(1.9); 5.757(16.0); 3.327(39.3); 2.676(0.4); 2.671(0.6); 2.667(0.4); 2.525(1.6); 2.511(34.8); 2.507 (68.2); 2.502(87.5); 2.498(62.0); 2.494(29.3); 2.333(0.4); 2.329(0.6); 2.325(0.4); 0.008(0.4); 0.000 (10.3); −0.009(0.4) |
| I-1-24 | 1.73 | 1H NMR (400.0 MHz, d6-DMSO): δ = 11.839(3.6); 11.663(12.6); 9.140(0.4); 9.098(12.5); 9.081(3.7); 9.040(12.6); 9.015(3.5); 9.010(3.7); 8.966(16.0); 8.927(8.5); 8.845 (0.9); 8.831(1.4); 8.663(3.9); 8.401(2.8); 8.365(1.8); 8.358(1.9); 8.317(1.2); 8.238(2.0); 8.231 (1.9); 8.028(0.4); 8.005(0.7); 7.983(0.6); 7.766(1.3); 7.746(3.5); 7.729(5.8); 7.710(4.4); 7.692 (2.2); 7.664(1.4); 7.646(2.1); 7.629(2.7); 7.614(2.7); 7.593(2.3); 7.576(1.2); 7.571(1.5); 7.555 (1.0); 7.531(0.7); 7.494(9.0); 7.473(15.8); 7.452(8.2); 7.386(5.1); 7.364(7.6); 7.344(4.0); 7.204 (0.4); 6.414(0.5); 5.757(10.1); 5.667(3.4); 4.454(0.4); 4.436(0.4); 4.408(1.7); 4.391(3.3); 4.375 (1.7); 3.529(0.3); 3.506(0.8); 3.469(0.4); 3.432(0.6); 3.420(0.6); 3.375(3.8); 3.330(363.4); 3.279(2.0); 3.263(3.1); 3.247(3.0); 3.229(1.4); 2.676(2.6); 2.672(3.3); 2.668(2.6); 2.507(377.2); 2.503(466.9); 2.499(350.4); 2.435(2.8); 2.421(2.1); 2.407(2.8); 2.330(3.0); 1.798(0.3); 1.783 (0.7); 1.766(0.9); 1.749(0.8); 1.732(0.6); 1.710(0.8); 1.693(2.1); 1.675(3.4); 1.657(3.8); 1.646 (3.2); 1.630(3.9); 1.613(2.8); 1.596(1.3); 1.551(3.5); 1.538(3.1); 1.355(0.8); 1.348(1.0); 1.331 (0.9); 1.312(0.5); 1.235(1.6); 1.204(0.5); 0.928(11.5); 0.911(11.4); 0.895(1.3); 0.880(1.2); 0.855(0.8); 0.839(0.6); 0.000(27.0) |
| I-1-26 | 2.25 | 1H NMR (400.0 MHz, d6-DMSO): δ = 11.334(7.2); 8.865(7.2); 8.318(0.7); 7.950(11.9); 7.935(16.0); 7.890(10.4); 7.834(8.2); 7.818(9.7); 7.753(8.6); 7.716(12.5); 4.056(0.9); 4.038 (2.6); 4.020(2.7); 4.002(0.9); 3.332(356.1); 2.999(0.7); 2.714(0.7); 2.680(0.5); 2.676(1.1); 2.671 (1.6); 2.667(1.2); 2.662(0.6); 2.525(3.1); 2.520(4.8); 2.511(82.9); 2.507(176.1); 2.502(237.5); 2.498(173.0); 2.493(83.6); 2.338(0.5); 2.334(1.1); 2.329(1.6); 2.324(1.1); 1.989(11.7); 1.236 (1.5); 1.192(3.2); 1.175(6.3); 1.157(3.1); 0.000(1.2) |
| I-1-27 | 2.06 | 1H NMR (400.0 MHz, d6-DMSO): δ = 11.251(6.2); 8.847(5.9); 8.341(1.5); 8.316(1.3); 7.968(1.8); 7.953(10.8); 7.936(16.0); 7.926(10.1); 7.922(10.5); 7.891(8.8); 7.845(0.7); 7.837 (1.2); 7.823(0.8); 7.810(1.1); 7.803(1.1); 7.791(0.3); 7.785(0.3); 7.571(4.4); 7.543(5.0); 7.524 (8.0); 7.507(5.9); 7.489(7.0); 7.471(4.0); 7.441(5.2); 7.423(6.3); 5.624(1.9); 4.055(0.6); 4.038 (1.7); 4.020(1.7); 4.002(0.6); 3.390(0.3); 3.375(0.5); 3.330(711.4); 3.296(0.8); 2.680(0.9); 2.676 (2.0); 2.671(2.8); 2.666(2.1); 2.524(5.9); 2.520(8.9); 2.511(149.4); 2.507(316.0); 2.502(424.9); 2.497(307.8); 2.493(147.7); 2.338(0.9); 2.333(2.0); 2.329(2.8); 2.324(2.1); 2.320(1.0); 1.989 (7.6); 1.336(0.5); 1.193(2.1); 1.175(4.2); 1.157(2.1); 0.000(2.1) |
| I-1-28 | 2.21 | See Synthesis Example 4 |
| I-1-29 | 2.39 | 1H NMR (400.0 MHz, d6-DMSO): δ = 10.977(3.7); 8.840(5.6); 8.340(0.4); 7.971(0.5); 7.954(3.2); 7.936(5.3); 7.928(3.0); 7.922(2.9); 7.893(3.0); 7.886(2.4); 7.879(1.4); 7.874(1.3); 7.869(1.4); 7.455(1.9); 7.436(2.3); 7.432(2.3); 7.411(3.0); 7.392(2.2); 7.329(3.9); 7.311(2.8); 7.289(2.0); 7.270(3.0); 7.252(1.3); 5.625(0.5); 3.330(58.0); 2.921(1.3); 2.902(0.6); 2.770(1.7); 2.751(5.3); 2.732(5.4); 2.713(1.9); 2.671(0.4); 2.506(45.1); 2.502(57.9); 2.498(44.2); 2.329 (0.4); 1.989(0.5); 1.193(7.5); 1.174(16.0); 1.155(7.7); 1.133(0.8); 0.000(20.7) |
| I-1-30 | 2.15 | See Synthesis Example 1 |
| I-1-31 | 1.95 | 1H NMR (400.0 MHz, d6-DMSO): δ = 11.263(1.4); 8.849(1.4); 8.316(0.3); 7.777(1.6); 7.759(2.0); 7.667(0.6); 7.645(1.7); 7.627(3.3); 7.611(1.9); 7.602(2.3); 7.582(1.5); 7.548(1.3); 7.528(2.0); 7.510(1.3); 7.491(1.6); 7.472(0.9); 7.446(1.3); 7.428(1.6); 7.411(0.7); 4.055(1.2); 4.038(3.7); 4.020(3.7); 4.002(1.2); 3.325(91.6); 2.675(0.5); 2.671(0.7); 2.666(0.5); 2.524(2.2); 2.510(43.7); 2.506(86.0); 2.502(111.7); 2.497(80.4); 2.493(38.6); 2.333(0.5); 2.328(0.7); 2.324 (0.5); 1.989(16.0); 1.193(4.3); 1.175(8.5); 1.157(4.2); 0.146(0.4); 0.008(3.6); 0.000(89.8); −0.009(3.3); −0.150(0.4) |
| I-1-32 | 2.08 | 1H NMR (400.0 MHz, d6-DMSO): δ = 11.183(8.0); 8.845(7.1); 8.346(0.6); 8.316(0.9); 7.923(7.2); 7.904(7.4); 7.778(7.6); 7.760(9.6); 7.734(0.7); 7.714(0.7); 7.698(0.6); 7.693(0.6); 7.685(0.7); 7.667(2.9); 7.646(8.1); 7.628(16.0); 7.612(8.2); 7.605(9.5); 7.601(9.1); 7.583(2.9); 7.565(0.6); 7.549(0.8); 7.541(0.9); 7.533(1.2); 7.482(12.3); 7.474(12.2); 7.232(3.5); 7.221 (5.6); 7.212(5.5); 7.202(5.2); 7.192(2.8); 5.756(10.6); 5.604(0.6); 3.323(113.9); 2.675(1.6); 2.670 (2.1); 2.666(1.6); 2.523(6.5); 2.510(118.6); 2.506(236.2); 2.501(309.2); 2.497(223.4); 2.492 (107.3); 2.337(0.7); 2.333(1.4); 2.328(2.0); 2.324(1.4); 1.989(0.9); 1.398(0.4); 1.259(0.5); 1.235(1.8); 1.193(0.4); 1.175(0.6); 1.157(0.3); 0.853(0.3); 0.146(1.4); 0.008(12.2); 0.000(313.6); −0.009(11.4); −0.150(1.4) |
| I-1-33 | 2.10 | 1H NMR (400.0 MHz, d6-DMSO): δ = 13.578(4.8); 11.347(5.7); 8.878(5.4); 8.317(0.7); 7.846(6.8); 7.831(9.5); 7.827(9.9); 7.821(8.9); 7.798(7.4); 7.780(6.3); 7.766(9.7); 7.762(9.1); 7.747(9.3); 7.743(10.2); 7.720(16.0); 7.704(15.0); 7.656(8.4); 7.636(5.7); 7.609(5.2); 7.587 (6.8); 7.566(3.8); 7.453(0.3); 5.757(2.2); 3.324(81.6); 2.998(0.8); 2.714(0.8); 2.680(0.9); 2.675 (1.8); 2.671(2.5); 2.666(1.8); 2.662(0.9); 2.524(9.0); 2.511(142.5); 2.506(282.3); 2.502(369.4); 2.497(264.7); 2.493(125.9); 2.338(0.9); 2.333(1.8); 2.328(2.5); 2.324(1.8); 1.234(0.4); 0.146 (0.5); 0.008(4.8); 0.000(125.4); −0.008(4.1); −0.150(0.5) |
| I-1-34 | 2.30 | 1H NMR (400.0 MHz, d6-DMSO): δ = 13.416(0.8); 11.247(9.9); 8.866(8.7); 8.317(1.5); 7.923(2.9); 7.919(2.9); 7.904(3.2); 7.900(3.1); 7.738(3.9); 7.717(14.4); 7.702(15.9); 7.697(16.0); 7.682(11.0); 7.652(16.0); 7.641(10.5); 7.622(7.2); 7.608(7.7); 7.585(10.9); 7.564 (4.9); 7.533(3.7); 7.517(9.1); 7.501(11.0); 7.481(12.7); 7.460(7.9); 4.038(0.7); 4.020(0.7); 3.327 (394.7); 3.000(0.5); 2.775(0.4); 2.680(1.2); 2.676(2.5); 2.671(3.4); 2.667(2.4); 2.662(1.2); 2.524(9.0); 2.511(193.6); 2.507(386.9); 2.502(506.7); 2.497(364.8); 2.493(173.7); 2.333(2.4); 2.329(3.3); 2.324(2.4); 2.237(0.3); 1.989(3.0); 1.236(1.2); 1.193(0.8); 1.175(1.6); 1.157(0.8); 0.146(1.0); 0.008(7.7); 0.000(222.8); −0.008(7.5); −0.150(0.9) |
| I-1-35 | 2.04 | 1H NMR (400.0 MHz, d6-DMSO): δ = 11.188(1.7); 8.858(1.5); 7.923(1.5); 7.904(1.5); 7.739(0.6); 7.718(1.5); 7.703(1.6); 7.697(1.4); 7.683(1.3); 7.652(2.4); 7.632(1.4); 7.608(1.3); |

-continued

| Compound No. | log P neutral | ¹H NMR data |
|---|---|---|
| | | 7.585(2.0); 7.565(0.9); 7.483(2.6); 7.475(2.6); 7.232(0.7); 7.222(1.2); 7.214(1.2); 7.203(1.1); 4.055(0.8); 4.038(2.4); 4.020(2.5); 4.002(0.8); 3.324(18.2); 2.670(0.3); 2.524(1.1); 2.510(20.1); 2.506(38.9); 2.501(50.1); 2.497(36.1); 2.493(17.5); 1.989(10.6); 1.398(16.0); 1.192(2.9); 1.175(5.7); 1.157(2.8); 0.008(2.0); 0.000(43.4); −0.008(1.6) |
| I-1-36 | 1.83 | 1H NMR (400.0 MHz, d6-DMSO): δ = 13.376(5.1); 11.267(6.0); 8.977(0.3); 8.863(6.1); 8.317(0.4); 7.794(3.4); 7.792(5.7); 7.789(3.5); 7.774(4.7); 7.771(4.8); 7.738(2.6); 7.717(7.1); 7.702(7.6); 7.697(6.7); 7.682(5.9); 7.651(10.7); 7.631(6.4); 7.606(7.2); 7.584(13.1); 7.563(8.6); 7.547(16.0); 7.544(16.0); 7.539(13.0); 7.533(13.2); 7.530(13.9); 7.513(6.7); 7.509(6.8); 7.493 (7.3); 7.474(4.2); 7.462(2.8); 7.450(8.4); 7.442(7.7); 7.436(6.8); 7.430(10.2); 7.429(9.8); 7.424(8.0); 7.416(5.3); 7.409(5.2); 5.756(6.9); 3.507(0.5); 3.327(26.7); 2.676(0.9); 2.671(1.2); 2.667(0.9); 2.662(0.5); 2.566(0.3); 2.524(4.2); 2.511(67.7); 2.507(135.3); 2.502(177.8); 2.498 (128.9); 2.493(62.8); 2.338(0.4); 2.333(0.8); 2.329(1.2); 2.324(0.8); 1.235(1.1); 0.146(0.4); 0.008(3.0); 0.000(80.9); −0.008(3.0); −0.149(0.4) |
| I-1-37 | 2.19 | 1H NMR (400.0 MHz, d6-DMSO): δ 11.228(5.1); 8.746(5.4); 8.318(0.7); 7.839(4.4); 7.821(5.6); 7.774(4.2); 7.758(4.1); 7.699(8.3); 7.535(3.7); 7.367(3.8); 7.346(4.0); 7.242(4.6); 3.332(154.5); 2.675(0.8); 2.671(1.1); 2.667(0.9); 2.525(2.8); 2.511(70.7); 2.507(140.8); 2.502 (181.8); 2.498(129.3); 2.333(1.1); 2.329(1.3); 2.325(1.1); 2.245(16.0); 1.743(0.6); 0.146(0.6); 0.008(5.1); 0.000(140.0); −0.009(5.1); −0.149(0.6) |
| I-1-38 | 1.99 | 1H NMR (400.0 MHz, d6-DMSO): δ = 11.134(3.9); 8.727(2.8); 8.316(0.6); 8.181(2.6); 7.722(1.4); 7.708(1.5); 7.699(1.5); 7.685(1.5); 7.524(6.9); 7.488(5.3); 7.443(3.5); 7.426(3.8); 7.357(3.1); 7.336(3.1); 7.252(2.3); 7.236(3.6); 7.218(2.1); 7.073(1.0); 7.066(1.2); 7.049(1.0); 7.042(1.2); 6.991(0.7); 6.983(0.6); 6.969(1.2); 6.962(1.1); 6.948(0.6); 6.940(0.5); 3.326(239.7); 2.675(1.1); 2.671(1.4); 2.666(1.1); 2.524(4.4); 2.510(82.7); 2.506(163.1); 2.502(213.8); 2.497 (157.6); 2.493(78.6); 2.333(1.3); 2.328(1.7); 2.324(1.4); 2.257(16.0); 2.232(5.3); 2.180(1.6); 2.097(0.5); 1.055(0.6); 0.146(0.7); 0.008(6.3); 0.000(152.7); −0.008(6.5); −0.150(0.7) |
| I-1-39 | 2.13 | 1H NMR (400.0 MHz, d6-DMSO): δ = 11.063(11.3); 8.727(7.9); 8.317(0.8); 7.920(7.6); 7.902(8.2); 7.674(0.5); 7.464(16.0); 7.358(7.7); 7.337(7.8); 7.254(12.1); 7.233(12.1); 7.212(11.9); 4.038(0.4); 4.020(0.4); 3.328(312.6); 2.671(2.0); 2.667(1.6); 2.506(230.4); 2.502(302.4); 2.497(233.0); 2.328(2.8); 2.324(2.5); 2.237(14.3); 1.989(2.1); 1.235(0.5); 1.192(0.5); 1.175 (0.9); 1.157(0.5); 0.146(0.7); 0.008(6.3); 0.000(144.4); −0.150(0.7) |
| I-1-40 | 2.26 | 1H NMR (400.0 MHz, d6-DMSO): δ = 11.266(4.8); 11.016(0.3); 8.753(5.2); 8.575(0.3); 8.565(0.3); 8.318(0.8); 7.822(4.9); 7.771(4.5); 7.757(4.8); 7.719(8.1); 7.573(6.3); 7.546(4.6); 7.527(6.0); 7.471(5.7); 4.037(0.8); 4.020(0.9); 3.369(0.4); 3.330(254.3); 2.671(1.8); 2.506(243.6); 2.502(297.4); 2.497(208.1); 2.329(1.9); 2.110(16.0); 1.989(4.0); 1.950(0.4); 1.914(0.4); 1.899(0.4); 1.820(0.4); 1.761(0.6); 1.752(0.7); 1.733(0.7); 1.697(0.8); 1.684(0.8); 1.192(0.9); 1.175(2.0); 1.157(0.9); 0.146(0.8); 0.008(8.4); 0.000(184.5); −0.009(6.9); −0.150(0.8) |
| I-1-41 | 2.04 | 1H NMR (600.1 MHz, d6-DMSO): δ = 11.572 (0.4); 11.182 (4.5); 9.324 (1.6); 8.721 (5.3); 8.240 (1.3); 8.228 (1.4); 7.807 (1.0); 7.795 (2.4); 7.785 (1.3); 7.782 (1.2); 7.772 (1.5); 7.771 (1.5); 7.759 (0.7); 7.757 (0.7); 7.693 (0.3); 7.671 (1.4); 7.669 (1.4); 7.658 (2.2); 7.646 (1.5); 7.644 (1.5); 7.595 (6.3); 7.569 (11.9); 7.557 (15.0); 7.522 (15.5); 7.513 (16.0); 7.471 (9.1); 7.445 (13.5); 3.391 (0.5); 3.341 (303.0); 2.611 (0.3); 2.499 (53.6); 2.383 (0.4); 2.107 (12.5); 2.048 (2.9); 2.043 (3.2); 2.039 (3.5); 2.035 (2.9); 2.031 (2.2); 1.889 (0.6); 1.854 (0.5); 1.838 (0.5); 0.000 (2.0) |
| I-1-42 | 2.55 | 1H NMR (400.0 MHz, d6-DMSO): δ = 13.566(0.4); 11.254(6.4); 11.001(0.4); 8.788(6.7); 8.609(0.4); 8.317(0.9); 8.258(1.4); 7.848(5.5); 7.833(10.0); 7.829(10.1); 7.819(9.5); 7.805(8.5); 7.802(8.8); 7.785(6.4); 7.782(7.0); 7.767(10.8); 7.764(10.1); 7.749(10.7); 7.745(10.8); 7.724 (13.0); 7.722(12.9); 7.708(11.6); 7.640(2.3); 7.581(16.0); 7.502(7.0); 7.498(7.6); 7.492(7.5); 7.485(8.1); 7.425(1.8); 7.419(1.6); 7.408(1.5); 7.402(1.4); 7.318(0.7); 4.056(0.7); 4.038(2.2); 4.020(2.3); 4.002(0.8); 3.365(68.8); 2.998(2.0); 2.714(1.9); 2.680(0.7); 2.675(1.5); 2.671 (2.0); 2.666(1.5); 2.662(0.6); 2.524(4.8); 2.511(119.6); 2.506(243.7); 2.502(321.5); 2.497(231.8); 2.493(110.5); 2.378(9.3); 2.338(3.2); 2.333(3.5); 2.329(3.8); 2.324(3.0); 2.203(0.5); 2.179 (0.5); 2.161 (0.4); 2.149 (0.4); 1.989 (10.6); 1.965(0.8); 1.909(1.0); 1.259(0.4); 1.236(2.2); 1.192 (2.9); 1.175(5.8); 1.157(3.2); 1.081(15.6); 1.074(15.2); 1.055(11.0); 1.036(4.7); 0.922(1.1); 0.854(1.6); 0.836(1.4); 0.146(0.8); 0.008(6.5); 0.000(199.8); −0.009(6.8); −0.150(0.8) |
| I-1-43 | 2.36 | 1H NMR (400.0 MHz, d6-DMSO): δ = 11.173(2.8); 8.769(3.3); 8.316(0.7); 7.781(0.4); 7.765(0.4); 7.578(16.0); 7.544(6.2); 7.522(6.3); 7.484(9.7); 7.437(4.8); 7.423(5.0); 7.310 (0.5); 4.056(0.3); 4.038(1.1); 4.020(1.1); 4.002(0.4); 3.326(245.0); 2.675(1.1); 2.671(1.5); 2.666 (1.1); 2.524(3.8); 2.510(86.6); 2.506(168.6); 2.502(217.9); 2.497(158.5); 2.376(3.8); 2.338 (2.9); 2.333(3.2); 2.328(3.3); 2.324(2.8); 2.189(0.4); 1.989(4.7); 1.235(0.5); 1.193(1.4); 1.175 (2.7); 1.157(1.6); 1.069(8.7); 0.146(0.4); 0.008(3.7); 0.000(100.0); −0.008(3.5); −0.150(0.5) |
| I-1-44 | 2.26 | 1H NMR (400.0 MHz, d6-DMSO): δ = 13.576(7.0); 11.340(3.5); 8.950(0.4); 8.848(3.5); 8.316(1.1); 7.974(0.6); 7.956(0.6); 7.953(0.6); 7.924(0.4); 7.847(5.8); 7.831(9.5); 7.827(9.4); 7.817(8.0); 7.798(12.0); 7.784(10.9); 7.780(11.7); 7.766(16.0); 7.747(10.6); 7.743(10.9); 7.724 (10.2); 7.722(10.3); 7.701(8.5); 7.696(8.6); 7.675(6.9); 7.658(3.9); 7.582(0.7); 7.548(0.8); 7.528(0.9); 7.509(0.7); 5.756(1.9); 4.327(0.8); 4.309(0.9); 3.322(61.8); 2.998(0.8); 2.714(0.8); 2.675(2.0); 2.671(2.8); 2.666(2.0); 2.662(1.0); 2.524(11.2); 2.511(162.6); 2.506(318.8); 2.502 (415.7); 2.497(301.4); 2.493(148.6); 2.337(1.0); 2.333(2.0); 2.328(2.7); 2.324(2.0); 1.342 (0.9); 1.324(1.8); 1.307(0.9); 0.008(0.5); 0.000(13.2); −0.009(0.5) |
| I-1-45 | 2.09 | 1H NMR (400.0 MHz, d6-DMSO): δ = 11.240(0.6); 8.832(0.7); 7.787(1.8); 7.767(2.6); 7.710(0.7); 7.691(2.2); 7.673(1.9); 7.652(0.8); 7.581(0.3); 7.547(0.6); 7.463(1.0); 7.445(0.8); 7.416(0.8); 7.401(0.8); 4.056(1.1); 4.038(3.5); 4.020(3.6); 4.002(1.2); 3.320(49.5); 2.675(0.5); 2.670(0.7); 2.666(0.5); 2.541(0.4); 2.524(1.9); 2.510(41.4); 2.506(83.4); 2.501(109.2); 2.497 (77.1); 2.492(36.0); 2.333(0.5); 2.328(0.7); 2.323(0.5); 1.988(16.0); 1.193(4.3); 1.175(8.7); 1.157(4.3); 0.146(0.5); 0.008(4.9); 0.000(133.8); −0.009(4.5); −0.150(0.6) |

| Compound No. | log P neutral | ¹H NMR data |
|---|---|---|
| I-1-46 | 2.03 | 1H NMR (400.0 MHz, d6-DMSO): δ = 13.374(4.8); 11.260(3.2); 8.831(4.0); 8.316(0.5); 7.976(1.0); 7.974(1.1); 7.956(1.3); 7.953(1.1); 7.861(0.3); 7.791(11.9); 7.788(12.7); 7.773(11.4); 7.769(16.0); 7.766(15.9); 7.691(7.1); 7.672(7.4); 7.657(2.4); 7.651(3.9); 7.639(1.3); 7.636 (1.1); 7.573(3.5); 7.557(4.2); 7.547(14.8); 7.544(15.3); 7.538(11.5); 7.537(11.5); 7.533(11.1); 7.529(11.6); 7.513(6.2); 7.509(6.4); 7.487(5.2); 7.462(3.4); 7.449(6.3); 7.442(7.0); 7.436 (6.5); 7.430(7.5); 7.428(7.2); 7.423(7.5); 7.416(6.0); 7.409(4.9); 7.236(0.5); 7.216(0.5); 5.756 (1.1); 4.345(0.6); 4.327(1.9); 4.309(1.9); 4.292(0.6); 3.326(19.0); 2.675(0.9); 2.671(1.3); 2.666 (1.0); 2.662(0.5); 2.549(0.6); 2.524(4.9); 2.511(76.2); 2.506(150.6); 2.502(197.0); 2.497(143.2); 2.493(70.2); 2.338(0.5); 2.333(0.9); 2.328(1.3); 2.324(1.0); 1.342(2.0); 1.324(4.1); 1.307 (2.0); 1.234(0.4); 0.000(6.7) |
| I-1-47 | 2.04 | 1H NMR (400.0 MHz, d6-DMSO): δ = 11.102(2.8); 8.651(3.1); 8.317(0.9); 7.523(4.6); 7.484(4.5); 7.425(4.4); 7.389(4.3); 7.370(6.0); 7.353(4.9); 7.273(8.8); 3.329(232.9); 2.675(1.4); 2.671(1.9); 2.666(1.4); 2.524(5.5); 2.510(112.1); 2.506(229.5); 2.502(303.7); 2.497(219.1); 2.493(105.8); 2.333(1.5); 2.328(1.9); 2.324(1.5); 2.062(6.2); 2.029(16.0); 0.146(0.6); 0.008 (5.0); 0.000(139.8); −0.009(5.2); −0.150(0.6) |
| I-1-48 | 2.26 | 1H NMR (400.0 MHz, d6-DMSO): δ = 11.179(2.2); 8.667(2.6); 8.318(0.7); 7.821(2.2); 7.769(2.1); 7.756(2.1); 7.713(3.8); 7.377(2.2); 7.362(2.0); 7.285(4.3); 7.190(0.5); 4.037(0.4); 4.020(0.4); 3.330(113.2); 3.306(0.5); 2.675 (0.6); 2.671(0.8); 2.666(0.6); 2.510(51.2); 2.506(99.6); 2.502(127.4); 2.497(89.9); 2.493(41.9); 2.333(0.6); 2.328(0.8); 2.324(0.6); 2.038(16.0); 1.989(3.0); 1.876(0.4); 1.689(1.2); 1.192(0.5); 1.174(1.0); 1.157(0.5); 0.146(0.4); 0.008(4.0); 0.000(92.8); −0.009(3.1); −0.150(0.4) |
| I-1-49 | 2.15 | 1H NMR (400.0 MHz, d6-DMSO): δ = 11.142(3.7); 8.556(4.1); 8.318(0.6); 7.835(2.6); 7.820(3.4); 7.772(2.9); 7.756(2.9); 7.703(5.7); 7.438(3.3); 7.420(3.1); 7.107(3.1); 7.089(3.1); 7.019(3.1); 7.002(3.1); 4.037(0.4); 4.020(0.5); 3.762(16.0); 3.329(170.5); 2.675(0.9); 2.671 (1.2); 2.666(0.9); 2.510(75.0); 2.506(145.4); 2.502(186.5); 2.497(133.6); 2.493(65.3); 2.333(0.9); 2.328(1.2); 2.324(0.9); 2.058(12.7); 1.989(2.3); 1.551(0.6); 1.398(0.5); 1.192(0.5); 1.175 (1.0); 1.157(0.5); 0.146(0.4); 0.008(3.4); 0.000(78.6); −0.008(3.5); −0.150(0.3) |
| I-1-50 | 1.95 | 1H NMR (400.0 MHz, d6-DMSO): δ = 11.061(1.8); 8.539(1.9); 8.313(0.3); 7.524(2.9); 7.484(2.7); 7.449(3.6); 7.430(5.3); 7.412(3.6); 7.098(3.0); 7.079(2.7); 7.008(2.2); 6.993(2.2); 4.038(0.4); 4.020(0.4); 3.751(16.0); 3.430(0.4); 3.344(619.2); 3.312(1.8); 3.287(0.5); 3.272 (0.4); 2.676(0.6); 2.671(0.7); 2.667(0.6); 2.524(2.0); 2.507(84.5); 2.502(108.2); 2.498(78.1); 2.333 (0.5); 2.329(0.7); 2.325(0.5); 2.052(4.6); 1.988(2.2); 1.192(0.4); 1.175(0.8); 1.157(0.5) |
| I-1-51 | 2.49 | 1H NMR (400.0 MHz, d6-DMSO): δ = 11.342(7.2); 8.908(6.4); 8.316(1.0); 7.889(8.6); 7.869(10.1); 7.841(8.7); 7.822(10.9); 7.771(6.7); 7.755(7.2); 7.704(16.0); 7.614(6.4); 7.594 (9.0); 7.575(4.7); 7.511(0.7); 7.497(0.6); 4.056(0.8); 4.038(2.6); 4.020(2.7); 4.002(0.9); 3.323 (239.4); 2.998(0.3); 2.714(0.3); 2.679(0.9); 2.675(1.9); 2.670(2.7); 2.666(1.9); 2.661(0.9); 2.541 (1.4); 2.524(6.2); 2.519(9.5); 2.510(148.1); 2.506(307.9); 2.501(408.9); 2.497(288.1); 2.492 (133.2); 2.337(0.9); 2.333(1.9); 2.328(2.6); 2.324(1.9); 2.319(0.9); 1.989(11.9); 1.235(0.7); 1.193(3.2); 1.175(6.4); 1.157(3.1); 0.146(0.5); 0.008(3.5); 0.000(117.6); −0.009(3.5); −0.150 (0.5) |
| I-1-52 | 2.29 | 1H NMR (400.0 MHz, d6-DMSO): δ = 11.258(10.6); 8.891(8.0); 8.316(0.6); 7.890(11.6); 7.888(11.6); 7.869(13.0); 7.867(13.5); 7.694(4.7); 7.613(10.3); 7.593(16.0); 7.573(11.7); 7.551 (11.5); 7.531(14.6); 7.513(7.8); 7.495(10.6); 7.476(5.6); 7.449(8.1); 7.431(9.8); 7.414(4.0); 4.056(0.4); 4.038(1.3); 4.020(1.3); 4.002(0.4); 3.873(0.6); 3.324(215.5); 2.675(1.2); 2.671(1.7); 2.666(1.2); 2.541(0.8); 2.524(4.1); 2.511(97.1); 2.506(198.0); 2.502(261.1); 2.497(186.3); 2.493(88.2); 2.333(1.2); 2.328(1.7); 2.324(1.2); 2.288(1.1); 1.989(5.6); 1.193(1.5); 1.175(2.9); 1.157(1.4); 0.008(2.3); 0.000(67.2); −0.008(2.1) |
| I-1-53 | 2.58 | 1H NMR (400.0 MHz, d6-DMSO): δ = 13.580(0.7); 11.331(7.3); 8.878(6.3); 8.316(1.1); 7.977(9.1); 7.841(8.3); 7.822(10.8); 7.757(11.1); 7.700(13.4); 7.680(16.0); 7.660(8.8); 7.511 (0.6); 7.495(0.5); 7.462(0.4); 4.056(0.5); 4.038(1.5); 4.020(1.6); 4.002(0.5); 3.364(0.3); 3.323 (245.7); 3.287(0.4); 2.998(0.7); 2.714(0.7); 2.675(2.0); 2.671(2.8); 2.666(1.9); 2.661(1.0); 2.559 (0.5); 2.541(1.5); 2.524(7.1); 2.519(12.0); 2.511(164.3); 2.506(329.3); 2.502(427.2); 2.497 (300.1); 2.493(138.1); 2.333(2.0); 2.328(2.6); 2.324(1.9); 2.319(0.9); 1.989(6.9); 1.398(0.6); 1.234(0.4); 1.193(1.9); 1.175(3.9); 1.157(1.8); 0.146(1.1); 0.008(10.5); 0.000(292.3); −0.009 (8.5); −0.020(0.5); −0.150(1.1) |
| I-1-54 | 2.55 | 1H NMR (400.0 MHz, d6-DMSO): δ = 11.359(6.1); 8.973(1.5); 8.908(5.6); 8.316(0.6); .898(4.9); 7.863(2.3); 7.843(7.4); 7.824(9.9); 7.804(6.9); 7.783(10.2); 7.763(6.6); 7.761(6.7); 7.756(6.7); 7.695(16.0); 7.524(0.4); 4.038(0.5); 4.020(0.5); 3.325(233.6); 2.675(1.1); 2.671 (1.5); 2.666(1.1); 2.662(0.5); 2.541(0.9); 2.524(4.0); 2.511(86.1); 2.506(172.0); 2.502(223.3); 2.497(156.6); 2.493(72.3); 2.333(1.0); 2.329(1.4); 2.324(1.0); 1.989(2.2); 1.398(0.7); 1.236 (0.4); 1.193(0.6); 1.175(1.2); 1.157(0.6); 0.008(2.1); 0.000(58.4); −0.009(1.7) |
| I-1-55 | 2.34 | 1H NMR (400.0 MHz, d6-DMSO): δ = 11.272(12.5); 8.893(10.4); 8.315(1.1); 7.880(4.1); 7.802(10.1); 7.781(13.9); 7.695(11.9); 7.690(11.1); 7.673(8.4); 7.669(7.6); 7.551 (13.2); 7.533(16.0); 7.516(8.5); 7.497(11.4); 7.478(6.1); 7.451(8.9); 7.433(10.6); 7.416(4.3); 4.055(0.4); 4.038(1.3); 4.020(1.4); 4.002(0.5); 3.321(274.4); 2.675(3.0); 2.670(3.8); 2.666(2.8); 2.541(2.6); 2.506(476.8); 2.501(585.1); 2.497(415.8); 2.332(3.0); 2.328(3.8); 2.324(2.7); 1.989(5.7); 1.398(3.1); 1.193(1.5); 1.175(3.1); 1.157(1.6); 0.146(0.6); 0.000(125.7); −0.008 (4.7); −0.150(0.6) |
| I-1-57 | 2.10 | 1H NMR (400.0 MHz, d6-DMSO): δ = 11.413(1.6); 8.936(1.2); 7.845(2.2); 7.826(2.8); 7.799(1.0); 7.776(1.3); 7.760(1.3); 7.723(2.2); 7.706(2.3); 7.529(1.2); 5.760(0.4); 4.056(2.9); 4.038(3.8); 4.020(3.8); 4.002(1.3); 3.329(109.4); 2.672(0.5); 2.507(57.5); 2.502(72.0); 2.498 (54.3); 2.329(0.5); 1.989(16.0); 1.193(4.2); 1.175(8.3); 1.157(4.1); 0.146(0.4); 0.008(5.8); 0.000 (82.6); −0.150(0.4) |
| I-1-58 | 1.91 | 1H NMR (400.0 MHz, d6-DMSO): δ = 11.333(11.8); 8.923(8.0); 8.455(1.2); 8.317(0.3); 7.871(1.6); 7.859(1.9); 7.847(4.2); 7.835(4.6); 7.824(4.7); 7.812(4.5); 7.800(2.2); 7.788(1.8); 7.711(0.4); 7.698(0.4); 7.687(0.5); 7.676(0.4); 7.652(0.3); 7.587(5.2); 7.569(7.0); 7.555(9.4); |

| Compound No. | log P neutral | $^1$H NMR data |
|---|---|---|
| | | 7.535(16.0); 7.521(11.2); 7.502(11.4); 7.482(4.8); 7.454(7.0); 7.436(8.9); 7.418(3.7); 5.761 (1.7); 4.056(0.6); 4.038(1.8); 4.020(1.8); 4.002(0.6); 3.331(236.9); 2.671(1.0); 2.506 (117.9); 2.502(150.7); 2.499(119.7); 2.329(1.0); 1.989(7.6); 1.236(0.9); 1.193(2.0); 1.175(3.9); 1.157 (2.0); 0.146(0.9); 0.000(179.1); −0.150(1.0) |
| I-1-59 | 2.03 | 1H NMR (400.0 MHz, d6-DMSO): δ = 11.260(14.8); 8.922(8.9); 8.454(1.8); 8.317(0.5); 7.929(9.3); 7.909(9.8); 7.873(1.8); 7.860(2.1); 7.848(4.4); 7.836(4.7); 7.825(4.7); 7.813(4.6); 7.801(2.2); 7.789(1.9); 7.711(0.5); 7.699(0.6); 7.688(0.6); 7.676(0.6); 7.664(0.4); 7.652(0.4); 7.561(2.4); 7.556(3.1); 7.551(3.1); 7.546(3.1); 7.538(4.7); 7.532(5.6); 7.528(5.5); 7.522(5.1); 7.514(3.5); 7.489(14.5); 7.478(16.0); 7.441(1.1); 7.435(1.1); 7.431(1.0); 7.425(0.9); 7.418(0.5); 7.412(0.5); 7.407(0.4); 7.401(0.4); 7.242(4.0); 7.232(6.3); 7.221(6.1); 7.212(6.5); 7.200(3.5); 5.761(2.6); 4.038(1.0); 4.020(1.0); 3.329(151.5); 2.676(0.8); 2.671(1.2); 2.667(0.9); 2.524 (2.5); 2.511(61.9); 2.506(127.4); 2.502(171.3); 2.497(129.3); 2.493(66.2); 2.333(0.9); 2.329 (1.2); 2.324(0.9); 1.989(4.3); 1.397(0.4); 1.235(2.3); 1.193(1.2); 1.175(2.3); 1.157(1.1); 0.000 (9.8); −0.008(0.4) |
| I-1-60 | 2.21 | 1H NMR (400.0 MHz, d6-DMSO): δ = 11.061(3.8); 8.920(4.9); 7.872(0.5); 7.859(0.6); 7.847(1.1); 7.835(1.1); 7.825(1.1); 7.813(1.1); 7.800(0.6); 7.788(0.5); 7.562(0.6); 7.556(0.7); 7.552(0.7); 7.546(0.7); 7.538(1.1); 7.533(1.3); 7.528(1.2); 7.522(1.1); 7.515(0.6); 7.509(0.7); 7.504(0.6); 7.499(0.5); 7.463(1.9); 7.443(2.7); 7.422(2.6); 7.419(2.3); 7.404(2.0); 7.400(1.7); 7.339(3.3); 7.320(2.4); 7.303(1.9); 7.284(2.6); 7.266(1.2); 4.038(1.1); 4.020(0.7); 4.002(0.4); 3.326(25.9); 2.922(0.5); 2.904(0.5); 2.775(1.5); 2.756(4.5); 2.737(4.7); 2.718(1.6); 2.671(0.4); 2.511(23.0); 2.506 (44.5); 2.502(58.0); 2.497(42.6); 2.493(21.1); 2.329(0.4); 1.989 (5.0); 1.195(6.9); 1.176(16.0); 1.157(7.8); 1.134(0.7); 0.146(0.4); 0.008(4.2); 0.000(82.5); −0.009 (3.5); −0.150(0.4) |
| I-1-61 | 2.05 | 1H NMR (400.0 MHz, d6-DMSO): δ = 11.369(9.2); 8.878(7.7); 8.317(1.0); 7.842(8.1); 7.824(10.4); 7.772(6.9); 7.758(7.2); 7.717(12.4); 7.704(13.5); 7.649(9.7); 7.627(16.0); 7.605 (9.3); 7.536(0.5); 7.523(0.5); 7.512(0.4); 7.501(0.4); 4.038(0.5); 4.020(0.5); 3.328(271.4); 2.714 (0.3); 2.676(1.6); 2.671(2.1); 2.667(1.6); 2.507(235.1); 2.502(304.9); 2.498(228.5); 2.333 (1.5); 2.329(2.0); 2.324(1.5); 1.989(2.1); 1.235(0.3); 1.193(0.6); 1.175(1.2); 1.157(0.6); 0.146 (0.6); 0.008(6.2); 0.000(132.8); −0.008(7.0); −0.150(0.6) |
| I-1-62 | 1.85 | 1H NMR (400.0 MHz, d6-DMSO): δ = 11.288(10.2); 8.865(7.2); 8.317(0.5); 7.647(8.6); 7.625(16.0); 7.603(9.2); 7.579(5.1); 7.554(7.1); 7.532(10.2); 7.516(6.0); 7.498(8.0); 7.479(4.2); 7.451(6.2); 7.433(7.7); 7.415(3.2); 3.328(135.6); 2.675(0.9); 2.671(1.2); 2.667(0.9); 2.506 (139.1); 2.502(177.6); 2.498(133.8); 2.333(0.9); 2.329(1.2); 2.325(0.9); 1.989(1.1); 1.175(0.6); 0.146(0.4); 0.000(74.7); −0.150(0.4) |
| I-1-63 | 2.00 | 1H NMR (400.0 MHz, d6-DMSO): δ = 11.212(3.1); 8.862(2.0); 7.926(2.0); 7.906(2.1); 7.648(2.2); 7.626(4.1); 7.605(2.2); 7.484(2.9); 7.473(3.6); 7.238(0.9); 7.229(1.2); 7.218(1.4); 7.210(1.3); 7.196(0.8); 4.055(1.2); 4.038(3.8); 4.020(3.8); 4.002(1.3); 3.327(43.8); 2.671(0.4); 2.506(45.7); 2.502(61.4); 2.497(47.2); 2.329(0.4); 1.989(16.0); 1.235(0.9); 1.193(4.2); 1.175 (8.4); 1.157(4.2); 0.000(3.0) |
| I-1-64 | 2.14 | 1H NMR (400.0 MHz, d6-DMSO): δ = 11.017(3.5); 8.861(5.0); 7.648(2.4); 7.626(4.1); 7.604(2.4); 7.457(1.7); 7.438(2.8); 7.419(2.3); 7.400(1.7); 7.336(2.9); 7.318(2.0); 7.300(1.6); 7.281(2.2); 7.262(1.0); 4.056(0.8); 4.038(2.3); 4.020(2.4); 4.002(0.8); 3.331(26.7); 2.924(0.5); 2.905(0.5); 2.772(1.3); 2.753(3.8); 2.734(3.9); 2.716(1.3); 2.506(19.2); 2.502(25.1); 2.498 (19.0); 1.989(10.0); 1.193(7.8); 1.175(16.0); 1.156(7.1); 1.135(0.6); 0.008(0.5); 0.000(11.2); −0.008 (0.5) |
| I-1-65 | 2.49 | 1H NMR (400.0 MHz, d6-DMSO): δ = 11.474(3.2); 8.989(0.5); 8.953(2.5); 8.908(0.6); 8.484(11.6); 8.317(1.1); 7.953(0.4); 7.936(0.5); 7.932(0.4); 7.846(3.4); 7.827(4.5); 7.775(2.7); 7.758(2.9); 7.725(4.6); 7.707(5.1); 7.638(0.5); 7.621(0.5); 7.601(0.3); 7.498(0.4); 6.185(0.4); 5.864(16.0); 4.055(0.4); 4.038(1.3); 4.020(1.4); 4.002(0.4); 3.368(1.3); 3.326(380.2); 2.998 (0.7); 2.714(0.8); 2.675(2.0); 2.671(2.7); 2.666(2.1); 2.662(1.1); 2.524(6.9); 2.511(141.7); 2.506 (291.2); 2.502(390.9); 2.497(289.0); 2.493(143.2); 2.338(0.8); 2.333(1.8); 2.329(2.6); 2.324 (1.9); 2.121(0.7); 1.989(5.9); 1.398(0.9); 1.362(0.4); 1.236(1.7); 1.224(0.4); 1.206(0.5); 1.193 (1.6); 1.175(3.2); 1.157(1.6); 1.045(0.5); 1.029(0.5); 0.146(2.7); 0.008(22.3); 0.000(597.1); −0.009 (24.1); −0.036(0.4); −0.150(2.6) |
| I-1-66 | 2.28 | 1H NMR (400.0 MHz, d6-DMSO): δ = 11.399(15.8); 9.893(0.5); 8.943(11.8); 8.894(0.3); 8.715(0.4); 8.484(10.4); 8.317(1.3); 8.202(0.5); 8.184(0.5); 7.968(0.4); 7.955(0.8); 7.937(0.8); 7.934(0.7); 7.781(0.4); 7.750(0.8); 7.749(0.8); 7.730(0.9); 7.705(0.7); 7.686(0.8); 7.672(0.7); 7.660(0.5); 7.642(0.9); 7.623(1.2); 7.587(6.7); 7.570(8.9); 7.557(8.7); 7.537(16.0); 7.520(10.0); 7.505(13.7); 7.485(6.8); 7.455(9.0); 7.437(11.6); 7.419(5.4); 5.863(14.5); 4.056(0.9); 4.038 (2.7); 4.020(2.7); 4.002(0.9); 3.326(291.6); 2.675(2.2); 2.671(2.9); 2.667(2.2); 2.524(7.2); 2.506(333.8); 2.502(442.3); 2.497(331.1); 2.333(2.2); 2.329(2.9); 2.324(2.2); 2.180(0.6); 1.989 (11.6); 1.398(1.3); 1.235(8.4); 1.193(3.2); 1.175(6.3); 1.157(3.1); 1.045(0.7); 1.029(0.7); 0.854 (0.8); 0.836(0.4); 0.146(2.8); 0.008(23.2); 0.000(611.3); −0.008(28.8); −0.150(2.8) |
| I-1-67 | 2.43 | 1H NMR (400.0 MHz, d6-DMSO): δ = 13.304(0.4); 11.323(12.6); 8.942(8.9); 8.483(3.1); 8.316(0.6); 7.986(2.5); 7.967(2.7); 7.930(8.0); 7.910(8.5); 7.708(1.9); 7.689(2.2); 7.663(0.3); 7.643(0.3); 7.490(14.3); 7.478(16.0); 7.457(2.7); 7.245(4.6); 7.234(6.4); 7.225(7.4); 7.214(6.2); 7.203(3.6); 5.863(4.7); 4.055(0.6); 4.038(1.9); 4.020(1.9); 4.002(0.7); 3.327(206.0); 2.671 (1.9); 2.506(228.9); 2.502(282.2); 2.498(224.3); 2.329(1.9); 1.989(7.8); 1.398(0.4); 1.236(1.6); 1.193(2.1); 1.175(2.1); 1.157(2.1); 0.146(1.5); 0.000(309.9); −0.150(1.6) |
| I-1-68 | 2.61 | 1H NMR (400.0 MHz, d6-DMSO): δ = 12.817(0.5); 11.130(4.6); 8.940(1.9); 7.767(1.0); 7.747(1.0); 7.479(0.6); 7.463(3.2); 7.444(4.3); 7.425(2.9); 7.406(2.2); 7.341(3.7); 7.322(3.7); 7.304(2.9); 7.294(1.2); 7.285(3.0); 7.275(1.5); 7.267(1.4); 7.257(0.7); 3.327(39.4); 2.942(0.6); 2.923(1.9); 2.905(2.0); 2.886(0.7); 2.771(1.6); 2.752(4.9); 2.733(5.0); 2.715(1.7); 2.671(0.4); 2.506(44.9); 2.502(57.2); 2.498(44.3); 2.328(0.4); 1.989(1.2); 1.235(0.4); 1.191(6.7); 1.172 (16.0); 1.154(11.1); 1.135(2.4); 0.146(0.3); 0.000(65.3) |

| Compound No. | log P neutral | ¹H NMR data |
|---|---|---|
| I-1-70 | 2.15 | 1H NMR (400.0 MHz, d6-DMSO): δ = 11.288(8.0); 8.842(7.4); 8.316(1.4); 7.905(7.5); .887(8.5); 7.839(8.1); 7.820(10.3); 7.770(6.9); 7.755(7.0); 7.697(16.0); 7.604(9.7); 7.586(6.2); 7.538(7.2); 7.520(10.0); 7.503(5.3); 4.056(0.5); 4.038(1.5); 4.020(1.5); 4.002(0.5); 3.323(318.2); 2.675(2.0); 2.670(2.8); 2.666(2.1); 2.524(6.1); 2.510(149.6); 2.506(311.6); 2.501(423.9); 2.497(325.1); 2.493(171.9); 2.333(1.9); 2.328(2.7); 2.324(2.1); 1.988(6.6); 1.236 (0.8); 1.193(1.7); 1.175(3.5); 1.157(1.7); 0.146(2.7); 0.008(20.9); 0.000(574.9); −0.008 (31.9); −0.150(2.6) |
| I-1-71 | 1.96 | 1H NMR (400.0 MHz, d6-DMSO): δ = 11.206(8.2); 8.826(6.4); 8.315(0.7); 7.904(8.4); 7.884(8.9); 7.656(4.4); 7.621(6.9); 7.603(10.4); 7.583(7.7); 7.540(14.0); 7.536(13.6); 7.522 (16.0); 7.503(9.6); 7.498(9.6); 7.473(4.8); 7.448(6.7); 7.430(7.6); 4.038(0.4); 4.020 (0.4); 3.323(141.6); 2.675(1.3); 2.670(1.5); 2.666(1.1); 2.510(123.3); 2.506(200.1); 2.501(229.8); 2.497(159.4); 2.493(74.2); 2.333(1.3); 2.328(1.5); 2.324(1.0); 1.988(1.6); 1.236(1.5); 1.193 (0.4); 1.175(0.9); 1.157(0.4); 0.146(1.2); 0.008(26.2); 0.000(281.2); −0.008(12.4); −0.150 (1.3) |
| I-1-72 | 2.09 | 1H NMR (400.0 MHz, d6-DMSO): δ = 13.305(0.6); 11.133(9.3); 8.826(6.6); 8.316(0.5); 8.088(0.6); 8.068(0.6); 7.988(0.9); 7.968(1.0); 7.925(7.5); 7.905(16.0); 7.885(9.9); 7.709(1.3); 7.689(2.5); 7.660(3.8); 7.622(5.6); 7.604(9.5); 7.585(5.3); 7.540(6.4); 7.518(9.2); 7.498(6.5); 7.469(12.9); 7.361(0.4); 7.340(0.5); 7.319(0.4); 7.247(1.1); 7.227(4.8); 7.212(6.0); 7.192(3.1); 4.037(0.4); 4.019(0.4); 3.324(66.6); 2.675(0.7); 2.670(1.0); 2.666(0.8); 2.523(2.3); 2.510 (56.0); 2.505(116.5); 2.501(158.3); 2.497(120.8); 2.492(63.8); 2.332(0.7); 2.328(1.0); 2.323(0.8); 1.988(1.8); 1.235(0.3); 1.192(0.5); 1.174(0.9); 1.157(0.5); 0.146(0.8); 0.008(5.5); 0.000(159.3); −0.008(8.4); −0.150(0.8) |
| I-1-73 | 2.34 | 1H-NMR (400.0 MHz, d6-DMSO): δ = 10.937(3.6); 8.823(6.7); 7.904(3.1); 7.887(3.2); 7.884(3.4); 7.665(1.3); 7.645(2.6); 7.624(1.9); 7.621(2.1); 7.606(3.0); 7.603(3.2); 7.586(1.4); 7.583(1.5); 7.539(2.0); 7.535(2.0); 7.520(2.7); 7.516(2.7); 7.501(1.3); 7.497(1.3); 7.447(1.8); 7.428(3.1); 7.412(2.9); 7.393(2.1); 7.332(3.8); 7.314(2.6); 7.294(1.9); 7.275(2.8); 7.257(1.2); 3.323(52.3); 2.903(0.3); 2.779(1.7); 2.760(5.2); 2.741(5.4); 2.722(1.8); 2.675(0.3); 2.670(0.5); 2.666(0.4); 2.523(1.1); 2.506(57.1); 2.501(77.5); 2.497(59.8); 2.332(0.4); 2.328(0.5); 2.324 (0.4); 1.200 (7.5); 1.181(16.0); 1.163(7.3); 1.153(1.2); 1.134(0.5); 0.008(2.3); 0.000(67.0); −0.008 (3.8); −0.150(0.3) |
| I-1-75 | 2.20 | 1H NMR (400.0 MHz, d6-DMSO): δ = 11.272(2.8); 8.793(2.5); 8.087(3.0); 8.068(3.2); 7.836(2.6); 7.818(3.4); 7.768(2.5); 7.753(2.4); 7.699(4.5); 7.589(5.7); 7.500(0.4); 7.359(1.9); 7.339(3.1); 7.320(1.7); 4.055(1.3); 4.038(3.8); 4.020(3.9); 4.002(1.4); 3.325(47.4); 2.670(0.4); 2.666(0.3); 2.524(0.4); 2.506(61.3); 2.501(84.6); 2.497(66.4); 2.328(0.7); 2.324(0.6); 1.988 (16.0); 1.235(1.5); 1.192(4.1); 1.175(8.3); 1.157(4.2); 0.008(1.9); 0.000(77.6); −0.150(0.4) |
| I-1-76 | 2.01 | 1H NMR (400.0 MHz, d6-DMSO): δ = 13.378(0.4); 11.188(9.2); 8.776(6.6); 8.315(1.4); 8.086(10.9); 8.066(12.3); 7.770(1.2); 7.751(1.4); 7.696(0.4); 7.595(11.4); 7.578(16.0); 7.548 (11.1); 7.527(15.3); 7.509(7.8); 7.489(9.2); 7.471(5.6); 7.446(7.6); 7.428(9.5); 7.412(5.3); 7.361 (6.6); 7.356(5.9); 7.339(10.6); 7.325(5.2); 7.319(6.4); 4.056(0.5); 4.038(1.2); 4.020(1.3); 4.002 (0.5); 3.324(443.3); 2.675(1.2); 2.671(2.2); 2.666(1.6); 2.510(152.6); 2.506(335.8); 2.501 (469.5); 2.497(372.5); 2.493(211.0); 2.333(3.4); 2.328(4.3); 2.324(3.6); 1.988(5.3); 1.398(0.4); 1.258(0.4); 1.235(1.2); 1.192(1.4); 1.175(2.6); 1.157(1.4); 0.146(1.7); 0.008(11.8); 0.000 (418.4); −0.150(2.2) |
| I-1-77 | 2.15 | 1H NMR (400.0 MHz, d6-DMSO): δ = 13.305(0.8); 11.116(12.2); 8.778(8.3); 8.316(1.2); 8.089(12.8); 8.069(13.9); 7.984(1.0); 7.964(1.1); 7.925(8.7); 7.905(9.3); 7.704(0.8); 7.684(1.0); 7.615(3.4); 7.598(12.3); 7.583(14.2); 7.470(16.0); 7.362(6.7); 7.356(5.0); 7.341(9.9); 7.319 (5.6); 7.271(0.4); 7.224(5.8); 7.211(6.8); 7.190(3.6); 4.055(0.4); 4.037(1.2); 4.020(1.2); 4.002 (0.4); 3.323(220.8); 2.675(1.9); 2.670(2.7); 2.666(2.0); 2.524(6.9); 2.510(153.5); 2.506(316.7); 2.501(425.4); 2.497(318.3); 2.493(163.2); 2.333(2.0); 2.328(2.8); 2.324(2.1); 1.989(5.2); 1.235(0.5); 1.193(1.4); 1.175(2.7); 1.157(1.4); 0.146(1.8); 0.008(13.4); 0.000(396.4); −0.008 (18.4); −0.150(1.8) |
| I-1-78 | 2.31 | 1H NMR (400.0 MHz, d6-DMSO): δ = 10.925(3.8); 8.774(6.6); 8.088(3.4); 8.069(3.6); 7.616(1.1); 7.599(3.1); 7.579(3.7); 7.569(3.2); 7.553(1.1); 7.449(2.0); 7.429(3.2); 7.410(2.9); 7.391(2.2); 7.360(1.9); 7.355(1.8); 7.334(4.8); 7.323(2.0); 7.314(2.8); 7.294(2.0); 7.275(2.9); 7.256(1.2); 4.037(0.4); 4.020(0.4); 3.324(26.3); 2.782(1.7); 2.763(5.3); 2.744(5.5); 2.725(1.9); 2.505(31.2); 2.501(42.2); 2.496(32.7); 2.328(0.3); 1.988(1.4); 1.203(7.6); 1.184(16.0); 1.175 (1.8); 1.165(7.4); 1.153(1.0); 1.134(0.4); 0.008(1.2); 0.000(38.9) |
| I-1-80 | 2.32 | 1H NMR (400.0 MHz, d6-DMSO): δ = 13.578(0.4); 11.331(2.0); 8.820(2.2); 8.223(0.3); 8.205(0.4); 7.935(4.3); 7.918(5.0); 7.869(0.9); 7.821(3.7); 7.791(2.9); 7.775(2.7); 7.759(3.5); 7.712(4.9); 7.601(0.7); 7.583(0.6); 7.514(1.9); 7.495(3.1); 7.475(2.2); 5.756(0.8); 4.056(1.3); 4.038(3.9); 4.020(4.0); 4.002(1.5); 3.325(30.5); 2.671(0.7); 2.502(100.7); 2.328(0.7); 1.989 (16.0); 1.236(1.0); 1.193(4.3); 1.175(8.6); 1.157(4.4); 0.000(62.1); −0.149(0.3) |
| I-1-81 | 2.45 | 1H NMR (400.0 MHz, d6-DMSO): δ = 10.976(2.6); 8.907(2.1); 8.843(0.5); 8.791(5.4); 8.316(0.5); 8.292(1.6); 8.167(1.6); 8.149(1.8); 7.984(0.3); 7.947(1.2); 7.936(9.0); 7.927(1.8); 7.916(9.7); 7.902(0.8); 7.866(1.9); 7.845(2.0); 7.794(0.9); 7.775(0.9); 7.756(0.7); 7.704(1.4); 7.685(1.8); 7.666(0.8); 7.534(0.4); 7.514(3.2); 7.493(5.1); 7.473(1.8); 7.448(2.0); 7.431(2.9); 7.404(3.1); 7.386(2.2); 7.327(4.0); 7.308(2.7); 7.285(2.1); 7.266(2.9); 7.248(1.2); 6.182(2.5); 5.562(1.7); 4.038(0.5); 4.020(0.5); 3.336(10.7); 3.323(163.4); 3.322(139.0); 2.774(2.0); 2.755 (5.4); 2.736(5.4); 2.717(1.8); 2.674(1.4); 2.670(1.6); 2.505(219.6); 2.501(242.1); 2.332(1.4); 2.328(1.6); 1.989(2.1); 1.398(0.7); 1.201(8.0); 1.193(2.5); 1.182(16.0); 1.163(7.3); 0.012(2.6); 0.002(23.0); 0.000(46.3); −0.008(2.2) |
| I-1-83 | 2.21 | 1H NMR (400.0 MHz, d6-DMSO): δ = 11.326(1.7); 8.907(0.8); 8.831(1.6); 8.283(0.4); 8.167(0.3); 8.150(0.4); 7.923(2.0); 7.903(2.2); 7.867(0.4); 7.833(1.9); 7.828(1.9); 7.819(2.4); 7.801(1.3); 7.781(1.3); 7.767(2.0); 7.756(1.8); 7.749(2.1); 7.719(2.8); 7.709(2.9); 7.704(2.9); 7.685(1.8); 7.667(0.8); 7.613(0.4); 7.592(1.1); 7.569(2.0); 7.548(1.7); 7.472(1.1); 7.453(1.9); 7.438(1.8); 7.419(0.8); 4.055(1.2); 4.038(3.6); 4.020(3.6); 4.002(1.2); 3.347(17.1); 2.675(0.4); |

| Compound No. | log P neutral | ¹H NMR data |
|---|---|---|
| | | 2.671(0.6); 2.666(0.5); 2.524(1.2); 2.510(32.9); 2.506(68.5); 2.502(92.1); 2.497(67.5); 2.493 (33.3); 2.333(0.4); 2.328(0.6); 2.324(0.4); 2.136(1.4); 1.989(16.0); 1.193(4.2); 1.175(8.3); 1.157 (4.1) |
| I-1-84 | 2.02 | 1H NMR (400.0 MHz, d6-DMSO): δ = 13.379(0.4); 11.560(1.8); 11.249(5.1); 9.339(1.4); 8.907(11.9); 8.865(0.4); 8.816(4.5); 8.316(0.5); 8.290(0.4); 8.223(1.7); 8.205(1.9); 8.201(1.5); 8.167(5.4); 8.154(1.4); 8.149(6.2); 8.146(4.9); 7.923(7.4); 7.903(8.1); 7.821(0.5); 7.802(1.3); 7.791(4.5); 7.784(1.4); 7.780(1.6); 7.774(6.1); 7.770(4.2); 7.759(1.7); 7.756(2.7); 7.753(1.6); 7.729(1.6); 7.710(2.8); 7.704(4.9); 7.684(6.8); 7.670(1.2); 7.666(2.8); 7.590(6.9); 7.568(10.4); 7.547(15.5); 7.544(16.0); 7.539(10.1); 7.533(9.9); 7.529(11.0); 7.513(4.6); 7.509(5.1); 7.491 (5.5); 7.473(7.0); 7.459(6.9); 7.450(9.3); 7.442(9.2); 7.439(9.7); 7.431(9.8); 7.424(7.3); 7.416 (5.4); 7.409(4.3); 6.183(0.6); 4.056(0.9); 4.038(2.8); 4.020(2.8); 4.002(1.0); 3.414(5.8); 2.676 (0.8); 2.671(1.2); 2.667(0.9); 2.662(0.4); 2.525(2.3); 2.511(65.7); 2.507(137.5); 2.502(185.3); 2.498(136.6); 2.493(68.1); 2.338(0.4); 2.333(0.9); 2.329(1.2); 2.324(0.9); 2.137(1.4); 1.989 (12.3); 1.397(0.4); 1.235(1.3); 1.193(3.3); 1.175(6.5); 1.157(3.2); 0.000(0.6) |
| I-1-85 | 2.15 | 1H NMR (400.0 MHz, d6-DMSO): δ = 13.301(1.0); 11.492(0.8); 11.165(7.9); 9.336(0.6); 8.906(1.8); 8.810(6.1); 8.775(0.7); 8.315(0.5); 8.227(0.7); 8.206(0.7); 8.167(1.3); 8.146(1.3); 7.988(2.1); 7.969(2.2); 7.948(0.9); 7.923(14.2); 7.903(15.3); 7.803(0.5); 7.780(0.5); 7.774(0.8); 7.756(0.6); 7.729(0.6); 7.710(2.5); 7.691(2.4); 7.684(2.1); 7.664(0.7); 7.590(3.9); 7.568(8.2); 7.546(5.5); 7.474(16.0); 7.459(9.3); 7.454(10.1); 7.439(6.8); 7.418(2.9); 7.343(0.4); 7.331 (0.4); 7.248(1.6); 7.229(4.6); 7.220(4.9); 7.211(5.6); 7.201(4.5); 6.180(2.0); 4.055(0.4); 4.037 (1.4); 4.019(1.3); 4.001(0.5); 3.323(141.8); 2.741(0.3); 2.699(0.4); 2.670(2.2); 2.501(348.2); 2.497(312.6); 2.406(0.8); 2.385(0.4); 2.328(2.2); 1.988(5.2); 1.397(0.7); 1.192(1.5); 1.184(0.7); 1.174(3.0); 1.157(1.5); 0.145(1.3); 0.007(8.6); −0.001(247.8); −0.150(1.3) |
| I-1-87 | 2.46 | 1H NMR (400.0 MHz, d6-DMSO): δ = 11.344(6.5); 8.907(4.1); 8.800(6.5); 8.316(0.8); 8.277(6.9); 8.224(0.3); 8.167(2.4); 8.149(2.7); 8.146(2.1); 8.026(15.2); 8.007(16.0); 7.941(8.8); 7.920(8.7); 7.832(6.8); 7.816(8.6); 7.793(4.2); 7.774(6.7); 7.756(8.1); 7.753(7.8); 7.704(13.7); 7.688(10.7); 7.685(10.9); 7.666(5.1); 7.514(0.5); 7.501(0.4); 7.477(0.4); 6.182(3.7); 5.577 (6.1); 4.056(0.7); 4.038(2.2); 4.020(2.2); 4.002(0.7); 3.324(131.6); 2.675(1.3); 2.671(1.8); 2.666(1.3); 2.524(4.3); 2.510(101.3); 2.506(206.5); 2.502(275.7); 2.497(205.1); 2.493(104.3); 2.333(1.3); 2.328(1.8); 2.324(1.4); 2.180(0.4); 1.989(9.5); 1.398(0.5); 1.259(0.4); 1.235(6.0); 1.193(2.5); 1.183(0.4); 1.175(5.0); 1.157(2.5); 0.854(0.6); 0.146(0.4); 0.008(2.9); 0.000(83.0); −0.008(3.8); −0.150(0.4) |
| I-1-88 | 2.26 | 1H NMR (400.0 MHz, d6-DMSO): δ = 11.558(1.1); 11.263(3.6); 9.339(0.8); 8.907(0.3); 8.828(0.4); 8.783(4.3); 8.315(1.4); 8.223(1.1); 8.205(1.2); 8.201(1.0); 8.024(16.0); 8.004(16.0); 7.803(0.7); 7.784(0.7); 7.743(0.8); 7.730(1.7); 7.710(1.6); 7.692(0.8); 7.577(3.5); 7.560(4.1); 7.540(4.9); 7.522(7.8); 7.506(6.8); 7.486(5.6); 7.461(3.3); 7.438(4.7); 7.421(5.9); 7.404(3.6); 4.055(0.9); 4.038(2.9); 4.020(3.0); 4.002(1.0); 3.323(148.9); 2.675(1.9); 2.671(2.7); 2.666 (2.0); 2.524(6.4); 2.510(146.4); 2.506(303.1); 2.501(408.1); 2.497(302.6); 2.492(151.9); 2.337 (0.9); 2.333(1.9); 2.328(2.7); 2.324(2.0); 1.989(13.0); 1.398(0.7); 1.348(0.5); 1.235(1.3); 1.193 (3.5); 1.175(7.0); 1.157(3.4); 1.119(0.5); 0.146(0.5); 0.008(3.9); 0.000(117.0); −0.009 (5.0); −0.150(0.5) |
| I-1-89 | 1.76 | See Synthesis Example 5 |
| I-2-1 | 2.19 | See Synthesis Example 7 |
| I-2-2 | 2.35 | See Synthesis Example 8 |
| I-2-3 | 2.57 | See Synthesis Example 9 |
| I-1-90 | 2.31 | 1H NMR (400.0 MHz, d6 DMSO): δ = 11.268 (2.7); 10.974 (0.5); 8.897 (1.3); 8.862 (2.6); 8.316 (0.5); 8.010 (0.6); 7.992 (0.6); 7.988 (0.5); 7.898 (3.1); 7.842 (2.5); 7.824 (3.1); 7.775 (2.2); 7.764 (2.2); 7.705 (4.2); 7.627 (0.6); 7.615 (0.5); 7.609 (0.7); 7.591 (0.5); 7.545 (0.7); 7.526 (0.9); 7.508 (0.7); 7.474 (3.1); 5.755 (15.8); 4.210 (1.0); 4.184 (2.3); 4.156 (2.6); 4.129 (1.7); 4.115 (1.7); 4.087 (1.0); 4.056 (0.6); 4.038 (0.8); 4.020 (0.8); 3.323 (77.3); 2.891 (0.4); 2.680 (0.5); 2.675 (1.0); 2.671 (1.3); 2.666 (1.0); 2.524 (3.6); 2.519 (5.3); 2.510 (71.7); 2.506 (147.9); 2.502 (197.1); 2.497 (144.6); 2.493 (71.5); 2.422 (16.0); 2.349 (9.1); 2.329 (3.9); 1.989 (2.6); 1.235 (0.5); 1.215 (1.8); 1.193 (0.7); 1.188 (1.3); 1.183 (1.9); 1.175 (2.4); 1.157 (0.7); 0.146 (1.0); 0.008 (7.5); 0.000 (224.6); −0.008 (8.7); −0.150 (1.0) |
| I-1-91 | 1.82 | 1H NMR (400.0 MHz, d6 DMSO): δ = 11.432 (11.2); 8.939 (16.0); 8.705 (1.0); 8.612 (1.0); 8.385 (6.0); 8.365 (6.6); 8.318 (0.8); 8.283 (0.9); 8.169 (0.8); 8.151 (0.4); 8.147 (0.4); 7.821 (4.1); 7.807 (5.2); 7.791 (4.1); 7.761 (1.4); 7.741 (3.0); 7.724 (4.7); 7.705 (4.1); 7.686 (2.4); 7.668 (1.5); 7.491 (6.8); 7.469 (12.0); 7.448 (6.3); 7.366 (1.5); 6.191 (0.5); 4.056 (1.0); 4.038 (3.2); 4.020 (3.2); 4.003 (1.1); 3.362 (0.9); 3.336 (223.8); 3.185 (0.5); 2.677 (0.9); 2.672 (1.2); 2.668 (0.9); 2.526 (3.0); 2.508 (136.4); 2.503 (178.3); 2.499 (135.0); 2.335 (0.9); 2.330 (1.2); 2.326 (0.9); 1.990 (14.0); 1.397 (1.1); 1.193 (3.7); 1.175 (7.3); 1.157 (3.6); 0.008 (1.4); 0.000 (38.1); −0.008 (1.9) |
| I-1-92 | 2.04 | 1H NMR (400.0 MHz, d6 DMSO): δ = 13.379 (0.9); 11.387 (9.2); 8.951 (6.4); 8.909 (1.7); 8.500 (10.2); 8.318 (0.4); 8.298 (1.2); 8.280 (2.4); 8.271 (2.5); 8.260 (1.9); 8.253 (4.3); 8.245 (1.9); 8.234 (2.5); 8.226 (2.5); 8.207 (1.1); 8.168 (0.9); 8.150 (1.1); 8.146 (1.9); 8.127 (2.2); 8.119 (2.2); 8.109 (1.3); 8.100 (4.0); 8.092 (1.3); 8.082 (2.1); 8.073 (2.1); 8.055 (0.9); 7.789 (5.3); 7.786 (3.6); 7.771 (4.6); 7.768 (4.5); 7.757 (0.6); 7.704 (0.8); 7.685 (1.1); 7.667 (0.5); 7.591 (3.6); 7.573 (4.5); 7.557 (5.3); 7.545 (12.8); 7.542 (16.0); 7.537 (15.9); 7.531 (9.5); 7.527 (8.2); 7.521 (4.9); 7.506 (7.0); 7.486 (3.4); 7.482 (3.0); 7.457 (5.0); 7.455 (5.0); 7.449 (5.2); 7.441 (8.4); 7.435 (7.3); 7.429 (4.9); 7.427 (4.4); 7.423 (5.2); 7.415 (3.5); 7.408 (2.6); 6.186 (1.3); 5.854 (13.9); 4.056 (1.1); 4.038 (3.4); 4.020 (3.5); 4.002 (1.2); 3.329 (60.5); 2.681 (0.4); 2.676 (0.8); 2.672 (1.2); 2.667 (0.9); |

| Compound No. | log P neutral | ¹H NMR data |
|---|---|---|
| | | 2.525 (2.6); 2.520 (3.9); 2.512 (64.9); 2.507 (136.6); 2.503 (184.2); 2.498 (134.9); 2.494 (65.6); 2.339 (0.4); 2.334 (0.9); 2.329 (1.2); 2.325 (0.9); 1.989 (15.5); 1.397 (3.5); 1.235 (1.8); 1.193 (4.2); 1.175 (8.2); 1.157 (4.1); 0.146 (1.0); 0.008 (7.9); 0.000 (245.1); −0.009 (8.8); −0.150 (1.0) |
| I-1-93 | 2.23 | 1H NMR (400.0 MHz, d6 DMSO): δ = 11.471 (11.6); 8.964 (8.9); 8.500 (8.3); 8.318 (1.1); 8.298 (1.9); 8.272 (4.8); 8.254 (6.9); 8.235 (4.9); 8.147 (0.9); 8.128 (1.7); 8.120 (1.7); 8.110 (1.2); 8.102 (3.0); 8.093 (1.2); 8.083 (1.7); 8.075 (1.6); 8.056 (0.8); 7.847 (11.0); 7.829 (14.5); 7.777 (8.7); 7.761 (9.3); 7.726 (15.9); 7.709 (16.0); 5.857 (12.7); 4.056 (0.4); 4.038 (1.2); 4.020 (1.2); 4.002 (0.4); 3.331 (334.7); 2.999 (0.4); 2.714 (0.4); 2.672 (2.7); 2.507 (324.5); 2.503 (403.1); 2.499 (304.6); 2.330 (2.7); 1.989 (5.3); 1.398 (2.4); 1.235 (0.7); 1.193 (1.4); 1.175 (2.7); 1.157 (1.4); 0.000 (57.2) |
| I-1-94 | 1.92 | 1H NMR (400.0 MHz, d6 DMSO): δ = 10.952 (0.3); 10.925 (12.8); 8.918 (16.0); 8.447 (0.3); 7.819 (13.4); 7.805 (14.2); 7.769 (1.0); 7.755 (2.1); 7.752 (1.6); 7.739 (3.5); 7.733 (2.7); 7.723 (2.0); 7.717 (5.6); 7.712 (2.5); 7.701 (2.8); 7.696 (3.7); 7.680 (1.7); 7.647 (0.6); 7.643 (0.8); 7.484 (8.9); 7.462 (15.0); 7.442 (7.3); 7.365 (11.1); 7.351 (10.6); 7.250 (1.1); 7.236 (1.0); 6.932 (0.9); 6.919 (0.9); 6.189 (0.4); 3.361 (0.6); 3.332 (90.6); 3.183 (0.5); 2.985 (3.5); 2.825 (3.5); 2.676 (0.6); 2.672 (0.9); 2.667 (0.6); 2.525 (2.2); 2.511 (50.1); 2.507 (99.4); 2.503 (129.7); 2.498 (96.9); 2.494 (49.5); 2.334 (0.6); 2.329 (0.9); 2.325 (0.6); 1.989 (1.4); 1.235 (1.2); 1.193 (0.5); 1.175 (0.8); 1.157 (0.4); 0.008 (1.1); 0.000 (28.0); −0.008 (1.3) |
| I-1-95 | 2.33 | 1H NMR (400.0 MHz, d6 DMSO): δ = 10.930 (3.3); 8.762 (5.2); 8.017 (2.4); 7.997 (2.9); 7.939 (1.0); 7.921 (2.5); 7.902 (1.9); 7.848 (1.9); 7.829 (2.6); 7.810 (1.1); 7.764 (2.5); 7.745 (2.1); 7.459 (0.6); 7.445 (1.7); 7.428 (2.7); 7.410 (2.7); 7.392 (2.0); 7.330 (3.5); 7.311 (2.3); 7.291 (1.9); 7.272 (2.8); 7.253 (1.2); 3.330 (25.7); 2.923 (0.8); 2.904 (0.9); 2.774 (1.6); 2.755 (4.9); 2.737 (5.0); 2.718 (1.7); 2.671 (0.4); 2.666 (0.3); 2.524 (1.1); 2.510 (24.4); 2.506 (49.3); 2.502 (64.8); 2.497 (48.0); 2.493 (24.1); 2.329 (0.4); 1.195 (7.3); 1.176 (16.0); 1.157 (7.3); 1.153 (3.8); 1.134 (1.1); 0.000 (8.5); −0.008 (0.4) |
| I-1-96 | 2.49 | 1H NMR (400.0 MHz, d6 DMSO): δ = 11.303 (2.1); 8.874 (2.1); 8.316 (0.8); 7.954 (2.0); 7.839 (1.9); 7.823 (2.4); 7.772 (1.8); 7.762 (1.8); 7.703 (3.4); 7.634 (2.9); 4.983 (1.3); 4.960 (3.6); 4.935 (3.7); 4.912 (1.5); 4.056 (1.2); 4.038 (3.6); 4.020 (3.6); 4.002 (1.2); 3.322 (90.1); 2.693 (12.6); 2.676 (3.6); 2.671 (3.5); 2.666 (2.6); 2.524 (4.6); 2.519 (6.8); 2.511 (103.8); 2.506 (216.3); 2.502 (290.2); 2.497 (213.7); 2.493 (105.7); 2.383 (5.5); 2.337 (1.3); 2.333 (1.9); 2.328 (2.4); 2.324 (1.8); 1.989 (16.0); 1.398 (4.1); 1.193 (4.3); 1.175 (8.5); 1.157 (4.2); 0.146 (2.1); 0.008 (15.7); 0.000 (462.7); −0.009 (18.0); −0.026 (0.5); −0.150 (2.1) |
| I-1-97 | 2.34 | 1H NMR (400.0 MHz, d6 DMSO): δ = 13.307 (0.7); 11.308 (16.0); 8.993 (6.9); 8.618 (9.2); 8.611 (9.3); 8.317 (0.4); 7.993 (1.9); 7.991 (2.0); 7.973 (2.1); 7.971 (2.1); 7.936 (8.6); 7.916 (9.2); 7.771 (1.3); 7.763 (1.6); 7.755 (1.8); 7.748 (2.8); 7.744 (2.8); 7.736 (2.9); 7.727 (2.9); 7.723 (3.0); 7.717 (3.3); 7.713 (3.1); 7.698 (2.7); 7.694 (2.2); 7.597 (1.5); 7.577 (2.3); 7.569 (2.2); 7.562 (2.1); 7.554 (2.7); 7.549 (2.3); 7.547 (2.3); 7.541 (2.6); 7.532 (2.3); 7.528 (2.6); 7.520 (2.1); 7.513 (3.5); 7.505 (2.5); 7.495 (9.1); 7.477 (15.2); 7.460 (4.7); 7.454 (3.6); 7.447 (3.4); 7.441 (2.4); 7.436 (2.5); 7.433 (2.2); 7.430 (2.4); 7.423 (2.8); 7.417 (2.0); 7.409 (1.3); 7.250 (4.9); 7.244 (4.0); 7.230 (6.7); 7.213 (3.7); 7.207 (3.5); 5.937 (13.6); 4.056 (1.2); 4.038 (3.6); 4.020 (3.6); 4.002 (1.2); 3.329 (84.4); 2.681 (0.5); 2.676 (1.2); 2.672 (1.6); 2.667 (1.2); 2.663 (0.6); 2.525 (4.1); 2.520 (6.2); 2.512 (89.7); 2.507 (183.7); 2.503 (242.7); 2.498 (175.4); 2.494 (83.9); 2.338 (0.5); 2.334 (1.1); 2.329 (1.6); 2.325 (1.1); 2.320 (0.5); 1.989 (15.9); 1.234 (0.4); 1.193 (4.2); 1.175 (8.4); 1.157 (4.2); 0.146 (1.3); 0.008 (9.9); 0.000 (302.0); −0.009 (10.1); −0.150 (1.3) |
| I-1-98 | 3.21 | 1H NMR (400.0 MHz, d6 DMSO): δ = 13.575 (0.3); 11.217 (3.2); 10.928 (0.5); 8.771 (1.4); 8.735 (3.2); 8.316 (0.6); 8.004 (0.6); 7.986 (0.6); 7.982 (0.5); 7.820 (3.5); 7.767 (2.8); 7.749 (2.4); 7.698 (5.0); 7.646 (4.6); 7.605 (1.1); 7.587 (0.8); 7.541 (0.7); 7.522 (0.9); 7.508 (0.4); 7.504 (0.5); 7.356 (3.8); 4.064 (1.8); 4.055 (2.3); 4.038 (5.9); 4.020 (5.5); 4.015 (4.9); 4.002 (3.0); 3.990 (2.2); 3.325 (84.9); 2.675 (0.8); 2.671 (1.1); 2.666 (0.8); 2.524 (2.3); 2.511 (61.7); 2.506 (128.3); 2.502 (172.9); 2.497 (128.9); 2.493 (65.1); 2.406 (16.0); 2.333 (1.4); 2.329 (1.6); 2.324 (1.3); 2.209 (9.8); 1.989 (6.9); 1.690 (0.4); 1.193 (1.8); 1.175 (3.6); 1.157 (1.7); 0.008 (0.8); 0.000 (26.9); −0.008 (1.1) |

1) Description of Method for Determination of the Log P Values (Formic Acid Method)

The log P values given in the table were determined in accordance with EEC Directive 79/831 Annex V.A8 by HPLC (High Performance Liquid Chromatography) using a reversed-phase column (C 18). Temperature: 55° C.

Eluents for determination in the acidic range (pH 3.4):

Eluent A: acetonitrile+1 ml of formic acid/liter. Eluent B: water+0.9 ml of formic acid/liter.

Gradient: from 10% eluent A/90% eluent B to 95% eluent A/5% eluent B in 4.25 min.

Calibration was effected with unbranched alkan-2-ones (having 3 to 16 carbon atoms) with known log P values (log P values determined on the basis of the retention times by linear interpolation between two successive alkanones). The lambda max values were determined in the maxima of the chromatographic signals using the UV spectra from 200 nm to 400 nm.

2) Measurement of the NMR Spectra

The NMR spectra were determined with a Bruker Avance 400 fitted with a flow probe head (volume 60 μl). Solvents used were $CD_3CN$ or DMSO-$D_6$, and tetramethylsilane (0.00 ppm) was used as reference. In isolated cases, the NMR spectra were determined using a Bruker Avance II 600. Solvents used were $CD_3CN$ or DMSO-$D_6$, and tetramethylsilane (0.00 ppm) was used as reference.

The splitting of the signals was described as follows: s (singlet), d (doublet), t (triplet), q (quartet), quin (quintet), m (multiplet).

NMR Peak List Method

When the 1H NMR data for selected examples are noted in the form of 1H NMR peak lists, first the d value in ppm and then the signal intensity in round brackets are listed for each signal peak. The d value—signal intensity number pairs for different signal peaks are listed with separation from one another by semicolons.

The peak list for one example therefore takes the form of:
δ1 (intensity1); δ2 (intensity2); . . . ; δi (intensityi); . . . ; δn (intensityn)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form the subject-matter of the invention, and/or peaks of impurities.

In the reporting of compound signals in the delta range of solvents and/or water, our lists of 1H NMR peaks show the usual solvent peaks, for example peaks of DMSO in DMSO-D6 and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in Research Disclosure Database Number 564025.

Use Examples

The examples which follow demonstrate the insecticidal, acaricidal and nematicidal action of the compounds according to the invention. In these examples, the inventive compounds cited relate to the compounds listed in Tables 1 and 2 with the corresponding reference numerals, e.g. I-1-1:

Boophilus microplus—Injection Test
Solvent: dimethyl sulphoxide
To produce an appropriate active ingredient formulation, 10 mg of active ingredient are mixed with 0.5 ml of solvent and the concentrate is diluted with solvent to the desired concentration.

1 μl of the active ingredient solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet for about another 42 days until the larvae hatch. An efficacy of 100% means that none of the ticks has laid any fertile eggs; 0% means that all the eggs are fertile.

In this test, for example, the following compounds from the preparation examples showed an efficacy of 100% at an application rate of 20 μg/animal I-1-10, I-1-11, I-1-24, I-1-30, I-1-33, I-1-59, I-1-65

In this test, for example, the following compounds from the preparation examples showed an efficacy of 90% at an application rate of 20 μg/animal I-1-44, I-1-57

In this test, for example, the following compounds from the preparation examples showed an efficacy of 80% at an application rate of 20 μg/animal: I-1-18

Cooperia curticei Test
Solvent: dimethyl sulphoxide
To produce an appropriate active ingredient formulation, 10 mg of active ingredient are mixed with 0.5 ml of dimethyl sulphoxide and the concentrate is diluted with "Ringer's solution" to the desired concentration.

Vessels containing the active ingredient formulation of the desired concentration are populated with about 40 nematode larvae (*Cooperia curticei*).

After 5 days, the kill in % is determined 100% means that all the larvae have been killed; 0% means that none of the larvae have been killed.

In this test, for example, the following compounds from the preparation examples showed an efficacy of 100% at an application rate of 20 ppm: I-1-20, I-1-21, I-1-33, I-1-57, I-1-63

In this test, for example, the following compounds from the preparation examples showed an efficacy of 90% at an application rate of 20 ppm: I-1-26, I-1-59

In this test, for example, the following compounds from the preparation examples showed an efficacy of 80% at an application rate of 20 ppm: I-1-28, I-1-30, I-1-61, I-1-70, I-1-83, I-1-85

Haemonchus contortus Test
Solvent: dimethyl sulphoxide
To produce an appropriate active ingredient formulation, 10 mg of active ingredient are mixed with 0.5 ml of dimethyl sulphoxide and the concentrate is diluted with "Ringer's solution" to the desired concentration.

Vessels containing the active ingredient formulation of the desired concentration are populated with about 40 larvae of the red stomach worm (*Haemonchus contortus*).

After 5 days, the kill in % is determined 100% means that all the larvae have been killed; 0% means that none of the larvae have been killed.

In this test, for example, the following compounds from the preparation examples showed an efficacy of 80% at an application rate of 20 ppm: I-1-21

Lucilia cuprina Test
Solvent: dimethyl sulphoxide
To produce an appropriate active ingredient formulation, 10 mg of active ingredient are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active ingredient preparation of the desired concentration.

After 2 days, the kill in % is determined 100% means that all the larvae have been killed; 0% means that no larvae have been killed.

In this test, for example, the following compounds from the preparation examples showed an efficacy of 100% at an application rate of 100 ppm: I-1-11, I-1-24

*Musca domestica* Test

Solvent: dimethyl sulphoxide

To produce an appropriate active ingredient formulation, 10 mg of active ingredient are mixed with 0.5 ml of dimethyl sulphoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the kill in % is determined 100% means that all of the flies have been killed; 0% means that none of the flies have been killed.

In this test, for example, the following compounds from the preparation examples showed an efficacy of 80% at an application rate of 100 ppm: I-1-11, I-1-24

*Meloidogyne incognita* Test (MELGIN)

Solvent: 125.0 parts by weight of acetone

To produce a suitable active ingredient formulation, 1 part by weight of active ingredient is mixed with the stated amount of solvent and the concentrate is diluted with water to the desired concentration.

Vessels are filled with sand, active ingredient solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples showed an efficacy of 100% at an application rate of 20 ppm: I-1-8, I-1-10, I-1-13, I-1-14, I-1-15, I-1-18, I-1-19, I-1-20, I-1-21, I-1-24, I-1-26, I-1-28, I-1-29, I-1-30, I-1-31, I-1-32, I-1-33, I-1-35, I-1-44, I-1-45, I-1-57, I-1-58, I-1-59, I-1-60, I-1-61, I-1-62, I-1-63, I-1-64, I-1-80, I-1-83, I-1-85, I-1-89, I-1-91, I-1-93

In this test, for example, the following compounds from the preparation examples showed an efficacy of 90% at an application rate of 20 ppm: I-1-4, I-1-11, I-1-12, I-1-22, I-1-27, I-1-40, I-1-42, I-1-46, I-1-67, I-1-70, I-1-75, I-1-87, I-1-92

*Myzus persicae*—Spray Test

Solvent: 78 parts by weight of acetone 1.5 parts by weight of dimethylformamide

Emulsifier: alkylaryl polyglycol ether

To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 6 days, the efficacy in % is determined 100% means that all the aphids have been killed; 0% means that no aphids have been killed.

In this test, for example, the following compounds from the preparation examples showed an efficacy of 90% at an application rate of 500 g/ha: I-1-72

*Phaedon cochleariae*—Spray Test (PHAECO)

Solvent: 78.0 parts by weight of acetone 1.5 parts by weight of dimethylformamide Emulsifier: alkylaryl polyglycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined 100% means that all the beetle larvae have been killed; 0% means that no beetle larvae have been killed.

In this test, for example, the following compounds from the preparation examples showed an efficacy of 100% at an application rate of 500 g/ha: I-1-33, I-1-91, I-2-3

In this test, for example, the following compounds from the preparation examples showed an efficacy of 83% at an application rate of 500 g/ha: I-1-18

*Tetranychus urticae*—Spray Test, OP-Resistant

Solvent: 78.0 parts by weight of acetone 1.5 parts by weight of dimethylformamide Emulsifier: alkylaryl polyglycol ether To produce an appropriate active ingredient formulation, 1 part by weight of active ingredient is dissolved using the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active ingredient formulation of the desired concentration.

After 6 days, the efficacy in % is determined. 100% means that all the spider mites have been killed; 0% means that no spider mites have been killed.

In this test, for example, the following compounds from the preparation examples showed an efficacy of 95% at an application rate of 500 g/ha: I-1-90

The invention claimed is:

1. Compound of formula (I)

in which

A is a radical from the group of

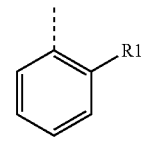

A-1

-continued

A-2 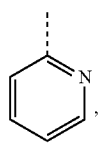

A-3 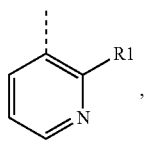

A-4 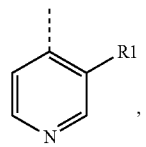

A-5 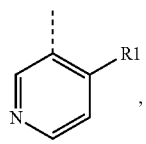

A-6 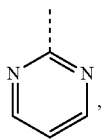

A-7 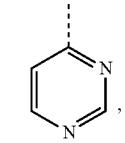

A-8 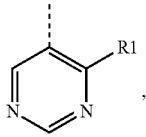

A-9 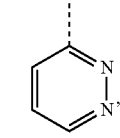

A-10 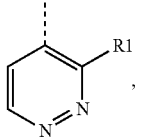

A-11 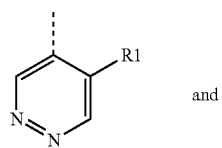
and

-continued

A-12 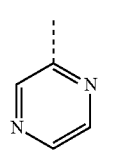

in which the broken line denotes the bond to Q and where A additionally bears m R2 substituents, Q is a radical from the group of Q-1 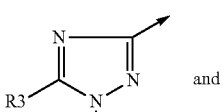
and Q-2 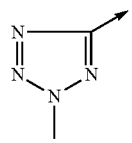

in which the nitrogen is joined to the ring A and the arrow in each case denotes the bond to D, and D is the radical of the formula

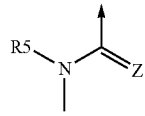

in which the nitrogen is bonded to Q and the arrow denotes the bond to B,

B is a radical from the group of

B-1 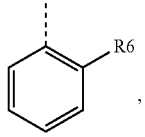

B-2 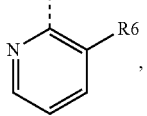

B-3 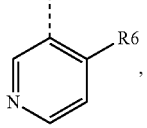

B-4 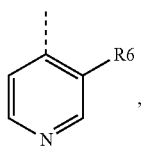

-continued
B-5 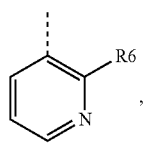
B-6 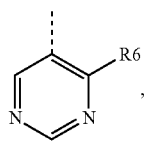
B-7 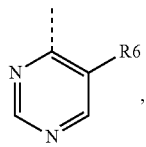
B-8 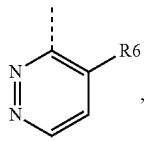
B-9 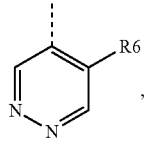
B-10 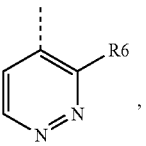
B-11 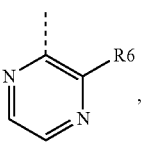
B-12 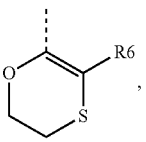
B-13 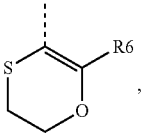
B-14 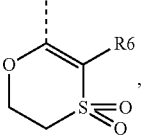
-continued
B-15 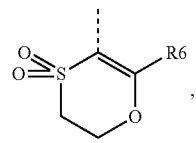
B-16 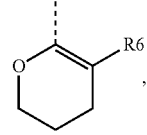
B-17 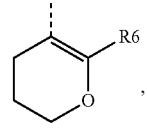
B-18 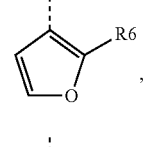
B-19 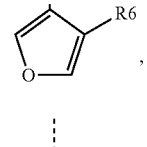
B-20 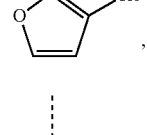
B-21 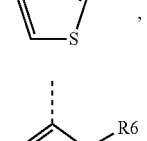
B-22 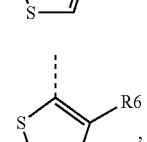
B-23 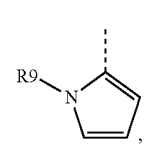
B-24 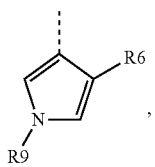
B-25

-continued
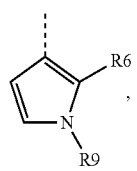  B-26
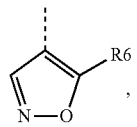  B-27
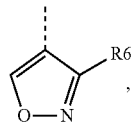  B-28
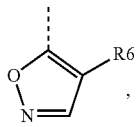  B-29
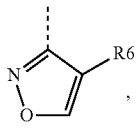  B-30
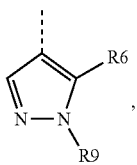  B-31
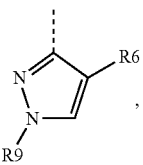  B-32
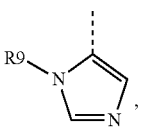  B-33
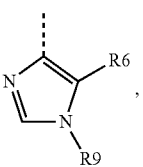  B-34
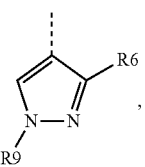  B-35
-continued
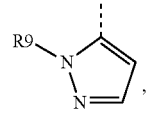  B-36
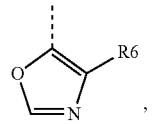  B-37
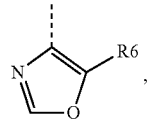  B-38
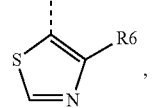  B-39
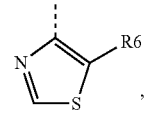  B-40
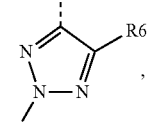  B-41
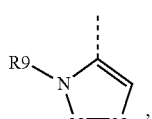  B-42
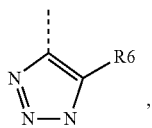  B-43
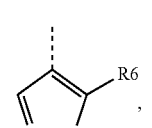  B-44
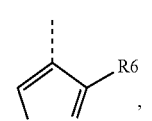  B-45
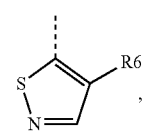  B-46

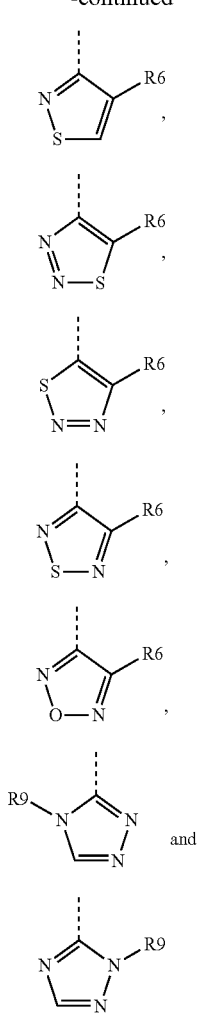

in which the broken line denotes the bond to D and where B additionally bears n R7 substituents, Z is oxygen or sulphur, R1 is a radical from the group of hydrogen (but only in the case of the combination of A-1 with Q-2), halogen, cyano, nitro, amino, hydroxyl, optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)aminocarbonyl, aminothiocarbonyl, $C_1$-$C_6$-alkylaminosulphonyl, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, aryl, aryloxy, arylthio, heteroaryl, heteroaryloxy and heteroarylthio, R2 is a radical from the group of halogen, cyano, nitro, amino, hydroxyl, optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, aryl, aryloxy, arylthio, heteroaryl, heteroaryloxy and heteroarylthio, R3 is a radical from the group of hydrogen, halogen, cyano, nitro, amino, hydroxyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-haloalkyl, $C_1$-$C_6$-haloalkoxy, $C_1$-$C_6$-haloalkylthio, $C_1$-$C_6$-haloalkylsulphinyl and $C_1$-$C_6$-haloalkylsulphonyl, R4 is a radical from the group of hydrogen, halogen, cyano, nitro, amino, hydroxyl, $C_1$-$C_6$-alkyl, $C_1$-$C_6$-alkoxy, $C_1$-$C_6$-haloalkyl and $C_1$-$C_6$-haloalkoxy, R5 is a radical from the group of hydrogen, $C_1$-$C_6$-alkyl, $C_3$-$C_6$-cycloalkyl, $C_1$-$C_6$-haloalkyl, $C_2$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl or is C(=O)—B, R6 is a radical from the group of halogen, cyano, nitro, amino, hydroxyl, in each case singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenyloxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, $C_4$-$C_{12}$-bicycloalkyl, aryl, aryloxy, heteroaryl and heteroaryloxy, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, R7 is a radical from the group of halogen, nitro, cyano, amino, hydroxyl, in each case optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, $C_4$-$C_{12}$-bicycloalkyl, aryl, aryloxy, heteroaryl and heteroaryloxy, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, R9 is a radical from the group of hydrogen, $C_1$-$C_6$-alkyl, $C_3$-$C_6$-cycloalkyl, haloalkyl, $C_3$-$C_6$-alkenyl, $C_2$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl, m is a number from the group of 0, 1, 2, 3 and 4, where, when m>1, the R2 radicals may be the same or different, and n is a number from the group of 0, 1, 2 and 3, where, when n>1, the R7 radicals may be the same or different, excluding the compound of formula

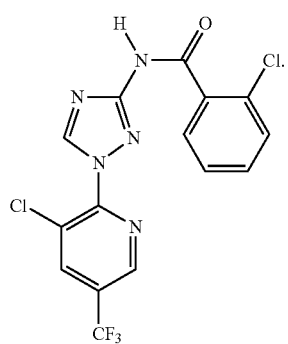 [SMILES: O=C(Nc1ncn(-c2ncc(C(F)(F)F)cc2Cl)n1)c1ccccc1Cl]

2. Compound of formula (I) according to claim 1, in which

A is a radical from the group of

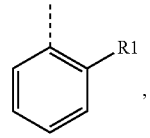
A-1

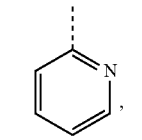
A-2

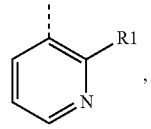
A-3

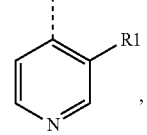
A-4

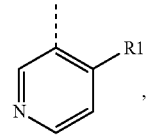
A-5

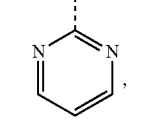
A-6

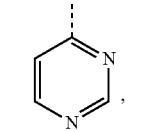
A-7

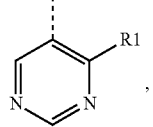
A-8

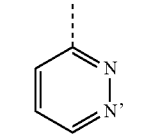
A-9

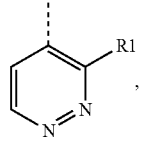
A-10

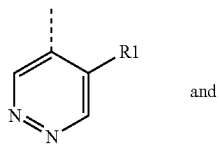 A-11
and
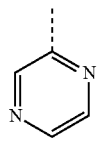 A-12
in which the broken line denotes the bond to Q and where A additionally bears m R2 substituents,
Q is
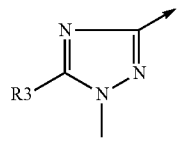 Q-1
in which the nitrogen is joined to the ring A and the arrow in each case denotes the bond to D,
D is the radical of the formula
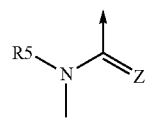
in which the nitrogen is bonded to Q and the arrow denotes the bond to B,
B is a radical from the group of
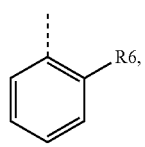 B-1
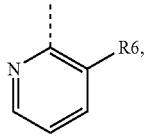 B-2
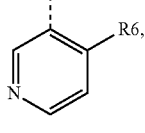 B-3
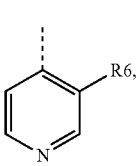 B-4
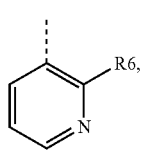 B-5
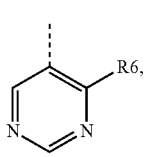 B-6
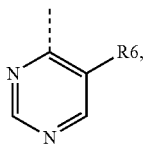 B-7
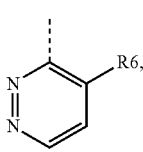 B-8
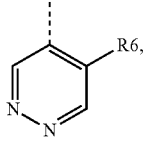 B-9
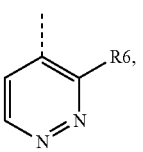 B-10
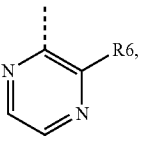 B-11
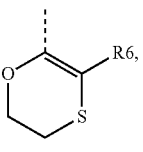 B-12
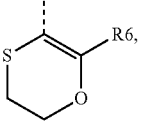 B-13

B-14 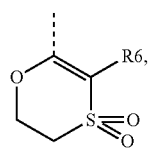
B-15 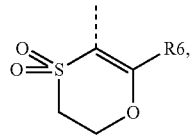
B-16 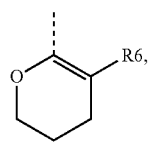
B-17 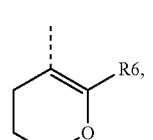
B-18 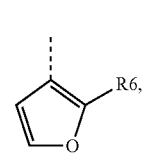
B-19 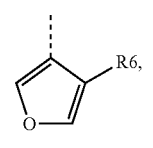
B-20 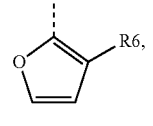
B-21 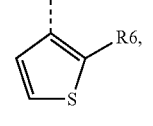
B-22 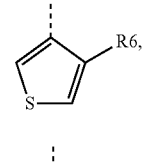
B-23 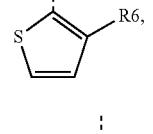
B-24 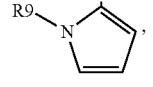
B-25 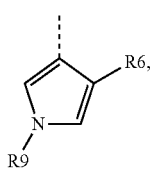
B-26 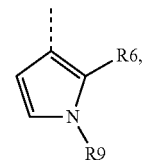
B-27 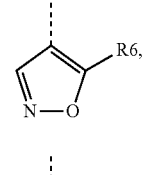
B-28 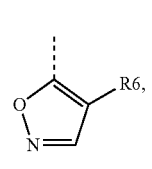
B-29 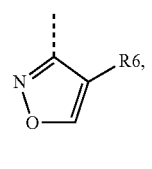
B-30 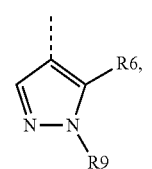
B-31 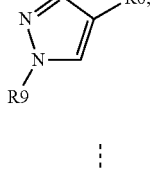
B-32 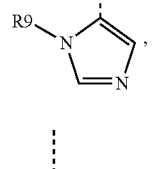
B-33 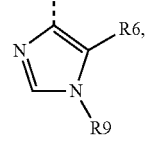
B-34

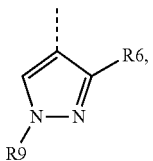 B-35

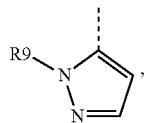 B-36

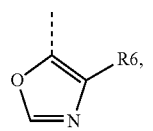 B-37

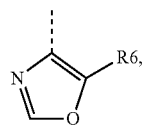 B-38

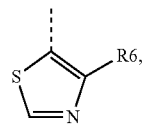 B-39

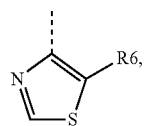 B-40

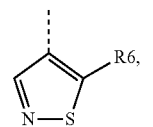 B-44

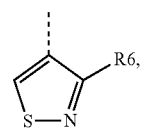 B-45

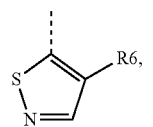 B-46

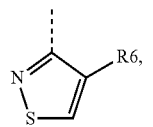 B-47

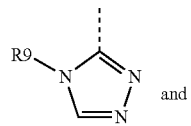 B-52

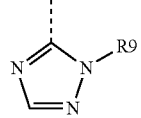 B-53 in which the broken line denotes the bond to D and where B additionally bears n R7 substituents, Z is oxygen or sulphur, R1 is a radical from the group of hydrogen (but only in the case of the combination of A-1 with Q-2), halogen, cyano, nitro, amino, hydroxyl, $C_1$-$C_6$-alkyl, $C_1$-$C_6$ haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$ cycloalkyl $C_1$-$C_6$ alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$ alkylamino, $C_3$-$C_6$-alkenylamino, $C_3$-$C_6$-alkynylamino, $C_3$-$C_6$-cycloalkylamino, $C_1$-$C_6$ alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$ alkylsulphinyl, $C_1$-$C_6$-alkylsulphonyl, $C_1$-$C_6$-haloalkylsulphinyl, $C_1$-$C_6$-haloalkylsulphonyl, $C_1$-$C_6$-alkylcarbonyl, $C_1$-$C_6$ alkoxyimino $C_1$-$C_6$ alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, heteroaryl and heteroaryloxy, R2 is a radical from the group of halogen, cyano, nitro, amino, hydroxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_3$-$C_6$-halocycloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, heteroaryl and heteroaryloxy, R3 is a radical from the group of hydrogen, halogen, cyano, nitro, amino, hydroxyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-haloalkyl, $C_1$-$C_6$-haloalkoxy, $C_1$-$C_6$-haloalkylthio, $C_1$-$C_6$-haloalkylsulphinyl and $C_1$-$C_6$-haloalkylsulphonyl, R5 is a radical from the group of hydrogen, $C_1$-$C_6$-alkyl, $C_3$-$C_6$-cycloalkyl, $C_1$-$C_6$-haloalkyl, $C_2$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, C$_1$-C$_6$-alkoxy-C$_1$-C$_6$-alkyl, C$_1$-C$_6$-alkoxycarbonyl, C$_1$-C$_6$-alkylsulphonyl, C$_1$-C$_6$-haloalkylsulphonyl and C(=O)—B, R6 is a radical from the group of halogen, cyano, nitro, amino, hydroxyl, C$_1$-C$_6$-alkyl, C$_1$-C$_6$-haloalkyl, cyano-C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, C$_1$-C$_6$-alkoxy, C$_1$-C$_6$-haloalkoxy, C$_3$-C$_6$-alkenyloxy, C$_3$-C$_6$-alkynyloxy, C$_3$-C$_6$-cycloalkyloxy, C$_1$-C$_6$-alkylcarbonyloxy, C$_2$-C$_6$-alkenylcarbonyloxy, C$_2$-C$_6$-alkynylcarbonyloxy, C$_3$-C$_6$-cycloalkylcarbonyloxy, C$_1$-C$_6$-alkoxycarbonyloxy, C$_1$-C$_6$-alkylsulphonyloxy, C$_3$-C$_6$-alkenylcarbonylamino, C$_3$-C$_6$-alkynylcarbonylamino, C$_3$-C$_6$-cycloalkylcarbonylamino, C$_1$-C$_6$-alkylthio, C$_1$-C$_6$-haloalkylthio, C$_1$-C$_6$-alkylsulphinyl, C$_1$-C$_6$-haloalkylsulphinyl, C$_1$-C$_6$-alkylsulphonyl, C$_1$-C$_6$-haloalkylsulphonyl, C$_1$-C$_6$-alkylcarbonyl, C$_1$-C$_6$-alkoxyimino-C$_1$-C$_6$-alkyl, C$_1$-C$_6$-alkoxycarbonyl, aminocarbonyl, C$_1$-C$_6$-alkylaminocarbonyl, di-(C$_1$-C$_6$-alkyl)-aminocarbonyl, aminothiocarbonyl, C$_1$-C$_6$-alkylaminosulphonyl, C$_1$-C$_6$-alkylsulphonylamino, C$_1$-C$_6$-alkylcarbonylamino, C$_1$-C$_6$-alkylthiocarbonylamino, aryl, aryloxy, heteroaryl and heteroaryloxy, R7 is a radical from the group of halogen, cyano, nitro, amino, hydroxyl, C$_1$-C$_6$-alkyl, C$_1$-C$_6$-haloalkyl, cyano-C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, C$_1$-C$_6$-alkoxy, C$_1$-C$_6$-haloalkoxy, C$_3$-C$_6$-alkenyloxy, C$_3$-C$_6$-alkynyloxy, C$_3$-C$_6$-cycloalkyloxy, C$_1$-C$_6$-alkylcarbonyloxy, C$_2$-C$_6$-alkenylcarbonyloxy, C$_2$-C$_6$-alkynylcarbonyloxy, C$_3$-C$_6$-cycloalkylcarbonyloxy, C$_1$-C$_6$-alkoxycarbonyloxy, C$_1$-C$_6$-alkylsulphonyloxy, C$_3$-C$_6$-alkenylcarbonylamino, C$_3$-C$_6$-alkynylcarbonylamino, C$_3$-C$_6$-cycloalkylcarbonylamino, C$_1$-C$_6$-alkylthio, C$_1$-C$_6$-haloalkylthio, C$_1$-C$_6$-alkylsulphinyl, C$_1$-C$_6$-haloalkylsulphinyl, C$_1$-C$_6$-alkylsulphonyl, C$_1$-C$_6$-haloalkylsulphonyl, C$_1$-C$_6$-alkylcarbonyl, C$_1$-C$_6$-alkoxyimino-C$_1$-C$_6$-alkyl, C$_1$-C$_6$-alkoxycarbonyl, aminocarbonyl, C$_1$-C$_6$-alkylaminocarbonyl, di-(C$_1$-C$_6$-alkyl)-aminocarbonyl, aminothiocarbonyl, C$_1$-C$_6$-alkylaminosulphonyl, C$_1$-C$_6$-alkylsulphonylamino, C$_1$-C$_6$-alkylcarbonylamino, C$_1$-C$_6$-alkylthiocarbonylamino, aryl, aryloxy, heteroaryl and heteroaryloxy, R9 is a radical from the group of hydrogen, C$_1$-C$_6$-alkyl, C$_3$-C$_6$-cycloalkyl, C$_1$-C$_6$-haloalkyl, C$_3$-C$_6$-alkenyl, C$_2$-C$_6$-alkynyl, C$_3$-C$_6$-cycloalkyl-C$_1$-C$_6$-alkyl, cyano-C$_1$-C$_6$-alkyl, C$_1$-C$_6$-alkylcarbonyl, C$_2$-C$_6$-alkenylcarbonyl, C$_1$-C$_6$-haloalkylcarbonyl, C$_2$-C$_6$-haloalkenylcarbonyl, C$_1$-C$_6$-alkoxy-C$_1$-C$_6$-alkyl, C$_1$-C$_6$-alkoxycarbonyl, C$_1$-C$_6$-alkylsulphonyl and C$_1$-C$_6$-haloalkylsulphonyl, m is a number from the group of 0, 1, 2, 3 and 4, where, when m>1, the R2 radicals may be the same or different, and n is a number from the group of 0, 1, 2 and 3, where, when n>1, the R7 radicals may be the same or different.

3. Compound of formula (I) according to claim 1, in which

A is a radical from the group of

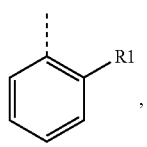
A-1

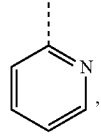
A-2

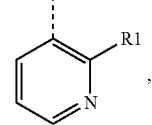
A-3

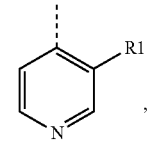
A-4

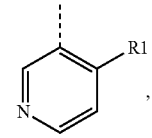
A-5

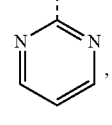
A-6

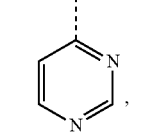
A-7

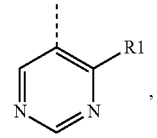
A-8

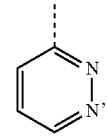
A-9

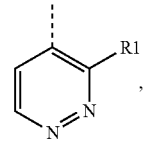
A-10

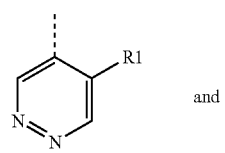
and
A-11

-continued

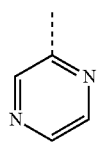
A-12 in which the broken line denotes the bond to Q and where A additionally bears m R2 substituents,
Q is a radical from the group of

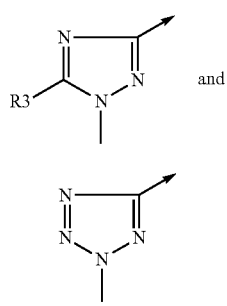
Q-1 and

Q-2 in which the nitrogen is joined to the ring A and the arrow in each case denotes the bond to D,
D is the radical of the formula

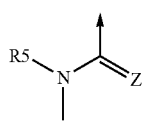

in which the nitrogen is bonded to Q and the arrow denotes the bond to B,
B is a radical from the group of

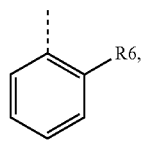
B-1

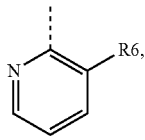
B-2

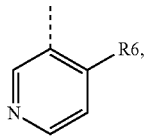
B-3

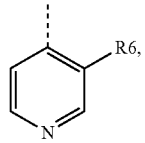
B-4

-continued

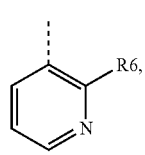
B-5

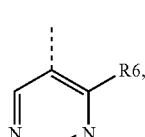
B-6

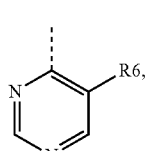
B-7

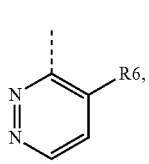
B-8

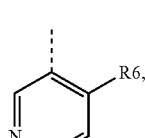
B-9

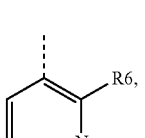
B-10

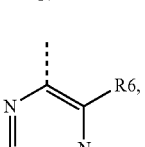
B-11

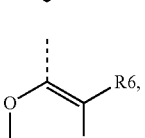
B-12

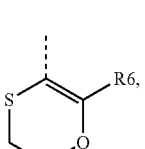
B-13

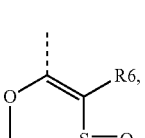
B-14

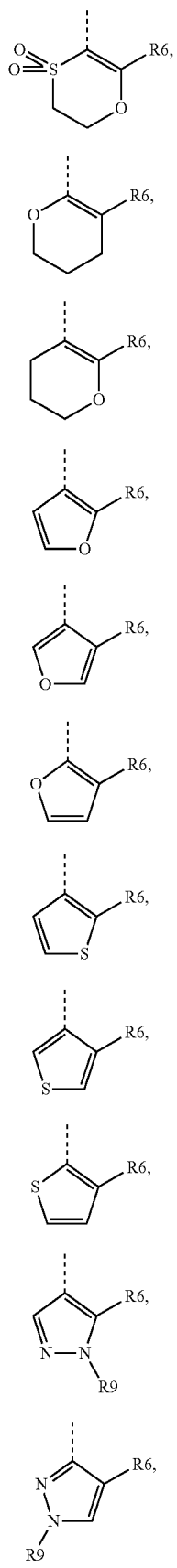
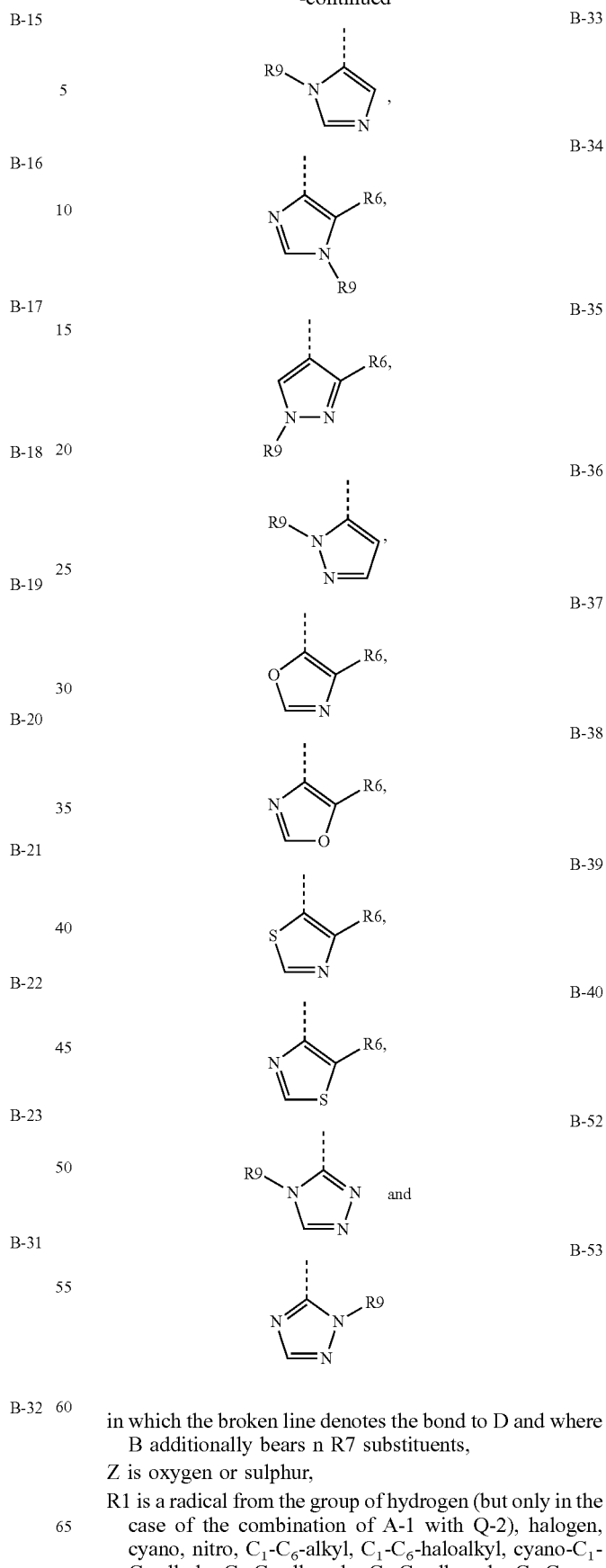
in which the broken line denotes the bond to D and where B additionally bears n R7 substituents,
Z is oxygen or sulphur,
R1 is a radical from the group of hydrogen (but only in the case of the combination of A-1 with Q-2), halogen, cyano, nitro, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, aryloxy, heteroaryl and heteroaryloxy, R2 is a radical from the group of halogen, cyano, nitro, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkoxyimino-$C_1$-$C_6$-alkyl, aryl, aryloxy, heteroaryl and heteroaryloxy, R3 is a radical from the group of hydrogen, halogen, cyano, nitro, amino, hydroxyl, $C_1$-$C_6$-alkyl and $C_1$-$C_6$-haloalkyl, R5 is a radical from the group of hydrogen, $C_1$-$C_6$-alkyl, $C_3$-$C_6$-cycloalkyl, $C_1$-$C_6$-haloalkyl, $C_2$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl, $C_1$-$C_6$-haloalkylsulphonyl and C(=O)—B, R6 is a radical from the group of halogen, cyano, nitro, hydroxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, aryloxy, heteroaryl and heteroaryloxy, R7 is a radical from the group of halogen, cyano, nitro, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, aryloxy, heteroaryl and heteroaryloxy, R9 is a radical from the group of hydrogen, $C_1$-$C_6$-alkyl, $C_3$-$C_6$-cycloalkyl and $C_1$-$C_6$-haloalkyl, m is a number from the group of 0, 1, 2, 3 and 4, where, when m>1, the R2 radicals may be the same or different, and n is a number from the group of 0, 1 and 2, where, when n>1, the R7 radicals may be the same or different.

4. Compound of formula (I) according to claim 1, in which

A is a radical from the group of

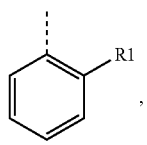

A-1

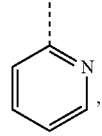

A-2

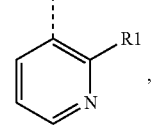

A-3

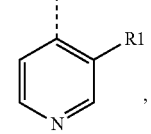

A-4

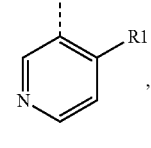

A-5

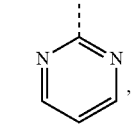

A-6

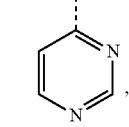

A-7

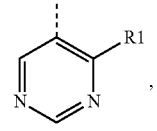

A-8

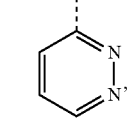

A-9

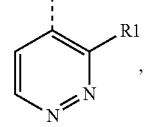

A-10

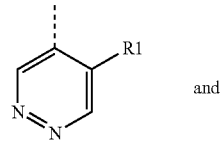

A-11 and

-continued

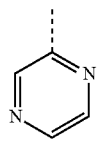
A-12 in which the broken line denotes the bond to Q and where A additionally bears m R2 substituents,
Q is a radical from the group of

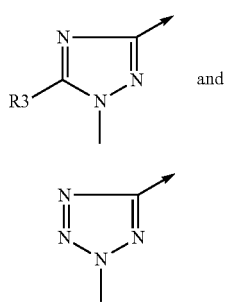
Q-1 and

Q-2 in which the nitrogen is joined to the ring A and the arrow in each case denotes the bond to D,
D is the radical of the formula

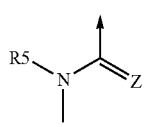

in which the nitrogen is bonded to Q and the arrow denotes the bond to B,
B is a radical from the group of

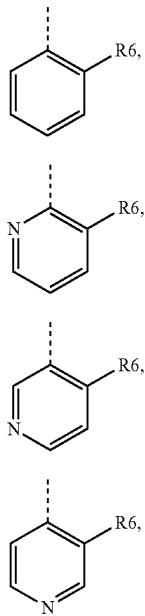

B-1

B-2

B-3

B-4

-continued

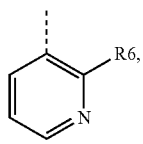
B-5

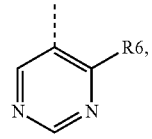
B-6

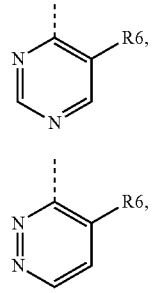
B-7

B-8

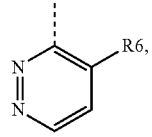
B-9

B-10

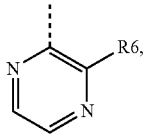
B-11

B-13

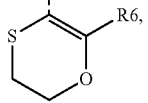
B-18

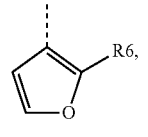
B-19

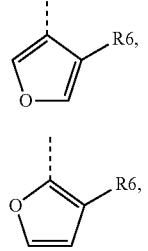
B-20

-continued

B-21 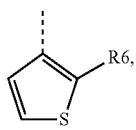

B-22 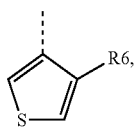

B-23 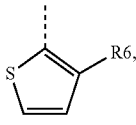

B-31 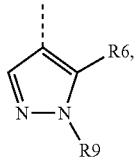

B-32 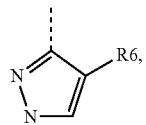

B-33 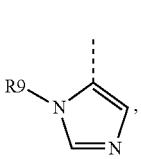

B-34 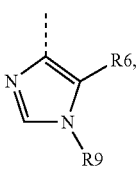

B-35 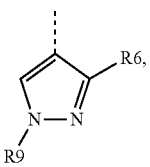

B-36 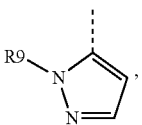

B-52

-continued

B-53 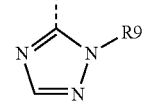

in which the broken line denotes the bond to D and where B additionally bears n R7 substituents, Z is oxygen or sulphur, R1 is a radical from the group of hydrogen (but only in the case of the combination of A-1 with Q-2), halogen, cyano, nitro, $C_1$-$C_4$-alkyl, $C_1$-$C_4$ haloalkyl, $C_1$-$C_4$-alkoxy, $C_1$-$C_4$-haloalkoxy and $C_1$-$C_4$-alkylsulphonyl, R2 is a radical from the group of halogen, $C_1$-$C_4$-alkyl, $C_1$-$C_4$ haloalkyl, $C_1$-$C_4$-alkoxy, $C_1$-$C_4$-haloalkoxy, $C_1$-$C_6$ alkylthio, $C_1$-$C_6$-haloalkylthio, $C_1$-$C_6$ alkylsulphinyl, $C_1$-$C_6$-haloalkylsulphinyl, $C_1$-$C_6$-alkylsulphonyl and $C_1$-$C_6$-haloalkylsulphonyl, R3 is a radical from the group of hydrogen, halogen, $C_1$-$C_4$-alkyl, $C_1$-$C_4$ haloalkyl, R5 is a radical from the group of hydrogen, $C_1$-$C_4$-alkyl, $C_3$-$C_4$-alkenyl, $C_3$-$C_4$-alkynyl, $C_1$-$C_4$-alkylcarbonyl, cyano-$C_1$-$C_4$-alkyl and C(=O)—B, R6 is a radical from the group of halogen, nitro, hydroxyl, $C_1$-$C_4$-alkyl, $C_1$-$C_4$ haloalkyl, $C_1$-$C_4$-alkoxy, $C_1$-$C_4$-haloalkoxy, $C_1$-$C_4$ alkylthio, $C_1$-$C_4$-haloalkylthio, $C_1$-$C_4$-alkylsulphonyl and heteroaryl, R7 is a radical from the group of halogen, $C_1$-$C_4$-alkyl and $C_1$-$C_4$-haloalkyl, R9 is $C_1$-$C_4$-alkyl, m is a number from the group of 0, 1, 2, 3 and 4, where, when m>1, the R2 radicals may be the same or different, and n is a number from the group of 0 and 1.

5. Compound of formula (I) according to claim 1 in which A is a radical from the group of A-1 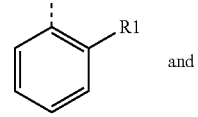
and A-2 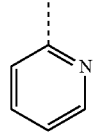

in which the broken line denotes the bond to Q and where A additionally bears m R2 substituents, Q is a radical from the group of Q-1 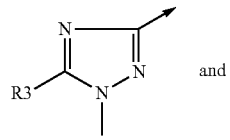
and -continued

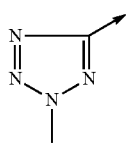
Q-2 in which the nitrogen is joined to the ring A and the arrow in each case denotes the bond to D, D is the radical of the formula

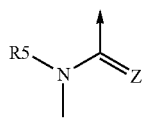

in which the nitrogen is bonded to Q and the arrow denotes the bond to B,

B is a radical from the group of

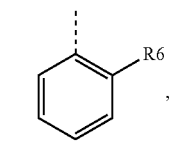
B-1

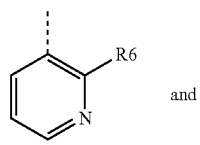
B-5 and

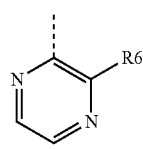
B-11 in which the broken line denotes the bond to D and where B additionally bears n R7 substituents, Z is oxygen, R1 is a radical from the group of halogen, $C_1$-$C_4$-alkyl, $C_1$-$C_4$-haloalkyl, $C_1$-$C_4$-alkoxy and $C_1$-$C_4$-haloalkoxy, R2 is a radical from the group of halogen, $C_1$-$C_4$-alkyl, $C_1$-$C_4$-haloalkyl, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl and $C_1$-$C_6$-haloalkylsulphonyl, R3 is hydrogen, R5 is hydrogen, R6 is a radical from the group of halogen, nitro, $C_1$-$C_4$-alkyl, $C_1$-$C_4$-haloalkyl and $C_1$-$C_4$-haloalkoxy, R7 is halogen, m is a number from the group of 0, 1, 2, 3 and 4, where, when m>1, the R2 radicals may be the same or different, and n is a number from the group of 0 and 1.

6. The compound of formula (I) according to claim 1, in which

A is 2-chloro-6-fluorophenyl,

B is 2-tri(fluoromethyl)phenyl

Q is

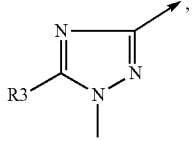
(Q-1)

R3 is hydrogen,
R5 is hydrogen, and
Z is oxygen.

7. The compound of formula (I) according to claim 1, in which
A is 2-bromo-6-fluorophenyl,
B is 2-iodophenyl
Q is

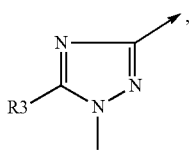
(Q-1)

R3 is hydrogen,
R5 is hydrogen, and
Z is oxygen.

8. The compound of formula (I) according to claim 1, in which
A is 2,3,6-trifluorophenyl,
B is 2-iodophenyl
Q is

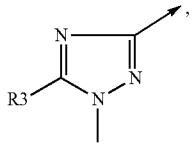
(Q-1)

R3 is hydrogen,
R5 is hydrogen, and
Z is oxygen.

9. The compound of formula (I) according to claim 1, in which
A is 2,6-difluorophenyl,
B is 2-(trifluoromethyl)phenyl
Q is

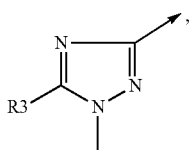
(Q-1)

R3 is hydrogen,
R5 is hydrogen, and
Z is oxygen.

10. The compound of formula (I) according to claim 1, in which

A is 2-fluoro-6-(trifluoromethyl)phenyl,
B is 2-(trifluoromethyl)phenyl,
Q is

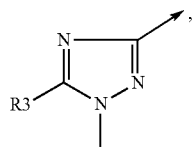
(Q-1)

R3 is hydrogen,
R5 is hydrogen, and
Z is oxygen.

11. The compound of formula (I) according to claim 1, in which

A is 2,6-difluorophenyl,
B is 2-fluoro-6-(trifluoromethyl)phenyl,
Q is

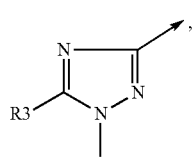
(Q-1)

R3 is hydrogen,
R5 is hydrogen, and
Z is oxygen.

12. The compound of formula (I) according to claim 1, in which

A is 2,6-dichlorophenyl,
B is 2-(trifluoromethyl)phenyl,
Q is

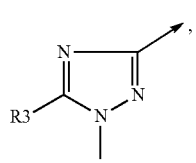
(Q-1)

R3 is hydrogen,
R5 is hydrogen, and
Z is oxygen.

13. The compound of formula (I) according to claim 1, in which

A is 2,4,6-trifluorophenyl,
B is 2-ethylphenyl,
Q is

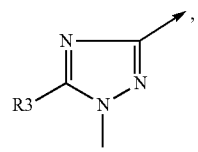
(Q-1)

R3 is hydrogen,
R5 is hydrogen, and
Z is oxygen.

14. The compound of formula (I) according to claim 1, in which

A is 2,4,6-trifluorophenyl,
B is 2-(trifluoromethyl)phenyl,
Q is

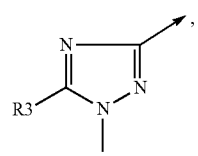
(Q-1)

R3 is hydrogen,
R5 is hydrogen, and
Z is oxygen.

15. The compound of formula (I) according to claim 1, in which

A is 2,4,6-trifluorophenyl,
B is 2-iodophenyl,
Q is

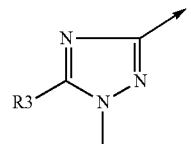
(Q-1)

R3 is hydrogen,
R5 is hydrogen, and
Z is oxygen.

16. The compound of formula (I) according to claim 1, in which

A is 2,6-difluorophenyl,
B is 2-ethylphenyl,
Q is

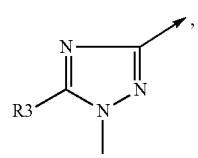
(Q-1)

R3 is hydrogen,
R5 is hydrogen, and
Z is oxygen.

17. The compound of formula (I) according to claim 1, in which

A is 2-bromo-6-fluorophenyl,
B is 2-(trifluoromethyl)phenyl,
Q is

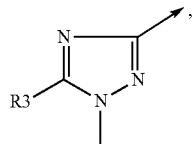
(Q-1)

R3 is hydrogen,
R5 is hydrogen, and
Z is oxygen.

18. The compound of formula (I) according to claim 1, in which

A is 2,3,5,6-tetrafluorophenyl,
B is 2-(trifluoromethyl)phenyl,
Q is

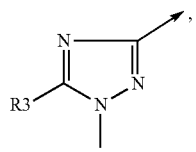
(Q-1)

R3 is hydrogen,
R5 is hydrogen, and
Z is oxygen.

19. The compound of formula (I) according to claim 1, in which

A is 2-fluoro-6-(trifluoromethyl)phenyl,
B is 2-iodophenyl,
Q is

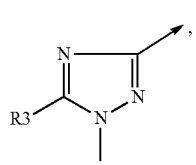
(Q-1)

R3 is hydrogen,
R5 is hydrogen, and
Z is oxygen.

20. The compound of formula (I) according to claim 1, in which

A is 2,3,6-trifluorophenyl,
B is 2-ethylphenyl,
Q is

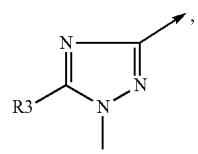
(Q-1)

R3 is hydrogen,
R5 is hydrogen, and
Z is oxygen.

21. The compound of formula (I) according to claim 1, in which

A is 2,6-difluorophenyl,
B is 2-iodophenyl,
Q is

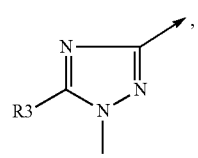
(Q-1)

R3 is hydrogen,
R5 is hydrogen, and
Z is oxygen.

22. The compound of formula (I) according to claim 1, in which

A is 2-chloro-6-fluorophenyl,
B is 2-iodophenyl,
Q is

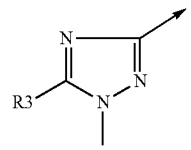
(Q-1)

R3 is hydrogen,
R5 is hydrogen, and
Z is oxygen.

23. The compound of formula (I) according to claim 1, in which

A is 2,3,6-trifluorophenyl,
B is 2-(trifluoromethyl)phenyl,
Q is

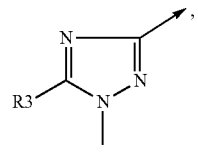
(Q-1)

R3 is hydrogen,
R5 is hydrogen, and
Z is oxygen.

24. Composition, comprising a content of at least one compound of formula (I) according to claim 1.

25. Method for controlling pests, comprising allowing a compound of formula (I) according to claim 1 or a composition thereof to act on one or more pests and/or their habitat.

26. Compound of formula (IIa-1-a)

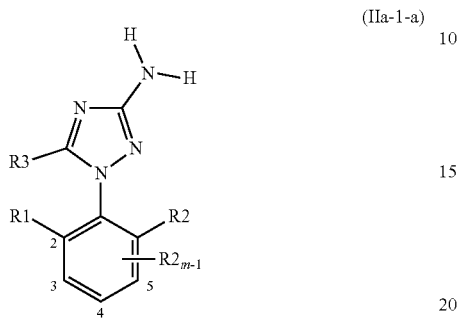

in which

R1 is a radical from the group of halogen, cyano, nitro, amino, hydroxyl, optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)aminocarbonyl, aminothiocarbonyl, $C_1$-$C_6$-alkylaminosulphonyl, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, aryl, aryloxy, arylthio, heteroaryl, heteroaryloxy and heteroarylthio, R2 is a radical from the group of halogen, cyano, nitro, amino, hydroxyl, optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, aryl, aryloxy, arylthio, heteroaryl, heteroaryloxy and heteroarylthio, R3 is a radical from the group of hydrogen, halogen, cyano, nitro, amino, hydroxyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-haloalkyl, $C_1$-$C_6$-haloalkoxy, $C_1$-$C_6$-haloalkylthio, $C_1$-$C_6$-haloalkylsulphinyl and $C_1$-$C_6$-haloalkylsulphonyl, and m is a number from the group of 1, 2 and 3, and excluding the compound where R3 is H; R1 and R2 are each chlorine, m is 2 and the additional R2 is 4-$CF_3$.

27. Compound of formula (IIa-1-a) according to claim 26, in which R3 is hydrogen.

28. Compound of formula (1-9)

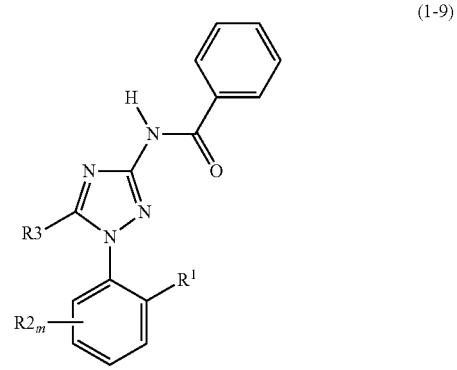

in which

R1 is a radical from the group of halogen, cyano, nitro, amino, hydroxyl, optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)aminocarbonyl, aminothiocarbonyl, $C_1$-$C_6$-alkylaminosulphonyl, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, aryl, aryloxy, arylthio, heteroaryl, heteroaryloxy and heteroarylthio, R2 is a radical from the group of halogen, cyano, nitro, amino, hydroxyl, optionally singly or multiply, identically or differently substituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, aryl, aryloxy, arylthio, heteroaryl, heteroaryloxy and heteroarylthio, R3 is a radical from the group of hydrogen, halogen, cyano, nitro, amino, hydroxyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-haloalkyl, $C_1$-$C_6$-haloalkoxy, $C_1$-$C_6$-haloalkylthio, $C_1$-$C_6$-haloalkylsulphinyl and $C_1$-$C_6$-haloalkylsulphonyl, wherein m is a number from the group of 0, 1, 2, 3 and 4, where, when m>1, the R2 radicals may be the same or different.

29. Compound of formula (1-9) according to claim 28, in which R3 is hydrogen.

\* \* \* \* \*